United States Patent
Zurovcik

(10) Patent No.: US 11,944,519 B2
(45) Date of Patent: Apr. 2, 2024

(54) UNBACKED AND MODIFIABLE TAPES AND SKIN DRESSINGS

(71) Applicant: Worldwide Innovative Healthcare, Inc., Cambridge, MA (US)

(72) Inventor: Danielle R. Zurovcik, West Newton, PA (US)

(73) Assignee: WORLDWIDE INNOVATIVE HEALTHCARE, INC., Cambridge, MA (US)

( * ) Notice: Subject to any disclaimer, the term of this patent is extended or adjusted under 35 U.S.C. 154(b) by 381 days.

(21) Appl. No.: 14/965,811

(22) Filed: Dec. 10, 2015

(65) Prior Publication Data

US 2016/0095756 A1    Apr. 7, 2016

Related U.S. Application Data

(63) Continuation-in-part of application No. 14/929,146, filed on Oct. 30, 2015, now abandoned, which is a
(Continued)

(51) Int. Cl.
*A61F 13/00* (2006.01)
*A61B 17/08* (2006.01)
(Continued)

(52) U.S. Cl.
CPC ........ *A61F 13/00068* (2013.01); *A61B 50/30* (2016.02); *A61F 13/0216* (2013.01);
(Continued)

(58) Field of Classification Search
CPC ............. A41D 13/1107; A61F 13/0269; A61F 13/0273; A61F 13/0266; A61F 13/0246;
(Continued)

(56) References Cited

U.S. PATENT DOCUMENTS 2,608,503 A * 8/1952 Meyer .................... B32B 27/00
                                                            206/820
4,024,312 A   5/1977 Korpman
(Continued)

FOREIGN PATENT DOCUMENTS

JP    H01110138 A    4/1989
JP    H0689309 B2    11/1994

OTHER PUBLICATIONS

Yavrouian et al., Multi-Layer Laminated Thin Films for Inflatable Structures, NASA Tech Briefs, Apr. 2005, pp. 17-18.

*Primary Examiner* — Caitlin A Carreiro
(74) *Attorney, Agent, or Firm* — Douglas Denninger

(57) ABSTRACT

Tapes and methods including an unbacked construction of at least one liquid layer adhesive that has been at least one of dried and cured. Occlusive tissue dressings, tapes and methods including an elastomeric drape and, for backed drapes and some unbacked drapes, a liquid component, at least partially cross-linked at least after one of drying and curing, suitable for application at a dressing-to-skin interface in order to create a substantially air-tight seal. The same or a different liquid component may be applied by a user at a tube-to-dressing interface of an elastomeric drape to create a similar air-tight seal around the tube, if not occlusively sealed during its manufacture. Featured are unbacked tapes, a drape with liquid sealant component, a liquid layered drape with liquid sealant component, and a liquid layered drape.

66 Claims, 35 Drawing Sheets

Related U.S. Application Data continuation of application No. 13/745,690, filed on Jan. 18, 2013, now Pat. No. 9,173,777.

(60) Provisional application No. 61/588,121, filed on Jan. 18, 2012, provisional application No. 62/090,350, filed on Dec. 10, 2014, provisional application No. 62/090,437, filed on Dec. 11, 2014, provisional application No. 62/182,417, filed on Jun. 19, 2015.

(51) Int. Cl.
| | | |
|---|---|---|
| A61B 46/20 | (2016.01) | |
| A61B 50/00 | (2016.01) | |
| A61B 50/30 | (2016.01) | |
| A61F 13/02 | (2006.01) | |
| A61F 13/0203 | (2024.01) | |
| A61F 13/0246 | (2024.01) | |
| A61L 15/58 | (2006.01) | |
| A61M 1/00 | (2006.01) | |
| B32B 3/26 | (2006.01) | |
| B32B 7/05 | (2019.01) | |
| B32B 7/06 | (2019.01) | |
| B32B 7/12 | (2006.01) | |
| B32B 7/14 | (2006.01) | |
| B32B 29/00 | (2006.01) | |
| B32B 29/02 | (2006.01) | |

(52) U.S. Cl.
CPC ...... *A61F 13/0226* (2013.01); *A61F 13/0246* (2013.01); *A61L 15/58* (2013.01); *A61M 1/915* (2021.05); *B32B 3/266* (2013.01); *B32B 7/05* (2019.01); *B32B 7/06* (2013.01); *B32B 7/12* (2013.01); *B32B 7/14* (2013.01); *B32B 29/002* (2013.01); *B32B 29/02* (2013.01); *A61B 17/085* (2013.01); *A61B 2046/205* (2016.02); *A61B 2050/006* (2016.02); *A61B 2050/0065* (2016.02); *A61B 2050/314* (2016.02); *A61B 2217/005* (2013.01); *A61F 2013/0017* (2013.01); *A61F 2013/00174* (2013.01); *A61F 2013/00268* (2013.01); *A61F 2013/00412* (2013.01); *A61F 2013/00536* (2013.01); *A61F 2013/00702* (2013.01); *A61M 1/82* (2021.05); *A61M 1/962* (2021.05); *B32B 2250/44* (2013.01); *B32B 2307/7265* (2013.01); *B32B 2307/748* (2013.01); *B32B 2405/00* (2013.01); *B32B 2535/00* (2013.01); *B32B 2556/00* (2013.01)

(58) Field of Classification Search
CPC .............. A61F 13/0253; A61F 13/0259; A61F 13/00068; A61F 13/0216; A61F 13/0226; A61F 2013/00089; A61F 2013/53925; A61F 2013/0017; A61F 2013/00174; A61F 2013/00268; A61F 2013/00412; A61F 2013/00538; A61F 2013/00702; A61B 34/30; A61B 17/085; A61B 2217/005; A61B 2050/006; A61B 2050/314; A61B 2046/205; A61B 50/30; A61L 15/58; A61M 1/90; B32B 2556/00; B32B 2535/00; B32B 2405/00; B32B 2307/7265; B32B 2307/748; B32B 2250/44; B32B 29/002; B32B 29/02; B32B 3/266; B32B 7/05; B32B 7/06; B32B 7/12; B32B 7/14
USPC ...... 128/845; 602/52, 57–58, 75, 42, 54–55, 602/903; 428/41.5; 442/184
See application file for complete search history.

(56) References Cited

U.S. PATENT DOCUMENTS

| | | |
|---|---|---|
| 4,060,081 A | 11/1977 | Yannis et al. |
| 4,323,557 A | 4/1982 | Rosso et al. |
| 5,019,096 A * | 5/1991 | Fox, Jr. ............... A61L 31/10 606/151 |
| 5,516,581 A | 5/1996 | Kreckel et al. |
| 5,636,643 A | 6/1997 | Argenta et al. |
| 5,860,420 A | 1/1999 | Wiedner et al. |
| 5,947,917 A * | 9/1999 | Carte ................ A61F 13/0253 602/58 |
| 6,068,852 A | 5/2000 | Shah |
| 6,309,745 B1 * | 10/2001 | Willms ............... A61F 13/58 428/354 |
| 6,874,657 B2 | 4/2005 | Metzner et al. |
| 7,435,423 B2 | 10/2008 | Collinge et al. |
| 7,611,500 B1 | 11/2009 | Lina et al. |
| 8,007,491 B2 | 8/2011 | Pinto et al. |
| 2003/0059607 A1 | 3/2003 | Schumann et al. |
| 2003/0120229 A1 * | 6/2003 | de Jong ............ A61F 13/0276 604/385.01 |
| 2004/0138602 A1 | 7/2004 | Rossen |
| 2006/0030790 A1 | 2/2006 | Braig et al. |
| 2006/0195993 A1 | 9/2006 | O'Neill et al. |
| 2006/0228318 A1 | 10/2006 | Fabo |
| 2007/0147947 A1 | 6/2007 | Stenton et al. |
| 2008/0183156 A1 | 7/2008 | Yoo |
| 2008/0280086 A1 * | 11/2008 | Sheridan ............... B32B 27/00 428/41.5 |
| 2009/0044895 A1 * | 2/2009 | Fortune ............... A61L 31/129 156/60 |
| 2009/0152137 A1 * | 6/2009 | Estes ................... A61B 50/30 128/849 |
| 2010/0112036 A1 | 5/2010 | Zhang et al. |
| 2010/0137775 A1 | 6/2010 | Hu et al. |
| 2010/0160484 A1 | 6/2010 | MacDonald et al. |
| 2010/0174250 A1 | 7/2010 | Hu et al. |
| 2010/0228205 A1 | 9/2010 | Hu et al. |
| 2010/0274205 A1 | 10/2010 | Morelli et al. |
| 2011/0066123 A1 | 3/2011 | Tout et al. |
| 2011/0106030 A1 | 5/2011 | Scholz |
| 2012/0240942 A1 | 9/2012 | Llinas et al. |
| 2012/0245540 A1 | 9/2012 | Zimnitsky et al. |
| 2012/0247487 A1 | 10/2012 | Llinas et al. |
| 2012/0316521 A1 | 12/2012 | Webster |
| 2014/0079900 A1 * | 3/2014 | Ramirez ................. C09J 7/21 428/41.8 |
| 2015/0159066 A1 | 6/2015 | Hartwell et al. |

* cited by examiner

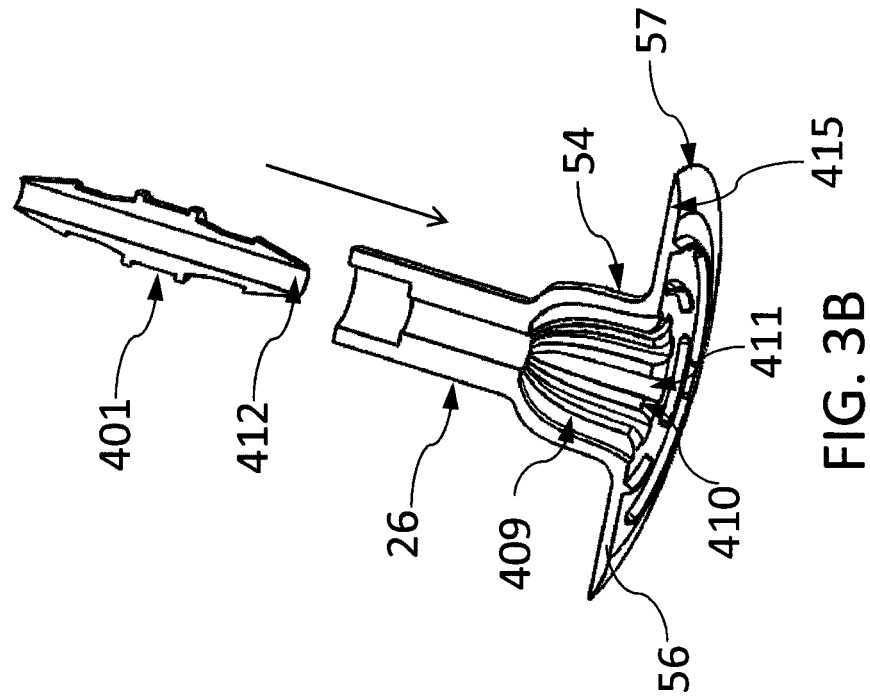
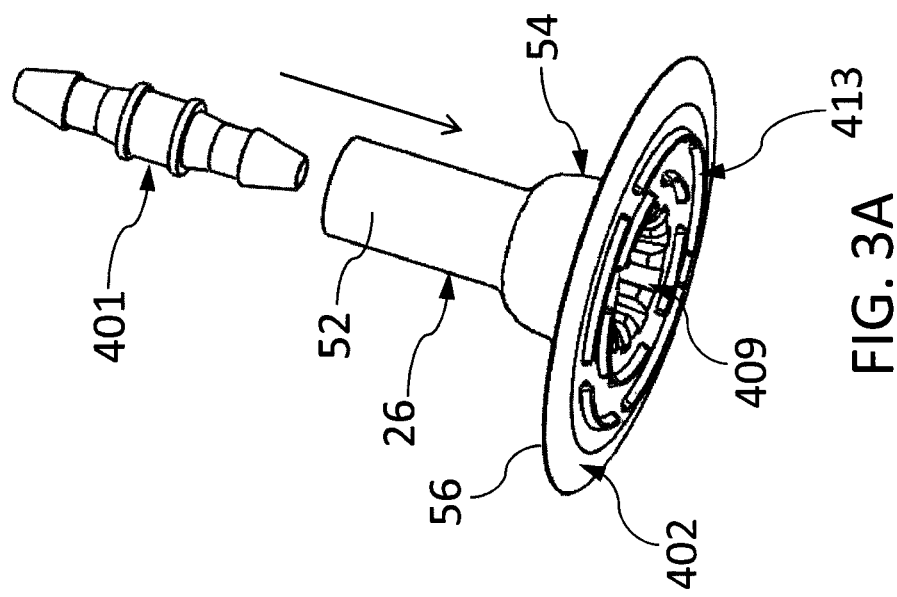

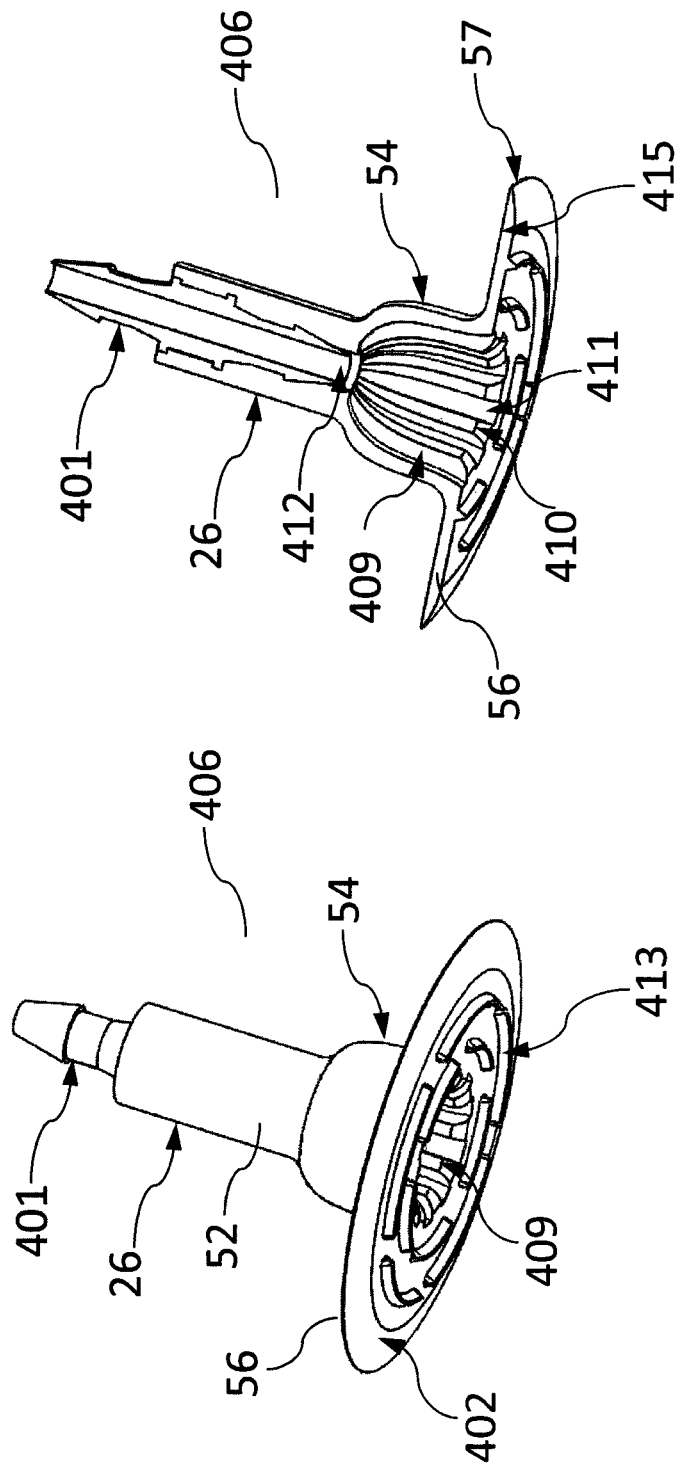

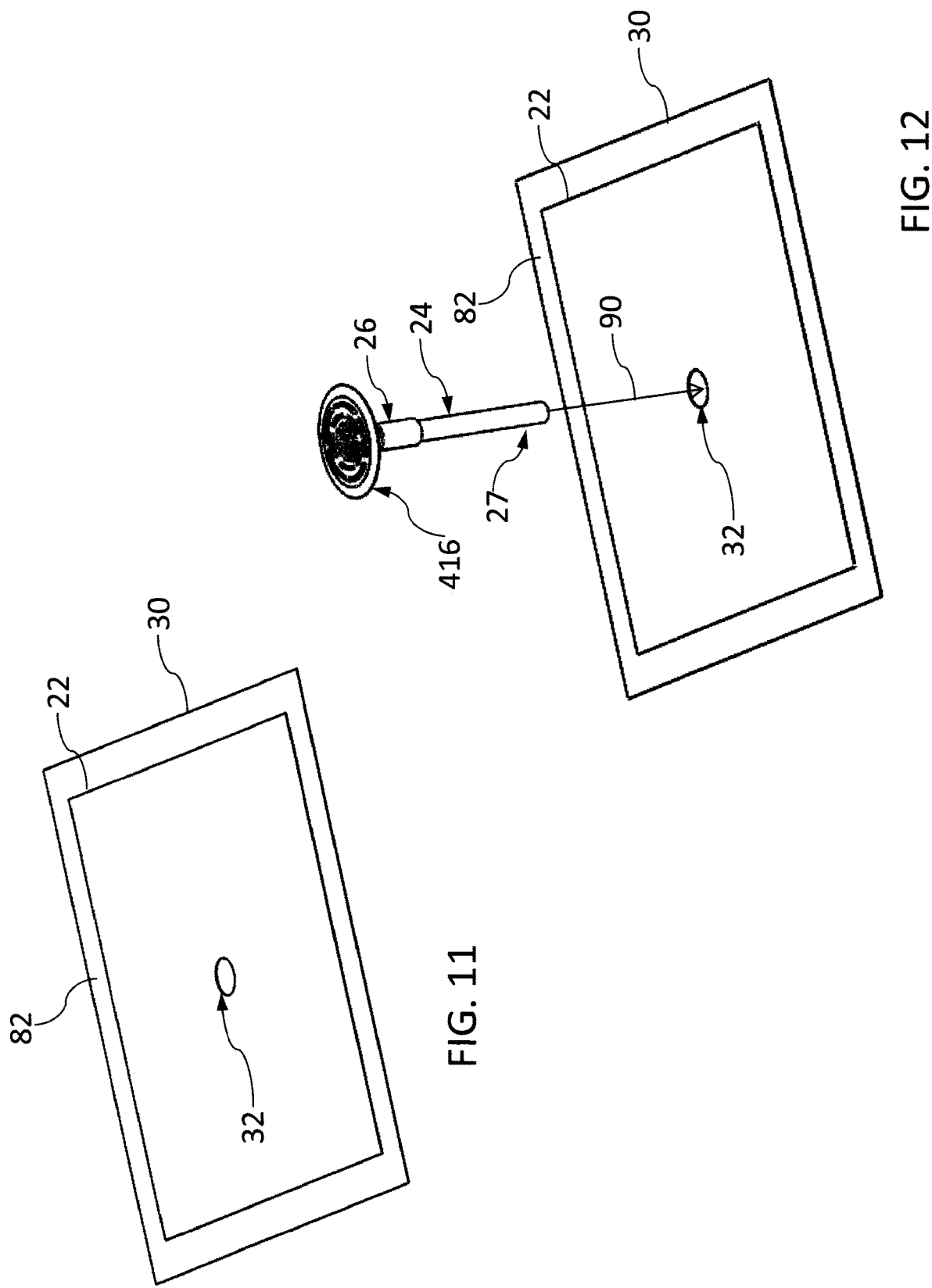

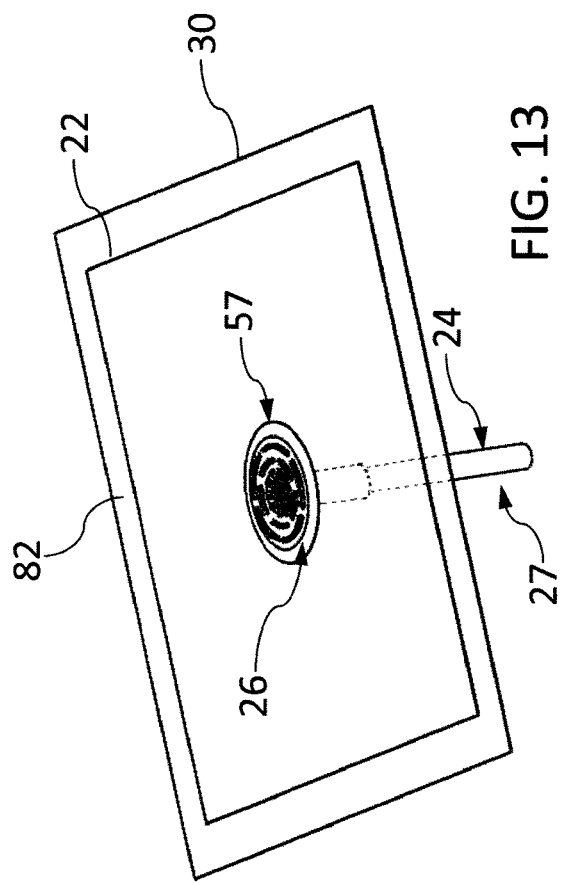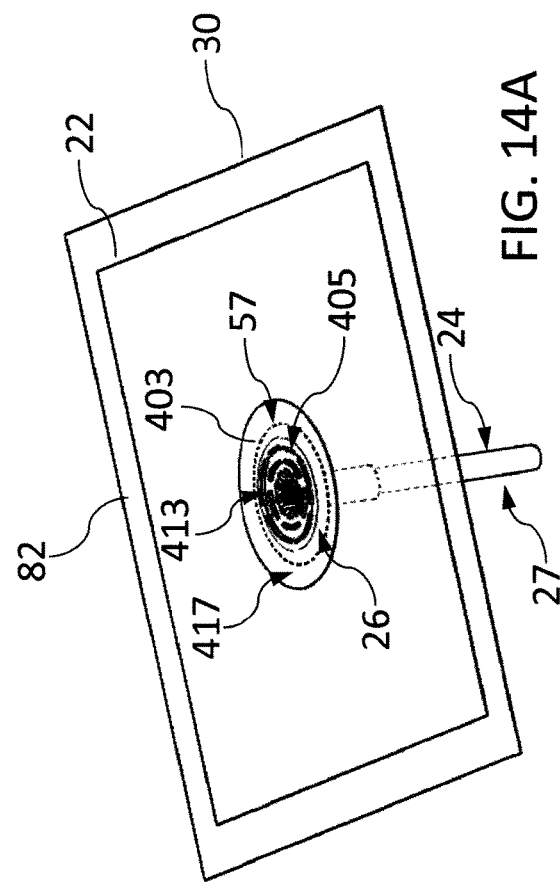

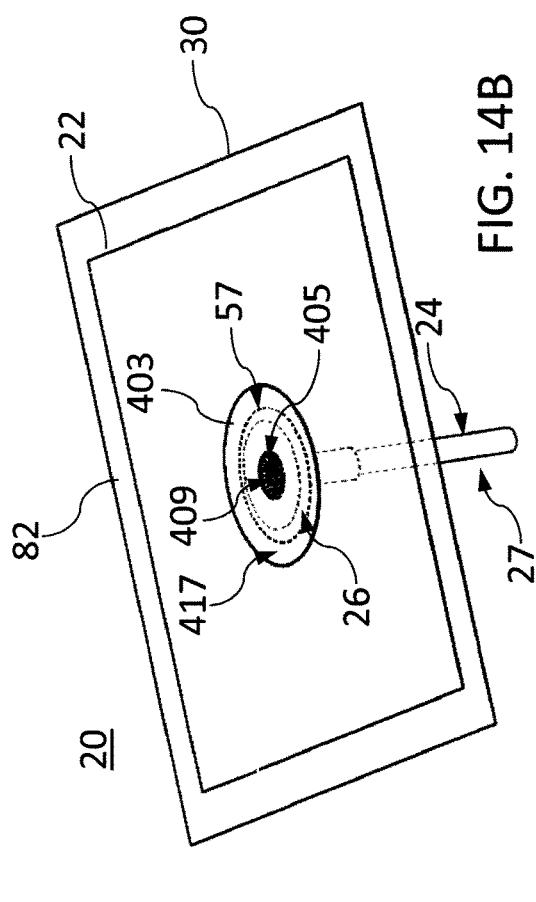
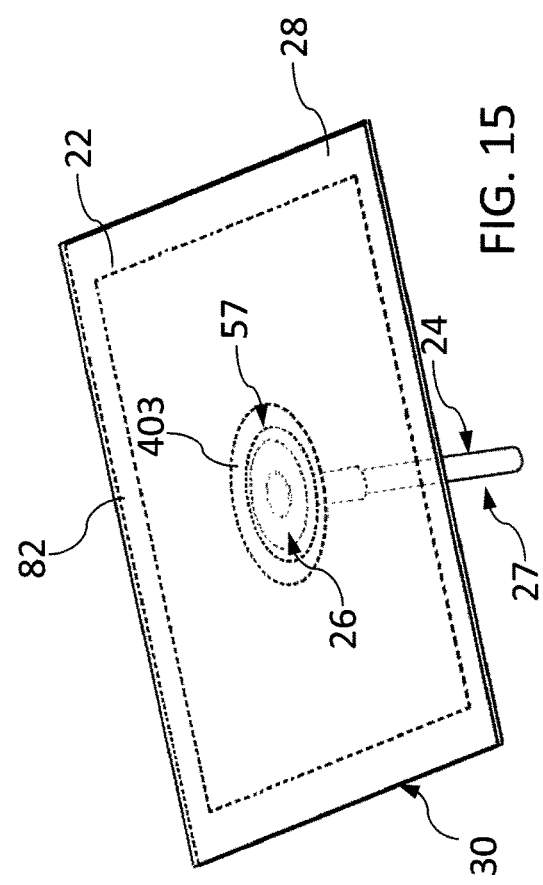

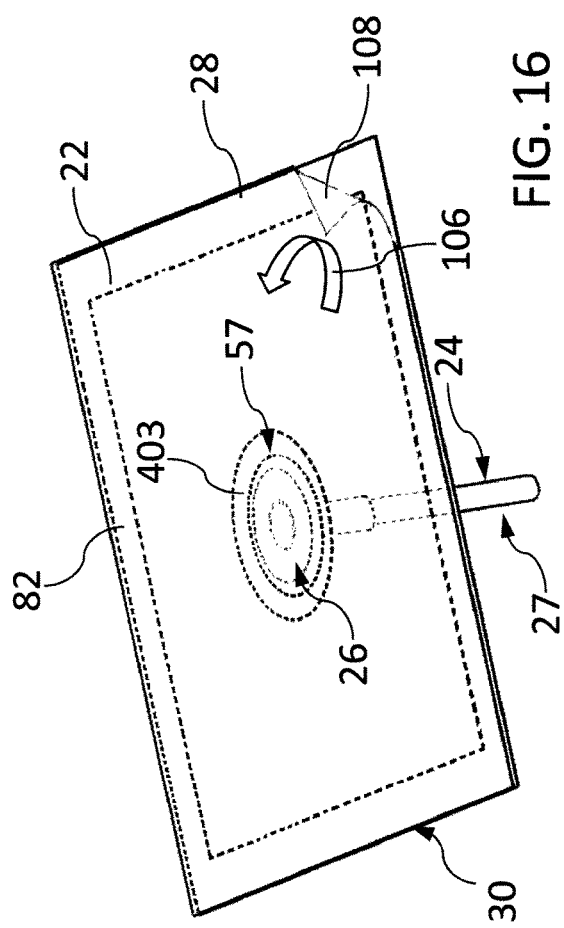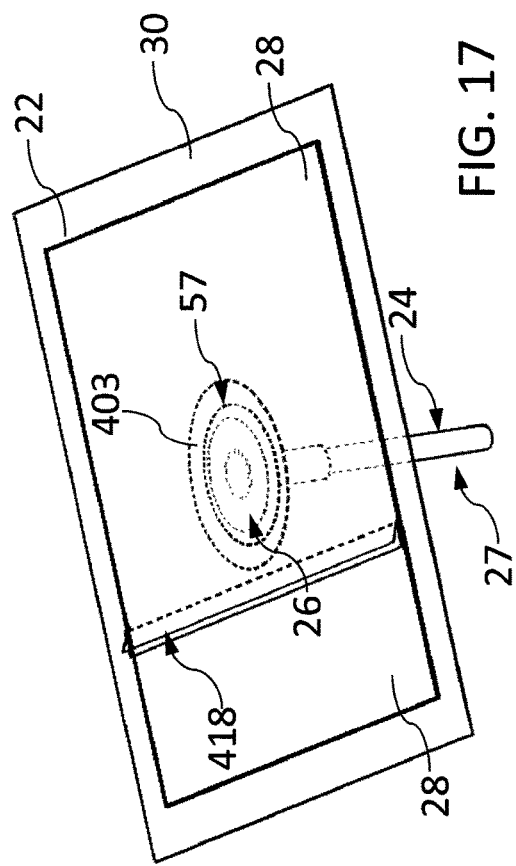

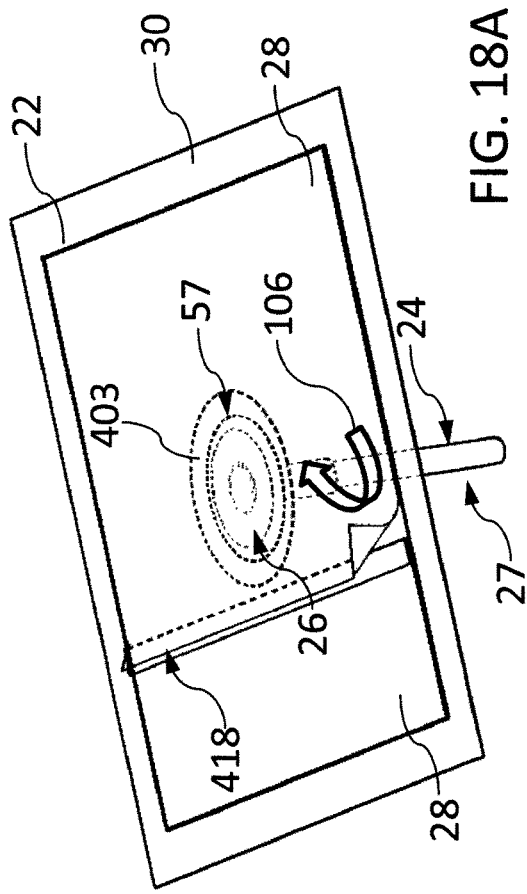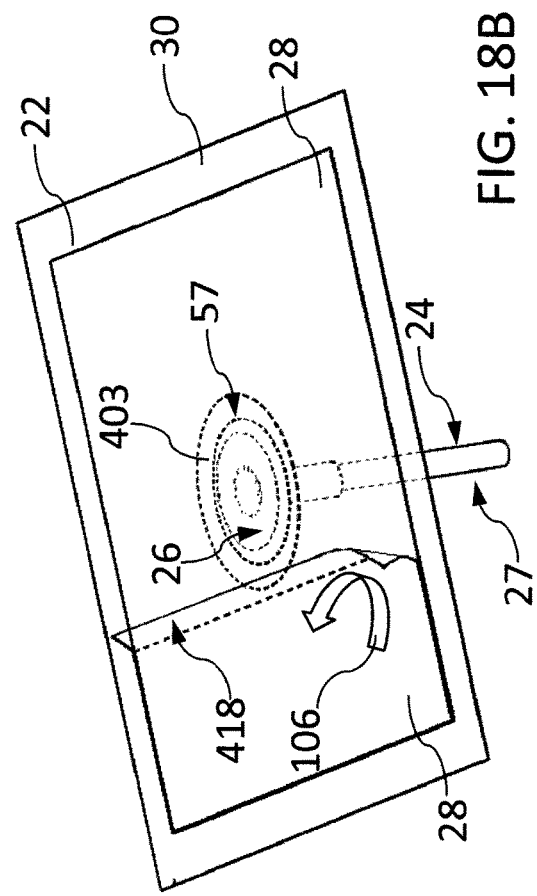

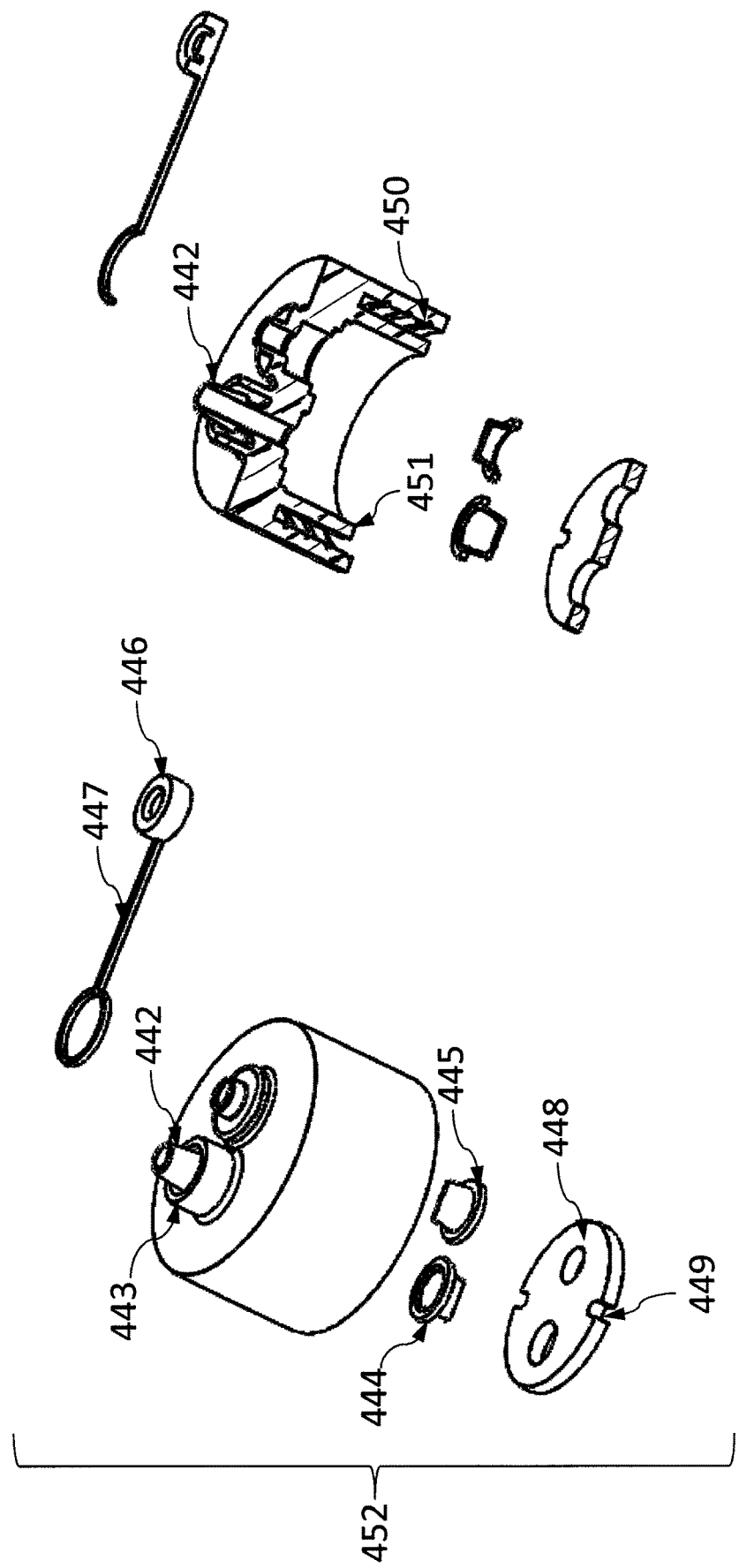

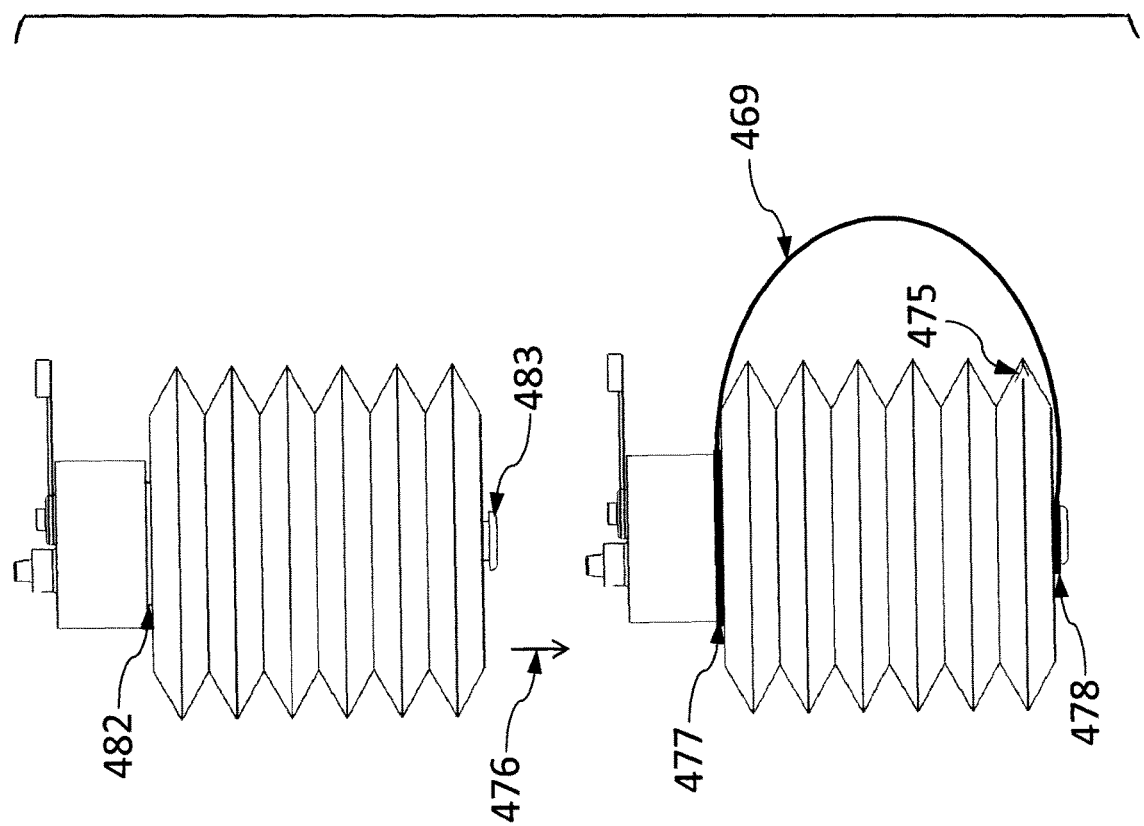

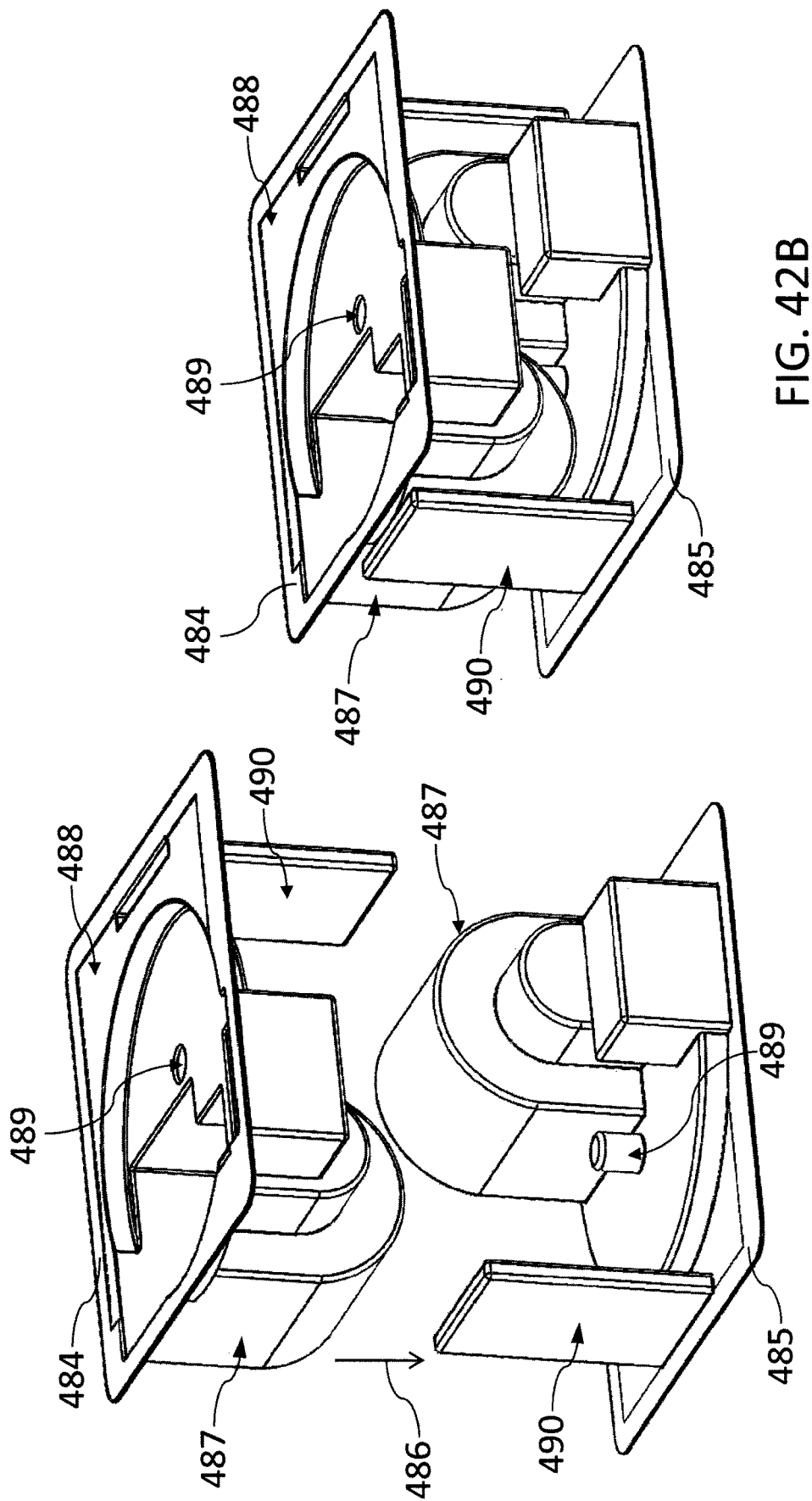

UNBACKED AND MODIFIABLE TAPES AND SKIN DRESSINGS

CROSS-REFERENCE TO RELATED APPLICATION

This application is a continuation-in-part application of U.S. patent application Ser. No. 14/929,146 filed 30 Oct. 2015 which is a continuation of U.S. application Ser. No. 13/745,690 filed 18 Jan. 2013, now U.S. Pat. No. 9,173,777, and claims priority to U.S. Provisional Application Nos. 61/588,121 filed 18 Jan. 2012; 62/090,350 filed 10 Dec. 2014; 62/090,437 filed 11 Dec. 2014; and 62/182,417 filed 19 Jun. 2015 by the present inventor. The entire contents of each of the above-mentioned applications are incorporated herein by reference.

FIELD OF THE INVENTION

This invention relates to tapes and dressings intended to provide a fluid-impervious barrier over skin, including dressings suitable for negative pressure wound therapy.

BACKGROUND OF THE INVENTION

Negative pressure wound therapy ("NPWT") is an effective technology for treating open wounds. NPWT devices were originally accepted by the U.S. Food and Drug Administration ("FDA") in 1995, when the FDA approved a 510 (K) for the Kinetic Concepts Inc. ("KCI")'s V.A.C.® device. The definition of NPWT devices by the FDA has changed over the years; in general terms, its definition is: a system that is used to apply negative pressure for wound management purposes, including the removal of fluids (i.e., wound exudates, irrigation fluids, and infectious materials). The negative pressure is applied through a porous dressing positioned into or over the wound cavity, depending on wound type and depth, or over a flap or graft; the dressing distributes the pressure while removing fluids from the wound. NWPT systems typically include:
  Non-adhesive wound dressing used to fill the wound cavity (e.g., a sterilized medical sponge or gauze; a.k.a., non-adhesive packing materials);
  Drainage tube placed adjacent to or into the dressing;
  Occlusive transparent film placed over the dressing (and potentially the drainage tube) and adhered to the skin to maintain a seal;
  Collection container for drained fluids from the wound; and
  Low pressure vacuum source.

NPWT has been approved by the FDA to treat many wound types: chronic, acute, traumatic, sub-acute and dehisced wounds, partial-thickness burns, ulcers (such as diabetic, venous or pressure), surgically closed incisions (a.k.a., closed surgical incisions), flaps and grafts. The prescribed therapy time depends on wound type, wound dimensions, and patient conditions; it typically lasts from four weeks to four months. Disposable dressing components are changed approximately every three days.

Extensive clinical trials have demonstrated the success of negative pressure in healing the approved wound types by applying a controlled negative pressure typically between 20 mmHg and 200 mmHg. Most studies applied a constant vacuum pressure, with 125 mmHg being the most common, although cyclic and intermittent studies have also shown positive results. Evidence supporting the use of NPWT in the treatment of chronic, non-healing wounds exists primarily in the form of nonrandomized, controlled trials; prospective and retrospective large and small case series; single-center studies; and single case studies, with few randomized, controlled clinical trials. Studies also exist that demonstrate NPWT benefits in healing acute wounds. Additionally, since 2006, benefits of managing surgical incisions post-operatively have been shown with improved clinical outcomes; at least ten studies have been published to date. From these studies, proven medical benefits of NPWT treatment include:
  Promotes blood flow (perfusion) at the wound;
  Removes interstitial fluid (a.k.a., wound exudates), reduces edema;
  Decreases counts of bacteria and infectious materials;
  Increases rate of granulation tissue formation, reducing scar tissue formation;
  Increases growth factors and fibroblasts;
  Uniformly draws the wound edges together;
  Provides a protected healing environment; and
  Provides a moist environment.

Although significant clinical evidence exists to support the benefit of NPWT as a safe therapy in healing chronic wounds, it is possible during NPWT to rupture a vein or artery. Usually, a machine safety alarm will signify a fluid leak rate that exceeds the rate that the machine was designed for. This alarmed leak rate typically includes the combination of both air and liquid, and typically has an upper safety limit of the minimum blood flow rate possible out of a wound cavity with an actively bleeding vein or artery. If a vein or artery accidently ruptures, the system must shut down. Therefore, it is very important to have a safety feature that stops negative pressure if this occurs, in order not to actively exsanguinate the patient.

Lina et al. describe in U.S. Pat. No. 7,611,500 and WO1996/005873 an initial apparatus used for NPWT. In practice, the device proved to be effective; however, one major limitation was detected: the high electrical grid power source needed to operate the device limited the mobility of a patient. Therefore, future refinements, such as that described by Hunt et al. in U.S. Pat. No. 6,142,982, incorporated rechargeable batteries for the power source. Batteries increased patient mobility, but time was limited by the life of the batteries between charges. Additionally, battery management became an issue, especially for facilities with a high number of NPWT patients, and electrical grid power was still needed to recharge the batteries.

Eliminating the need for electrical power, via the grid or batteries, would create a more widely applicable, clinically viable therapy. The power requirement variability of a system is dependent on the desired vacuum pressure, rate of wound exudate removal from the wound cavity, and the leak rate of air into the system. As the air leak rate increases, more power is needed to supply a continuous negative pressure at a predetermined value or threshold range at the wound bed. Air leakage into the NPWT system requires the most power of any other component. Air leaks are the obstacle to creating a vacuum system that does not require a continuous external power source or frequent recharging of its internal power storage. Therefore, the feasibility of a mechanical NPWT system is heavily reliant on the seal quality of every interface in the system. The dressing system has been identified as the main source of air leaks in current NPWT systems, particularly at the interfaces between 1) the dressing and the skin and 2) the tube and the dressing. The amount of air leaks into these interfaces determines the time frequency that the pump needs to be recharged and the magnitude of vacuum pressure applied to the wound cavity at a specific time. These two latter characteristics are dependent system parameters.

Few mechanical NPWT systems are currently available, as described by the present inventor in "Development of a simplified Negative Pressure Wound Device" submitted in 2007 for her Master of Science in Mechanical Engineering at the Massachusetts Institute of Technology. Certain lower-pressure, mechanical devices were disclosed later by Hu et al. in U.S. Patent Application No. 2010/0228205. Current mechanical systems typically use sophisticated-material, planar dressings, such as hydrocolloid dressings, to try to solve the air leak problem. However, the inherent geometry mismatch of a planar dressing and the contoured skin surface often leads to air leaks. The mechanical devices therefore are only applicable for select, relatively flat surfaces on the body and, even then, it is difficult to eliminate air leaks entirely.

Non-electrical pumps are at the low end of the spectrum of medical pumps, typically utilizing bladder pumps and capillary action materials. Bladder pumps are used for both extracting and inserting fluids. By their physical characteristics, they are governed by non-linear spring like properties. Currently, bladder pumps are used in wound treatments for drainage purposes, particularly for internal, body cavity drainage. C. R. Bard, Inc. manufacturers many of these non-electrical pumps; one bladder model frequently used to drain internal cavities is commonly referred to as a Jackson Pratt Drain.

There are various limitations to applying NPWT with existing mechanical, bladder pumps. There are no pressure gauges on the pumps and, therefore, the user does not know the initial magnitude of the negative pressure pulled, and cannot monitor the pressure during therapy. Additionally, there are no air leak detection systems for the current pumps, except to visually watch for the expansion of the bladder at a rate higher than expected. If the pump is clear, one can also visually monitor if the expansion rate is due to air leaks or due to drainage fluid.

Capillary action materials are also currently used to treat wounds by providing very low negative pressure treatment, too low to be considered NPWT. This form of treatment is usually found in dressings such as small topical bandages to provide NPWT-like benefits to very small, self-healing wounds, such as blisters and brush burns. Treating a wound with this technology enhances the healing environment. Capillary action materials are filled with small capillaries between the wound and outside environment. A negative pressure is applied by capillary action of fluid flowing from the wound to the outside environment, thereby, removing interstitial fluid. One example of a capillary action material is Johnson & Johnson's First Aid Advanced Care Advanced Healing Adhesive Pads.

In general, wound dressings are used to cover open wounds for most wound care treatments, including NPWT. These dressings typically consist primarily of a drape component in the form of an adhesive film. An adhesive film wound dressing consists of a backing (i.e., typically an extruded film) with a first and second surface. The first surface is coated with a biocompatible skin contact adhesive (i.e., a pressure sensitive adhesive), and the skin adhesive is protected with a protective liner on its surface opposite the backing prior to placement on the patient. The second surface of the drape may also have a carrier liner, which is typically used for handling purposes. This carrier liner is typically attached with an adhesive that creates a bond between the carrier liner and backing; this bond is stronger than the bond between the protective liner and the skin adhesive. This difference in bond strength allows the protective liner to be peeled away from the skin adhesive, while the carrier liner remains attached to the drape.

Prior to applying the dressing, it may initially be cut by the user to be slightly larger than the size of the wound. Typically, the ideal dressing size is approximately 2-4 cm beyond the circumference of the wound edge. In some embodiments, if the wound dressing is cut, then a border of the carrier liner that extends beyond the drape to further assist in handling the dressing may also be cut-off, which is not ideal. In addition, prior to the dressing application, the periwound skin is typically cleaned, typically with alcohol. Skin prep may also be applied to the periwound skin, in order to protect the periwound skin, increase the adhesive strength of the skin adhesive to the periwound skin, and/or increase the integrity and longevity of the adhesive strength of the skin adhesive to the periwound skin over wear time.

In order to apply the dressing, the protective liner is peeled from the skin adhesive, in order to expose the skin adhesive to atmosphere. The protective liner may be one body, or may be multiple bodies that require removal. The drape is then bonded to the periwound skin with the skin adhesive. The protective liner(s) may be removed prior to or during the bonding process to the skin, but typically, it is done prior to bonding. Then, the carrier liner is removed. The carrier liner may have multiple perforations, layers and/or segments in order to remove different layers or segments of the liner at different times during the application process and/or to make the dressing more conformable to the skin surface. However, the last step of its application is the complete removal of all the carrier liner segments, after which a non-adhesive surface of the backing is left exposed.

The skin adhesive typically bonds to the skin with Van der Waals forces. The ability of Van der Waals forces to provide adequate bond strength is based on the material of the skin adhesive and backing and each of their thicknesses. Typically, the thickness of each layer of material is constant. Theoretically, for the dressing to remain adhered to the skin, the debond toughness (strength of the bond) must be greater than the debonding energy, and the debonding energy is proportional to: the effective thickness of the material (i.e., skin adhesive and drape), the effective strain in the material squared, and the effective elastic modulus of the material, as represented on a first order basis by Equations 1 and 2 below. The backing is typically a polyurethane film, and the skin adhesive is typically acrylic-based. Some dressings may use silicone-based skin adhesives. Some dressings may use rubber-based adhesives.

During its manufacture, the backing is initially a roll of non-adhesive solid film, which is unrolled to coat with the skin adhesive. Then, the protective liner is typically laminated to the adhesive before the backing and skin adhesive layered embodiment is rolled. In some embodiments, the skin adhesive may originally be coated onto the protective liner, prior to adhering it to the backing. If a carrier liner is applied, it may be applied before, simultaneously, or after the skin adhesive and/or protective liner. Ideally, the carrier liner is applied in the same unrolled procedure as the skin adhesive and protective liner, so that an additional unrolling procedure is not necessary. To apply the carrier liner, an adhesive may be first coated onto the liner or to the backing, in order to laminate the carrier liner to the backing. In some embodiments, the carrier liner may be applied with electrostatic adhesive forces with no adhesive applied between the carrier liner and the drape, or other adhesion methods known in the art.

As disclosed in U.S. Provisional Application No. 62/090,350 by the present inventor, the two layered functional body of the backing and skin adhesive for wound dressings currently available on the market typically has (an average, using a least squares, linear regression fit in Microsoft Excel) an effective uniaxial modulus of elasticity (Young's Modulus) above 7E+6 N/m$^2$ in the linear elastic region (i.e., small strain range: 0-0.2 used in this case), and often above 8E+6 N/m$^2$, using a strain rate of 0.225/sec to 0.300/sec at ambient conditions. If a small strain range of 0-0.1 is used, the effective uniaxial modulus of elasticity is typically above 9E+6 N/m$^2$ in the linear elastic region, and often above 10E+6 N/m$^2$. For our linear modulus analysis, an Admen eXpert series (Norwood, MA) tensile tester with a 2.2 lbf load cell (Interface, Scottsdale, AZ) was used. In addition, using the same experimental parameters, the stress at 0.2 strain is typically above 1.0 MPa and often above 1.5 MPa, and the knee of the stress versus strain curve typically occurs above 1.0 MPa, and often above 2.0 MPa. For the experimental analyses, the entire cross-sectional area was assumed to be the effective area, and therefore, the resulting effective stress values and moduli are slightly underestimated, due to the thin layer of adhesive.

Dressing technologies have tried to address the issue of air leaks into NPWT systems. This is important to both electrical and mechanical systems to reduce their necessary power requirements. In mechanical systems, it is necessary for clinically relevant device functionality, such that power input and pump recharge time is reasonable for a caregiver and/or patient to perform. For electrical systems, air leak reduction reduces the number of, if not completely eliminates, false-positive, alarmed emergency system shutdowns, which are an indication of potential blood flow. Air leak reduction allows battery designs to last longer on one battery charge and use lower power capacity batteries altogether. Air leak elimination potentially eliminates the need for a continuous power supply, as the vacuum pressure can be maintained in the occlusive environment within a specified threshold, for which the timeframe depends on the pump parameters, initial air-volume of the system, and exudate removal rate (typically less than 100 mL/day) from the wound.

Currently, most NPWT dressings (the drape component) are thin, planar, tape-like adhesive dressings, as described above, that must be applied to a contoured area of skin. The backing on the dressing must be removed to expose the adhesive, and then the dressing is applied to the skin. The pre-application handling of the dressings alone introduces a probability for air leaks, as the dressing typically folds onto itself or creases very easily due to its low bending stiffness, even with a carrier liner. Many dressings are thinner than a piece of standard paper, and the bending stiffness of a material is proportional to its thickness cubed. As a dressing is applied, it must often fold onto itself in order to accommodate for a geometrical mismatch between the planar dressing and the contours of the body surrounding the wound to be treated. This creates creases, also referred to herein as wrinkles, in the dressing that have a high potential for causing air leaks into the NPWT system.

Adding to the geometrical mismatch, the dressings often become less adhesive due to the introduction of foreign materials onto the adhesive before dressing application. This is most common and almost unavoidable at the edges of the dressing due to handling by the caregiver. At times, the caregiver's hands introduce enough foreign particles onto the adhesive to forbid further adhesion of that area of the dressing. In the U.S., this often happens when a caregiver uses powdered gloves. This is a critical issue as the edges of the dressing are an area where leak propagation from the edge of the dressing to the wound cavity is potentially very high, based on the theory of interface fracture mechanics.

For the electrical NPWT systems, a thin plastic, adhesive backed dressing is typically used. Electrical NPWT dressing systems have not readily addressed the air leak issues listed above that form at the dressing-to-skin interface. Instead, dressing iterations have focused on air leaks at the tube-to-dressing interface. When NPWT was first introduced into the market, the drainage tube was inserted into the wound cavity through the edge of the dressing. This introduced a high potential for air leaks, which often alarmed the shut-off system. Caregivers began to solve this problem by raising the tube from the skin surface at the dressing edge, and pinching the dressing under the tube before the dressing contacts the skin. This caused the dressing to adhere to itself in an upside-down "T" pattern onto the skin.

Eventually, some of the NPWT dressing, commercial designs incorporated their own solutions to the high air leak rate at the tubing interface. Out of these solutions, the T.R.A.C. Pad by KCI was highly effective, which is driving the current design trends. The T.R.A.C. Pad prefabricates the drainage tube to a semi-rigid, tubing connector, which is then attached to a small, circular, planar adhesive dressing (a.k.a., drape). All of these connections are made air-tight during its manufacture. The tubing does not travel beyond the plane of the adhesive dressing, and therefore its opening remains at the skin surface. When the T.R.A.C. Pad is used, the standard dressing (i.e., wound packing material and adhesive drape) is initially applied to the wound, without a tubing connection. Then, a small incision is made in the dressing, over the wound cavity; this hole may also be prefabricated into the drape component of the dressing during its manufacture. The film backing of the circular adhesive component is removed from the Pad, and the tube opening is centered over the incision. Since the adhesive surface of the Pad is small, it is easier to handle than the procedure of tunneling the tube into the initial dressing. Although the Pad does not guarantee elimination of air leaks at the tube-to-dressing interface, it highly reduces the probable amount of air leaks into the dressing, based on its ergonomic design and small profile. A minimal amount of air leaks is almost unavoidable for all applications with planar adhesive components, due to the geometrical mismatch and user handling that still remain.

Many efforts have been made in order to overcome the identified barriers of low end, mechanical pumps for application in NPWT. Most of the focus has been on reducing air leaks and creating more predictable vacuum sources. New materials used in NPWT dressings have been the main driver in reducing the air leak rate into the system at the dressing-skin interface. These materials are often not new to wound dressings; however, they are new to NPWT. Pump design has been the focus of creating more predictable vacuum sources; mechanical components, such as linear or constant force springs, are often introduced into the system and maintain a more predictable behavior throughout therapy.

Only one mechanical NPWT system is on the market today, but is not widely used: SNaP® Wound Care System by Spiracur (Sunnyvale, CA). The SNaP® Wound Care System uses a hydrocolloid dressing with specific mechanical connectors from the tube to the dressing, in order to accommodate for air leaks; the provided hydrocolloid dressing is relatively small in size. Hydrocolloids are used in many wound-dressing systems, and are a common trend in the NPWT market. They are stiffer and thicker than most common, adhesive, planar, NPWT specific dressings. This causes the dressing to fold onto itself less during its handling and application. However, it cannot accommodate for geometrical mismatch without creases, especially as the dressing surface area increases. Since the dressing is stiffer and thicker, these creases are difficult to seal in an air-tight manner, due to its increased bending stiffness. Therefore, hydrocolloids are often only applicable to smaller wounds. Much effort is currently being taken to make them thinner, in order to increase their applicable surface area and accommodate more for contours, such as the Replicare Thin Hydrocolloid Dressing by Smith and Nephew. Hydrocolloids rely on their extremely sticky adhesive properties to account for increased skin adhesion and reduced air leaks. If they come in contact with wound exudate, the polymers in the hydrocolloid swell with water until saturation, forming a gel, which is held solid in its adhesive matrix structure.

In the SNaP® Wound Care System, the hydrocolloid dressings are connected to the tubing with a mechanical connector component, similar to the T.R.A.C. Pad, KCI. The SNaP® Wound Care System eliminates any potential air leaks from this mechanical connector by prefabricating it to the center of the entire dressing during manufacture. The prefabrication eliminates any potential air leaks at the tube-to-dressing interface due to user interface and geometrical mismatch, but it is not capable of being moved on the dressing surface. Therefore, it may need to be placed on an inconvenient area of the wound, such as a location that is uncomfortable for the patient. Additionally, the tube runs parallel to the plane of the drape; the direction of the tube along the plane of the drape is fixed. Since the dressings are not typically round, the tube path may be required to travel in an undesirable path, in order to cover the wound area with the preset shape of the drape.

For its vacuum source, the SNaP® Wound Care System uses a complex system, driven by constant force springs. Therefore, as the pump expands, mainly due to air leaks and potentially exudate removal, the pressure remains relatively constant for the length of the pressure application. This system is expensive and highly technical when compared to the non-electrical pumps at the low end of the medical pump spectrum (e.g., bladder pumps); however, it is the first commercial mechanical NPWT pump, which has been proven to be a potential NPWT pump design. Since air leaks into the dressing system remain highly probable, depending on wound location and caregiver experience, the successful application of the SNaP® Wound Care System is limited in practice.

Certain known liquid drapes are low viscosity adhesive formulas that are applied, prior to drying or curing, directly to intact skin. One liquid drape is discussed by Zhang et al. in U.S. Patent Publication No. 2010/0112036 A1. However, such liquid drapes are not suitable for application over a wound cavity. Also, such adhesives are not sufficiently elastomeric for use in wound care and have the same wearability restrictions as tape backings.

SUMMARY

Occlusive skin dressings according to the present invention preferably provide one or more of the following advantages:
 a conformable dressing system that can be altered if desired and applied to substantially all areas of the skin surface;
 a dressing system that reduces pain and/or tissue damage upon removal;
 a dressing system that is ergonomic;
 dressings that are easy to obtain and re-obtain by the user, through conveniences in storage;
 a dressing system that minimizes air paths between the outside environment and the wound cavity or incision;
 a dressing system that provides an occlusive barrier;
 dressings, pumps, systems, and methods to administer NPWT without the need for electrical power;
 NPWT systems that are easy to obtain and re-obtain by the user, through conveniences in storage;
 minimizing the amount of air leaks into the NPWT system;
 preventing occlusion of internal fluid paths of the system;
 providing a method of collecting wound fluids;
 detecting air leaks into the NPWT system;
 compatible with light-weight, easily transportable and low cost pumps;
 easy to operate pumps;
 pumps with a deterministic applied pressure or pressure range;
 pumps with a deterministic measurement system for the applied pressure; and
 mechanical methods to minimize the possibility of exsanguinating the patient.

Occlusive dressings according to the present invention overcome the aforementioned drawbacks by being truly air-tight. One principal application of this technology is to facilitate administration of mechanical NPWT. At least three occlusive dressing embodiments are featured: a drape with liquid sealant component; a liquid layered drape with liquid sealant component; and a liquid layered drape. A liquid layered drape is a laminate of adhesive layers constructed without a backing, also referred to as "unbacked". The layers can be transferred to the skin to create a substantially air-tight seal preferably for at least 48 hours, more preferably for at least 72 hours. In some embodiments, a single liquid layer is used in the construction, more preferably at least two liquid layers are used. In some embodiments, the liquid layered drape includes an additional liquid sealant component.

A liquid sealant component preferably is applied at the dressing-to-skin interface of a drape, including some liquid layered drapes, in order to create a substantially air-tight seal preferably for at least 48 hours, more preferably for at least 72 hours. In some embodiments, the same or different liquid component is applied at the tube-to-dressing interface in order to create a similar air-tight seal. In some embodiments, the liquid components is made of rubber polymers applied by touch, by squeezing a dispenser, by transferring with an applicator, and/or by spraying the polymers with an atomization process.

This invention features a kit suitable for occlusively sealing a wound penetrating the skin of a patient, including a drape formed as a thin sheet of an organic, preferably elastomeric material, substantially impervious to fluid transfer of air and bodily fluids, having first and second surfaces. A biocompatible adhesive is at least one of (1) disposed on at least the first surface of the drape, (2) capable of contacting at least a portion of at least the first surface of the drape, and (3) the base material of the liquid drape. When the kit includes the biocompatible adhesive disposed on at least a portion of the first surface of the drape, or is the base material of the liquid drape, the kit further includes at least a first removable liner sheet covering the first surface of the drape. In some embodiments, a second removable liner sheet covers the second surface of the drape, especially when adhesive is also disposed on the second surface of the drape or when the drape is a liquid layered laminate. If a liquid layered drape includes sealant and if the drape is not a liquid layered laminate, the kit further includes at least one container of at least one sealant component that is capable of being delivered as a sealant in a liquid state at pre-selected ambient conditions, the sealant as delivered being at least partially cross-linked at least after one of drying and curing, and which is capable of at least one of drying and curing within thirty minutes, preferably within twenty minutes and, more preferably, within ten minutes, after application of the sealant as a layer to the edges of the drape after the drape is applied to the skin surrounding the wound.

In some embodiments, the drape and the sealant after one of drying and curing are elastomeric. In a number of embodiments, the drape and the sealant are derived from substantially the same material, such as a type of a rubber compound (including natural latex rubber) or a type of silicone compound. In certain embodiments, the adhesive is a silicone-based adhesive and is disposed on at least a majority of each of the first and second surfaces of the drape as a solid coating or in a pattern such as a grid or concentric circles, or is the base material of the liquid drape, as a solid coating or in a pattern such as a grid or concentric circles. In other embodiments, this adhesive is acrylic-based and, in yet other embodiments, it is rubber-based. In certain embodiments, the type of adhesive may also vary between the first and second surface, or within a surface. If a liquid layered drape includes sealant and if the drape is not a liquid layered laminate, at least one container of a sealant component enables manual application of the sealant in some embodiments, such as by squeezing the container and/or using a sponge applicator and, in other embodiments, at least one container is a removable vial or cartridge insertable into a dispensing apparatus or other applicator.

In a number of embodiments, the kit further includes a flexible tube having a first end and a second end connectable to a source of negative pressure such as a bellows, especially a novel bellows which unrolls, or other mechanical vacuum source. In a number of embodiments, the vacuum source includes a carrying strap. Internal and/or external limiters for the vacuum source are present in some embodiments, including at least one of externally limiting compression plates and internally limiting cap projections. In some embodiments, the kit further includes a measurement component to measure the pressure applied by the vacuum source; in one embodiment, this component is a mechanical component, such as a ruler. In some embodiments, the measurement component is incorporated into the carrying strap. Preferably, the kit further includes a flange having at least one of (1) a central passage through which the first end of the tube is insertable and (2) a central passage that is at least one of (i) communicating with a connector capable of mating with the first end of the tube and (ii) capable of communicating with a connector that is capable of mating with the first end of the tube. In one embodiment, a tubing-to-flange connector is included as a separate component in the kit that is capable of mating with a central passage in the flange and the first end of the tube. In one embodiment, the central passage of the flange includes features such as ribs to resist blockage of the fluid path. In one embodiment, the first end of the tube includes a feature such as a spiral cut to resist blockage of the tube.

In some embodiments, the kit includes at least one nonstick handling component. In a number of embodiments, the kit further includes at least one wound packing material. In a number of embodiments, the kit further includes a material to cover the drape and/or sealant; in the preferred embodiment, this is a container of a fine, solid particulate, such as talc powder. In some embodiments, at least one of the kit components is contained in a stackable tray that can be inverted to alternately nest into another tray.

This invention may also be expressed as a method of constructing an occlusive dressing over a wound penetrating the skin of a patient by selecting a drape formed as a thin sheet of an elastomeric material, substantially impervious to fluid transfer, and having first and second surfaces. A biocompatible adhesive is selected that is at least one of (1) disposed on at least the first surface of the drape, preferably with a first removable liner sheet covering the first surface of the drape and (2) applied to at least one of (i) the skin of the patient surrounding the wound and (ii) at least a portion of at least the first surface of the drape, unless the biocompatible adhesive is the first surface layer of the liquid drape, above a selected minimum thickness, and covering at least selected minimum areas of the first surface.

Optionally, a second removable liner sheet covers the second surface of the drape. The method includes removing the first removable liner, if present, and placing the drape onto the skin surrounding the wound, removing the second removable liner if present, and, if a liquid layered drape is selected to include sealant or if the drape is not a liquid layered laminate, also applying a sealant that is in a liquid state as applied at ambient temperature, the sealant being at least partially cross-linked at least after one of drying and curing, on at least the edges of the drape and on the skin adjacent to the drape in one or more layers. The method further includes at least one of drying and curing the sealant within thirty minutes, preferably within twenty minutes, after application of the sealant to the edges of the drape in at least one layer. After at least one of drying and curing of the sealant, the method may further include the application of a material to cover the outer surface of the drape and/or sealant.

When using a sponge applicator to apply the sealant component, one preferred method is to saturate the sponge with a saturation liquid, preferably water or saline, prior to using it to transfer the sealant from the sealant container to the drape and/or skin. This includes soaking the sponge in the saturation liquid and then removing any excess liquid by squeezing or wringing out the sponge.

In certain embodiments, an adhesive is disposed on at least a majority of each of the first and second surfaces of the drape, and/or the method includes pressing on the second surface of the drape in the vicinity of any wrinkles in the drape, preferably before sealant is applied in that vicinity. In some embodiments, a flexible tube is selected having a first end and a second end connectable to a source of negative pressure such as a bellows or other mechanical vacuum source. Preferably, the first end of the tube is at least one of (1) inserted through a central passage of a flange secured to the drape and (2) mated with a connector on a flange having a central passage communicating with the connector.

In one embodiment, the first end of the tube includes a feature such as a spiral cut to resist blockage of the tube. In one embodiment, the central passage of the flange includes features such as ribs to resist blockage of the fluid path. In some embodiments, the wound is packed with gauze or other fluid-pervious material prior to placing the drape on the skin. In some embodiments, at least one of the outer surface of the (1) drape and (2) sealant that is at least one of dried and cured is covered with a material. In some embodiments, the vacuum source is monitored with a mechanical pressure gauge. In one embodiment, the mechanical pressure gauge is integrated into at least one of the tube and pump carrying strap.

This invention may be further expressed as a method of constructing an occlusive dressing over a wound, penetrating the skin of a patient, by at least one of (1) packing the wound with a fluid-pervious material and (2) covering at least a portion of the wound with a protective material. The method further includes applying, such as by spraying or by a saturated sponge applicator, an elastomeric material that is in a liquid state, and is at least partially cross-linked at least after one of drying and curing, over the packed material and/or protective material and onto skin surrounding the wound to create an occlusive drape as a thin sheet substantially impervious to fluid transfer, having a first, inner surface and a second, outer surface. The method includes at least one of drying and curing the elastomeric material within thirty minutes after application of the elastomeric material as a layer. After at least one of drying and curing of the elastomeric material, the method may further include the application of a material to cover the outer surface of the elastomeric material.

This invention may also be expressed as an unbacked, liquid layered tape that has first and second surfaces and is a laminate of at least one adhesive layer constructed without a backing and as a solid coating or, when at least two adhesive layers are included, at least one layer is a solid coating or is in a pattern such as a grid or concentric circles. In some embodiments, the tape is a layered construction of at least two adhesive layers, at least three adhesive layers, or at least four adhesive layers. In some embodiments, the contact adhesive is thicker than 2 mil, in other embodiments it is thicker than 4 mils, and in yet other embodiments, it is thicker than 5 mils. In some embodiments, the tape is wider than 2 inches, in other embodiments it is wider than 4 inches and, in yet other embodiments, it is wider than 6 inches. In some embodiments, the tape is unrolled for use. In certain embodiments, the tape is capable of being utilized as a drape for wound care.

In some embodiments, the liquid layer construction includes a first adhesive that provides at least a first bond strength to the substrate and, in constructions with multiple layers, subsequent layers of adhesives serve to provide at least one of (1) cohesive strength to the laminate, (2) a barrier to prevent pinhole propagation, (3) elastomeric properties, (4) an occlusive barrier, (5) adhesion between layers, (6) a suspension for active or functional agents, components or compositions such as one or more of UV blockers, hydrocolloids, pharmaceuticals, antimicrobial agents, and dyes, (7) structural volume, (8) structural stiffness, and (9) a specific adhesive outer surface. In some embodiments, all adhesive layers are pressure sensitive adhesives.

Some embodiments further include a removable liner sheet covering the second surface of the tape, especially when it is utilized as a drape. In certain embodiments, the construction further includes a first removable liner sheet covering the first surface of the tape, especially if the tape is not unrolled for use. If included, the first liner is removed to expose the substrate contact adhesive, as the second liner is used as a carrier liner. In some embodiments, the second removable liner sheet is removed after the adhesive is adhered to the substrate. In some embodiments, at least part of the outer surface of the tape is covered with a material. In one embodiment, the liquid layered tape and outer surface covering material are included in a kit. In one embodiment, the liquid layered tape is used to protect areas of the substrate. In some embodiments, the liquid layered tape is used to protect areas of the skin. In some embodiments, the liquid layered tape is used to cover a wound. In some embodiments, the liquid layered tape is suitable for use as a wound drape. In one embodiment, the liquid layered tape is used to adhere objects to the substrate. In some embodiments, the liquid layered tape is used to adhere objects to the skin.

This invention may be further expressed as the method of constructing a liquid layered tape, wherein the layers are at least one of (1) coated onto a transfer film, (2) coated over another layer of adhesive that is at least one of dried and cured, and (3) laminated to each other. In some embodiments, the layers are constructed by simultaneously layering the adhesives through a lamination process. In its preferred final embodiment, the layered construction is multiple layered adhesives with at least one removable liner. In some embodiments, at least one of the removable liners is the transfer film that the adhesive was originally coated onto.

BRIEF DESCRIPTION OF THE DRAWINGS

In what follows, preferred embodiments of the invention are explained in more detail with reference to the drawings, in which:

FIGS. 3A and 3B schematically illustrate a novel symmetrical flange and tube connector of FIGS. 1 and 2 being connected to form a symmetrical connector assembly, as illustrated in FIGS. 4A and 4B, with FIGS. 3B and 4B being side cross-sectional views of FIG. 3A and FIG. 4A, respectively;

FIG. 11 shows a hole punched in the dressing of FIG. 10;

FIGS. 12 and 13 shows a tube assembly being inserted onto the dressing of FIG. 11 with the edge of the flange being sealed to the drape;

FIG. 14A shows the adhesive patch of FIG. 2 sealed to the flange and drape of FIG. 13;

FIG. 14B shows an alternative adhesive patch sealed to the drape of FIG. 13 and an alternative novel, preferably symmetrical flange;

FIG. 15 shows a protective liner being adhered to the dressing of FIG. 14B;

FIG. 16 shows the protective liner being removed from the dressing in FIG. 15;

FIG. 17 shows an alternative protective liner adhered to the dressing of FIG. 14B;

FIGS. 18A and 18B show the protective liner being removed from the dressing in FIG. 17;

FIGS. 32A and 32B show an exploded view of a novel cap, with FIG. 32B being a partial cross-sectional view of FIG. 32A;

FIG. 41 shows an alternative carrying strap being applied to an alternative pump;

FIGS. 42A and 42B illustrate the nesting of two kit trays;

DETAILED DESCRIPTION

Figure 1:
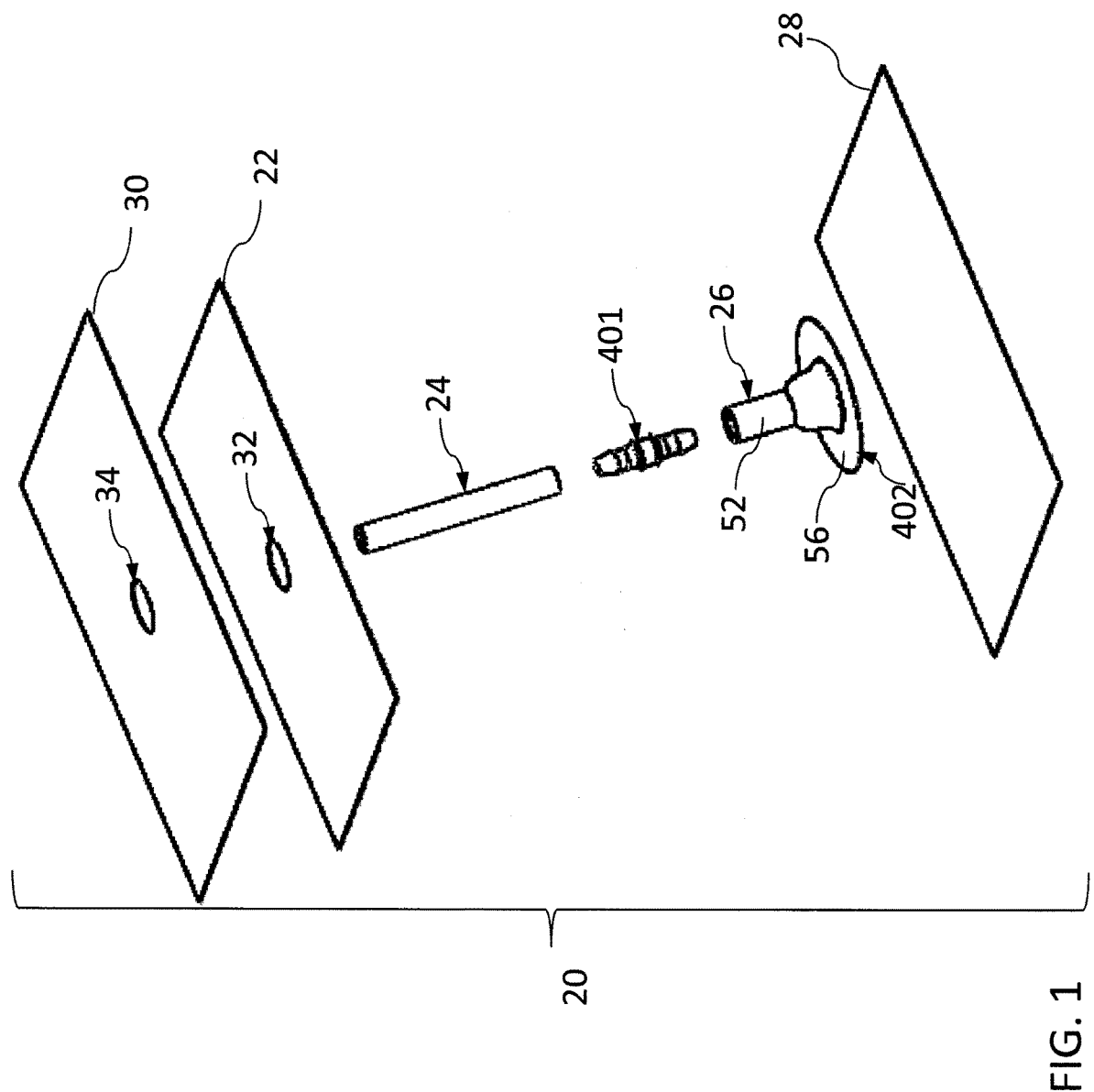
FIG. 1 is a schematic expanded perspective view of a drape, flange, connector and tube kit components with first and second liners, prior to application of a liquid sealant according to the present invention.

Described and claimed herein are novel tapes and methods including an unbacked construction of at least one liquid layer adhesive that has been at least one of dried and cured. Also described and claimed are novel occlusive tissue dressings, tapes and methods including an elastomeric drape and, for backed drapes and some unbacked drapes, a liquid component, at least partially cross-linked at least after one of drying and curing, suitable for application at a dressing-to-skin interface in order to create a substantially air-tight seal. The same or a different liquid component may be applied by a user at a tube-to-dressing interface of an elastomeric drape to create a similar air-tight seal around the tube, if not occlusively sealed during its manufacture.

The occlusive wound dressing aspect of this invention may be accomplished by a kit, dressing system or method utilizing a drape formed as a thin sheet of an organic, preferably elastomeric material, substantially impervious to fluid transfer of air and bodily fluids for preferably at least 48 hours, more preferably at least 72 hours, having first and second surfaces. Preferably, a biocompatible adhesive is disposed on, applied to or contacted with, at least the first surface of the drape or is the base material of the unbacked, liquid drape. In a number of constructions, a first removable liner sheet covers the first surface of the drape and, optionally, a second removable liner sheet covers the second surface of the drape. Preferably, the drape is constructed of at least one layer of an adhesive. In certain constructions, the invention further utilizes a container of at least one sealant component that is capable of being delivered as a sealant in a liquid state at pre-selected ambient conditions, the sealant as delivered being at least partially cross-linked at least after one of drying and curing, and which is capable of at least one of drying and curing within thirty minutes, preferably within twenty minutes and, more preferably, within ten minutes after application of the sealant as a layer to the edges of the drape after the drape is applied to the skin surrounding the wound.

The occlusive dressings presently disclosed address the power/mobility and air leak issues of NPWT by eliminating the need for an electrical power source and by maintaining reliably air-tight interfaces, particularly at 1) the dressing and the skin and 2) the tube and the dressing. The disclosed dressing systems and their connection methods allow for reliable, mechanical NPWT systems. Not only does this eliminate patient mobility and battery management issues, but it also allows NPWT to be administered in austere environments, where electricity is often scarce and harsh environments require robust products. Multiple disclosed embodiments support an inexpensive, robust therapy method for global application. Additionally, dressings according to the present invention are MRI-compatible.

In its preferred construction, the wound drape component according to the present invention has a novel, unbacked liquid adhesive embodiment. It can be manufactured using the same converting processes as utilized to manufacture general adhesive tapes and, therefore, this application discloses the embodiment in the more general sense of a novel, unbacked liquid adhesive tape. One skilled in the art would realize, after reviewing the present application, that this applies to embodiments for many applications, including wound drapes, skin tapes, structural tapes, and fabric tapes.

Adhesive tapes, including certain wound drapes, are typically manufactured conventionally by coating a substantially non-tacky, structural backing with adhesive. The backing can be made of various materials, including paper, woven or non-woven fabric, foil, and polymer film or sheet. These backing materials often limit the extensibility and elasticity of the tape, as detailed in U.S. Pat. No. 4,024,312 by Korpman. During the conventional tape manufacturing process, the backing is typically sourced in a roll that is then unrolled and coated with an adhesive on at least one of its sides. The backing manufacture/rolling and unrolling/coating processes often occur in two different facilities. In some embodiments, the adhesive may be further protected with a removable liner (a.k.a., release liner). The removable liner is typically applied after the adjacent adhesive did at least one of at least partially (1) drying and (2) curing on the backing. The final, layered material (i.e., backing, adhesive, and removable liner, if used) is typically rolled for further processing.

If no removable liner is used and only one surface of the backing is coated with adhesive, a conventional release coating is often applied to the backing on the opposite side of the adhesive, in order for the tape to easily be unrolled during further processing and/or its functional use. If adhesive is applied to both sides of the backing, a removable liner is typically applied to at least one of the adhesives; if only one release liner is used, this liner typically has a release coating on both sides for its release of both adhesives: one upon unrolling the tape and one as the liner is removed. In this conventional case, the bond of the release liner to the two adhesives must have a bond strength differential large enough between the two adhesives in order to properly be unrolled and then removed during its use. It must have a lower bond strength to the first adhesive that is removed from the liner during the unrolling process. The liner is typically removed from the second adhesive after the first adhesive is applied to a substrate. Therefore, in this conventional case, the liner must have a lower bond strength to the second adhesive than the bond strength between the first adhesive and the substrate that its attached to. During its functional use, the adhesive (on one or two sides of the backing) and the backing form the functional tape embodiment.

The preferred functional tape embodiments according to the present invention are not made with a traditional, substantially non-tacky backing, as described above for conventional manufacturing processes. In one preferred embodiment, at least a portion of a transfer film is coated with a liquid polymer layer and at least one of at least partially (1) dried and (2) cured. The phrase "at least a portion" is coated includes patterns of liquid polymer layer, such as concentric circles or a grid of "dots" or lines. Then, a second liquid polymer layer may be directly coated over (i.e., in liquid form and allowed to at least one of at least partially (1) dry and (2) cure) or laminated to (i.e., laminated after the second liquid polymer at least one of at least partially (1) dries and (2) cures on a transfer film) at least a portion of the first layer. Sequential layers may be added thereafter, for which a transfer film may need to be removed, in order to expose at least a portion of a polymer surface for coating or laminating. To aid in the drying and/or curing process, the layered constructions may be placed in different environments. For example, one or more of the following techniques can be utilized: heat may be applied to the liquid layer; particularly for hot melts, the layer may be cooled; radiation may be applied; or the process may require a combination of processes in parallel or sequentially.

In some techniques according to the present invention, the lamination process may include the lamination of a transfer film, with no additional polymer. For the final construction, the transfer film on at least one of the top and bottom of the final layered construction is not removed and takes the functional form of the removable liner previously discussed, and/or the transfer film on at least one of the top and bottom of the final layered construction is removed and replaced by a removable liner. One skilled in the art would realize that the individual layering of materials does not have to happen sequentially, and that subassemblies of layered constructions can in-turn be laminated to each other. This technique may be desirable to separate the processing temperatures and times of the subassemblies. One skilled in the art may consider certain final constructions to be a combination of layered adhesives. With this definition, each final construction must have enough cohesion in at least one layer to provide a functional construction that maintains cohesion throughout its functional use.

One preferable method of construction is to coat each liquid polymer layer onto a transfer film and then sequentially laminate the polymer layers into the final assembly or separate subassemblies. After the individual layers are initially coated onto a transfer film, they are typically rolled (i.e., for transport or storage) after the polymer layer does one of at least (1) drying and (2) curing; therefore, in the preferred embodiment, the transfer film has a release surface on both sides, such that the layer can be unrolled and the transfer film removed. Otherwise, a second transfer film would need to be applied to the polymer layer before rolling it.

Initially, for each assembly or subassembly, a base liquid polymer layer may be first laminated onto another transfer film and its original transfer film removed, or in the preferred process, it is used with its initial transfer film. Each layer (i.e., individual layer or subassembly of multiple layers) is laminated sequentially to another layer, and then, one of the transfer films of the resulting embodiment is removed prior to its next lamination step, in order to expose the polymer to be laminated. During the process, a lamination step may be used to laminate a layered construction to a new transfer film, during which no new liquid polymer layers are added. This may be done in order to create the necessary bond strength between the transfer film and its adjacent adhesive; for instance, a film with a weak bond strength may be replaced with a film with a stronger bond, in order to peel the film from the opposite side of the laminate. In addition, in the case that a subassembly or final assembly is rolled (i.e., for transport or storage) and one of its transfer films is removed, the remaining transfer film must have a release surface on both sides, such that the subassembly or final assembly can be unrolled and the transfer film removed in the future.

If at least one of the top and bottom polymers is attached to a removable liner in the final functional construction, one or more final removable liner(s) can be laminated onto the final construction during the conversion process, or the original transfer film(s) of the final laminate can be used as the removable liner(s). An example of a case where a new liner would be introduced is if the desired removable liner could not be used in the individual layer coating process onto a transfer film, due to heat sensitivities or bond strength issues. This may also be the case when the original base transfer film is needed for its stronger bond strength to the base layer during the stripping of subsequent transfer films during the lamination process, however, after the layering is complete, a different base removable liner is preferred in the final embodiment. In this case, the top transfer film would need to have a strong enough bond to the laminate for the base (i.e., bottom) transfer film to be removed and replaced with the new removable liner. If only one removable liner is used and if the laminate is rolled onto itself, the removable liner must have a release surface on both sides, such that the laminate can be unrolled and the liner removed, as previously discussed. In one preferred embodiment, a removable liner is on an least the side of the laminate opposite the side first attached to a substrate during functional use. This allows the tape to be easily handled during its functional application. If two removable liners are used, the base and top liners in the final embodiment should have the proper bonding strength differential for functional use of the dressing. For instance, if the base liner is to be removed first, it should have less bonding strength during its removal. Transfer film and removable liner bond strengths can be varied by peel angle and set time, during lamination and functional use.

During manufacture and use of this layered embodiment, the bond strengths between all of the adjacent polymer layers are ideally larger than the bond strength (a.k.a., adhesion or adhesive strength) of any transfer film or removable liner to its adjacent polymer during its removal. If two transfer films or removable liners are used to sandwich at least one polymer coating during manufacture or use, respectively, the film or liner that is to be removed first should have less bond strength to its adjacent layer during its removal than the film or liner to be removed second. This allows for the films or liners to be easily removed without delaminating any other interface. In some embodiments, a transfer film or removable liner is removed by pulling the film or liner with at least one of a specified (1) angle and (2) speed, or within a range of specified (1) angles and (2) speeds, in order to reduce the effective bond strength of the film or liner to the adjacent layer and create the necessary bond differential for removal (this variable adhesive strength (i.e., peel force) vs. peel angle is described when peeling tape off of a substrate in U.S. Pat. No. 5,516,581 by Kreckel et al.; peeling the film or liner off of the polymer layer or laminate adheres to the same mechanics principles). Although it is not preferable, selected environmental conditions such as temperature can also be varied to vary the peel force differential between layers. Additionally, the bond strength of an adjacent liquid polymer to the film or liner typically increases over time before reaching its maximum value. Therefore, temporary liners during the lamination process may be used in a time dependent manner.

The layers each need the proper adhesion-cohesion balance, in order to provide the proper adhesive strength to the adjacent layers or desirable substrates and the proper cohesive strength for the desired mechanical performance properties. In the preferred embodiment, the liquid layers are adhesives (i.e., after at least one of at least partially (1) drying and (2) curing, all viscoelastic liquids, all viscoelastic solids, or a mixture of viscoelastic liquid and solid layers), and therefore, since they are viscoelastic, they possess the characteristics of both liquids and solids. In the preferred embodiment, they are all coated in liquid form onto transfer film prior to any lamination processes. In one preferred embodiment, all of the layers are pressure sensitive adhesives (a.k.a., PSAs), and are manufactured using at least one of (1) solvent, (2) hot melt, (3) emulsion, (4) radiation, (5) suspension, and (6) other solution processes. The transfer film provides the mechanical structure necessary for the rolling and unrolling processes and for any lamination processes. With the proper balance of adhesion and cohesion, an unbacked construction of liquid layers according to the present invention may be transferred onto a substrate with a removable liner, and embody the functional properties of a typical tape laminate of at least one adhesive layer and backing layer. However, based on the present invention, mechanical properties of the present tape embodiment can be achieved, which are not possible by laminating a typical backing layer. Materials that are difficult to handle or infeasible to make in the standard backed embodiment may be fabricated. One skilled in the art would realize that the liquid layer construction may also be used as a component in other assemblies, such as border dressings.

One benefit of this tape embodiment with a liquid construction method according to the present invention is that it can use more desirable materials for enhanced functional performance, compared with the standard backings readily available today. Additives to the materials can be easily mixed into the liquid formulation prior to its layer application, in order to alter the properties of the final embodiment and fabricate tapes from custom materials. Elastomeric materials are ideal, although plastic and elastomeric materials may be used. At least one layer of rubber, such as a polyisoprene rubber (IR) based or natural rubber latex based formulation, may be preferred, due to its desirable elastomeric properties for this invention. In some embodiments, the liquid layers may suspend addition components, such as: pharmaceuticals, antimicrobials, hydrocolloids, UV protectant, alginates, and dyes. Based on the liquid coating process for each layer, these are easily integrated into the design.

In one preferred embodiment of this invention, two layers are sandwiched between two removable liners. First, a liquid rubber adhesive (i.e., a synthetic, natural, or synthetic-natural hybrid rubber; preferably an emulsion) is coated onto a transfer film/removable liner that it adheres to upon at least one of at least partially (1) drying and (2) curing. The final rubber embodiment is cross-linked such that it has a low rubber modulus, allowing for easy stretch-ability (i.e., high extensibility), and a high elastic recovery. Preferably, the elastic recovery from 50 percent stretch is at least 75%, and more preferably at least 90%, and even more preferably at least 95%. The material properties are discussed in further detail below.

The final rubber embodiment is a solid viscoelastic material layer that is tacky on both of its surfaces. One skilled in the art would commonly refer to this layer as an adhesive layer. This highly elastic layer would be very difficult, if not impossible, to handle as a traditional backing roll. Rubber emulsions are often tacky, and therefore, they cannot easily be rolled onto themselves without processing steps to remove the tack. For example, coating the material with a powder and/or liquid sealant can remove the tack, which would alter the ability to coat or laminate the rubber directly with adhesive, as the powder and/or sealant would need to be removed first. In addition, the easy stretch-ability of this layer makes it difficult to handle without a stiff backing layer of its own attached for processing, in this case the transfer film/removable liner allows for easy handling, including the rolling and unrolling processes.

The rubber layer coated onto a transfer film/removable liner is coated or laminated with a second functional pressure sensitive adhesive (PSA). In this case, the initial rubber layer is used mostly for its cohesive strength and the second PSA is used for its functional adhesive strength. In the preferred embodiment, the second PSA is laminated to the rubber, after the PSA is coated onto a transfer film/removable liner. In a preferred embodiment, the second PSA is a silicone-based adhesive. In another preferred embodiment, the second PSA is an acrylic-based adhesive, including a modified acrylic adhesive. In another preferred embodiment, the second PSA is a rubber-based adhesive. Pressure sensitive adhesives that may be used in this embodiment include tackified rubber adhesives (i.e., natural rubber, olefins, silicones, polyisoprene, polybutadiene, polyurethanes, styrene-isoprene-styrene and styrene-butadiene-styrene block copolymers) and other elastomers; and tackified or untackified acrylic adhesives (i.e., copolymers of isooctylacrylate and acrylic acid, which can be polymerized by radiation, solution, suspension, or emulsion techniques, including vinyl ethers and ethylene-vinyl acetates (EVA/PVAs)). Crosslinked adhesives may be preferred, especially those pressure-sensitive adhesives crosslinked to give higher shear strengths (a.k.a., cohesive strengths). Adhesives with a high peel adhesion to the end substrate may be preferred, due to high bond strength.

The second PSA adhesive adheres to the rubber layer after at least one of a (1) lamination process and partially (2) drying and (3) curing. A protective, removable liner is preferably applied to both sides of the adhesive layers by leaving the transfer film on each side from the original adhesive coatings or by laminating a new removable liner onto the surface. If the construction is made by coating multiple adhesives on top of one another, without lamination, then a second removable liner needs to be laminated on top of the layered embodiment. In this case, it should be noted that the manufacturing of the layers may be in the opposite sequence: coating a second removable liner with the second PSA functional adhesive and coating the second PSA with the rubber adhesive and then laminating the layered embodiment with a first removable liner.

In certain tape embodiments under the scope of this invention, a specific manufacturing sequence may be necessary, depending on any required heating or cooling processes and/or the necessary adhesion strength and cohesion strength of each layer and/or UV curing process. For instance, a high temperature may create too strong of a bond between the desired removable liner and its adjacent layer, yet the layer may require that temperature for at least one of (1) drying and (2) curing. Therefore, the layer must be first coated onto a transfer film prior to its removal and the lamination of the desired removable liner, or it must be coated directly onto its adjacent adhesive prior to the application of the desired removable liner. In another instance, the bond strength required between two adhesive layers may require a coating process of one adhesive directly onto the second adhesive, or may require a primer coating to be applied to one adhesive for a stronger bond strength when laminating the two layers. In another instance, the application of heat may continue to strengthen the bond between a desirable transfer film/removable liner and its adjacent layer, which might not be ideal. Therefore, if heat is necessary to at least one of (1) dry and (2) cure subsequent layers, those layers must be at least one of (1) dried and (2) cured before being layered to both the adjacent layer of the desirable transfer film/removable liner and the desirable transfer film/removable liner. In one preferred manufacturing process, each layer is sequentially laminated to the construction. Therefore, the adhesion and cohesion of each layer of the current construction must be able to withstand the removal of the transfer film currently being removed, until the final embodiment is achieved. Although heating and/or cooling may be applied during lamination, it is not preferred. Also, the coating of primers directly onto the coated adhesive layers for increased adhesion is not preferred.

The previously described, preferred embodiment (i.e., rubber layer and second PSA laminate) may be used to make highly extensible tape that can adhere to highly extensible substrates without delamination (due to the high elasticity of the rubber layer, the high adhesion of the second PSA to the substrate, and the strong bond between the adhesive layers). The adhesion of the PSA to a substrate (a.k.a., adherend) depends on many variables, including the ability of the adhesive to wet (i.e., flow onto) the substrate, the ability of the adhesive to resist flow when stress is applied, and the strength of the molecular forces involved in the resulting bond. The PSA tape typically bonds to a substrate with Van der Waals forces, which contribute significantly to the ultimate bond strength and also depend on the proper wetting of the surface. The ability of Van der Waals forces to provide adequate bond strength is based on the material and thickness of each layer of the tape. Typically, the thickness of each layer of material is constant.

Theoretically, for tape (in general) to remain adhered to the substrate, the debond toughness (strength of the bond) must be greater than the debonding energy, and the debonding energy is proportional to: the thickness of the material, the strain in the material squared, and the elastic modulus of the material. Specifically (on a first order basis; as its basis is a small strain analysis), the bond strength of a thin film must abide by Equation 1, where $\Gamma$ is the debond toughness, $\zeta$ is the debonding energy, $\Omega$ is a dimensionless prefactor, which depends on the crack pattern, h is the thickness of the film, $\varepsilon_T$ is the strain in tension, and $E_f$ is the elastic modulus of the film, in order to maintain adhesion to the skin in tension:

$$\Gamma > \zeta = \Omega h \varepsilon_T^2 E_f \qquad (1)$$

Equation 1 shows the debonding energy for a homogeneous, isotropic, a linear elastic, thin film layer, and an infinitely thick substrate. More specifically, Equation 1 is based on small strains, and therefore, should only be used on a first order basis for the function of highly extensible tapes. For the application of a multi-layered tape, the debonding energy, $\zeta$, is dictated by Equation 2. This equation also assumes homogeneous, isotropic, linear elastic, thin film layers, an infinitely thick substrate, and small strains; therefore, it should be used on a first order basis for highly elastic tapes on thick substrates. The energy released per unit area of the tape is:

$$\Gamma > \zeta = \Omega \varepsilon_T^2 \sum_{1}^{n} h_{f_n} E_{f_n} \qquad (2)$$

where $\Omega$ is a dimensionless prefactor, which depends on the crack pattern, $h_{f_n}$ is the thickness of the nth film layer, $E_{f_n}$ is the elastic modulus of the nth film layer and $\varepsilon_T$ is the strain in tension. Therefore, tape with the same bond strength (i.e., same contact adhesive and substrate properties, including the bond between them) will remain bonded during increased strain deformations, as the thickness of its layers decrease and/or the modulus of its layers decrease. This broadens the use of a highly elastomeric tape embodiment with thin, highly elastic layers, and it highly favors the liquid construction layers in this invention and their corresponding mechanical properties over the properties achievable with standard coated backing materials. Note that we assumed a perfect, permanent bond between the construction layers for this first order analysis.

The construction layers in the current invention can reach minimum thicknesses and minimum moduli when compared to tape embodiments that currently exist. This is due to the elimination of the solid backing. Instead of a solid backing, a liquid layer with enough cohesive strength for functional use is used. Through experimentation, natural or synthetic rubber adhesives were suitable for this function in the layered construction. With a completely liquid tape, the superior extensibility of rubber or another highly extensible, elastic liquid-applied polymer is typically the limiting modulus (i.e., increasing the debond energy the most with strain), as the rubber layer typically has the highest modulus. In addition, the liquid layers can often be applied much thinner in a coating process than a typical, solid backing can be made.

In addition to usability, another additional benefit of such a low modulus, highly extensible tape is its removability from the substrate. In the preferred embodiment previously described (i.e., rubber and PSA laminate), the linear elastic modulus (in the linear elastic region) can be much lower than is currently available in tapes, the knee of the stress versus strain curve can be much lower, and in some cases, the moduli through large deformation after the knee can be lower. As the user pulls on the tape for removal, the tape has a large deformation with a low force. In a general theoretical analysis, stretching the tape is storing energy in the tape that is used to break its adhesive bond to the substrate. The substrate will also deform to store energy that is used to break the adhesive bond. The stored energy of the tape and the substrate is equivalent to the area under their corresponding stress versus strain curves that define the mechanics of the deformation.

In order not to tear, deform, delaminate (in the case of paint on a wall or skin, for instance), or otherwise undesirably alter the substrate material, a tape that has a lower, preferably much lower, modulus throughout its deformation than the substrate is desirable; the knee in the stress versus strain curve for the tape is preferable to occur at a low stress compared to the substrate knee and/or yield point, and the tape must have the necessary elongation before break to be removed from the substrate. During experimentation of the preferred embodiments, the user may re-grip the tape closer to the substrate, in order to maintain their grip within a feasible and controllable distance from the delamination fracture line. In addition, a thinner tape and thicker substrate is desirable, in order to increase and decrease, respectively, the applied stress corresponding to an applied force; ideally, the maximum force applicable to the tape during its use is not damaging to the substrate. Therefore, it is desirable for the tape to store most of the energy, especially when more delicate and fragile substrates are adhered to. In addition, keeping the substrate constant, an adhesive with a higher adhesive strength to the substrate can be used with the same impact on the substrate upon removal, if the tape stores the additional energy needed to break the higher adhesive bond. Therefore, lower linear modulus, lower knee stress, large elongation with lower rubber moduli, and thinner thickness of a tape all contribute to the ability to use a contact adhesive with a stronger adhesive force to the substrate with the same impact on the substrate upon removal. The current patent application describes a technology that may allow aggressive adhesives (i.e., high bond strength) to be used in tapes for certain substrates, which are not currently capable of being used in tapes for those substrates.

As described in U.S. Pat. Nos. 4,024,312 and 5,516,581, the removability may vary with the angle of removal, based on adhesive strength variability with the peel angle. Therefore, a tape embodiment with at least one of lower linear modulus, lower knee stress, large elongation with lower rubber moduli, and thinner thickness also contributes to the ability for a user to be able to vary the angle of removal of a tape with a specific adhesive, without damaging the substrate. This may increase the usability and human factors of the tape and may decrease instances of improper use. The contact adhesive is preferably highly extensible, does not separate from the lamination during stretching, and has higher cohesion than adhesion to any suitable substrate.

After being applied to a substrate, the adhesive tape of the present invention becomes firmly bonded, but can be easily removed without damaging the substrate by simply stretching it. In general, stretchable tapes provide a low debonding force from the surface of a substrate at low angles by simply stretching the tape. Since the tape described in this embodiment is highly stretchable, the force of removal may be in any direction. However, in order to minimize the force, it may be preferable to apply the force less then 90° to the surface of the substrate and more preferably parallel, i.e., less than about 45°, to the surface of the substrate. Tensile strength at break should be sufficiently high so that it will not rupture prior to the removal, and therefore, the tape can be removed in one piece. A low Young's modulus is preferable. If the modulus is too high, it is very difficult to stretch the tape sufficiently to cause clean release upon stretching. In the preferred embodiment, the tape typically forms into a polymer ball after it is removed, similar to a ball of rolled rubber cement. This ball is due to the adhesive and elastic properties of the layered tape embodiment.

One preferred application of the preferred tape embodiment described of a low modulus, highly extensible rubber and PSA laminate is in tissue tapes, particularly for the surface of the skin. A lower linear modulus, lower knee stress, large elongation with lower rubber moduli, and thinner tape thickness increases its wearability, as the tape easily stretches with the skin, while maintaining its adhesive bond. For many uses of skin tape, this may allow free mobility of the user with a reduced sense of the applied tape, increasing user comfort. With the rubber and PSA laminate, the linear modulus, rubber moduli at specific strains, and knee stress can be reduced by an order of magnitude compared to current tape embodiments; this is a key factor in its increased wearability and comfort.

An additional benefit of a lower linear modulus, lower knee stress, large elongation with lower rubber moduli, and thinner tape thickness is that the wear time of a particular contact adhesive may increase. For instance, secreted body fluids over time may decrease the debond toughness, which can cause the tape to delaminate from the surface of the skin as the person moves, on a first order basis according to Equations 1 and 2 above. However, with a decreased modulus and/or thickness, the debonding energy of the tape deformation is significantly reduced, allowing for good adhesion through a higher magnitude of decreased debond toughness.

In addition to wearability and comfort, tissue tapes preferably do not cause pain for the user upon removal. Pain typically originates from the deformation and/or damage of the tissue (i.e., substrate), as the tape is removed. Therefore, as previously discussed, the rubber and PSA embodiment can reduce the deformation of the tissue upon tape removal, which may reduce the feeling of pain and/or damage to the tissue, such as skin tears.

Using the disclosed tape technology, this technology disclosure is further in the field of wound dressings with an adhesive film embodiment, which is used to cover a wound (i.e., wound drape component). Below is the description of a preferred wound dressing with the preferred tape embodiment previously discussed (i.e., rubber and PSA laminate). Although natural rubber adhesive may be used, synthetic rubber adhesive is a preferred material in many cases. Synthetic rubber material typically does not have a carbon-to-carbon backbone that can leave it susceptible to ozone, UV, heat and other ageing factors. Synthetic rubber materials also generally come with good levels of chemical and temperature resistance, depending on their formulation. They also typically do not have proteins, which cause contact allergies.

The dressing linear modulus, knee of the stress versus strain curve, and thickness play important roles in the application of the wound dressing. When applying the dressing, the user must apply a planar, flexible dressing onto the skin surface that is typically not planar. Therefore, the user must maneuver the dressing to match the contour of the skin upon its adhesive application. During this process, the user may bridge skin contours, skin wrinkles, and/or folds in the skin. Once applied, the only ways to create skin adhesive contact on areas of the skin that were bridged is (A) for larger bridges: (1) to remove the dressing and reapply it, trying to avoid any bridging during the second dressing application, or (2) to apply pressure on the drape over the bridge to stretch the drape and adhere it to the skin underneath, and (B) for smaller bridges: (3) to wet the surface with the skin contact adhesive.

For the first solution, it is often not ideal to remove and reapply the dressing, as the skin adhesive will remove dead skin cells and other debris from the skin's surface and adhere to particles in the atmosphere. With these particles bonded to the skin contact adhesive, the skin contact adhesive bond is less strong during dressing reapplication to the skin's surface.

For the second solution, a lower effective modulus (and depending on elongation, a lower stress for the knee of the stress versus strain curve) of the dressing is ideal, as a tensional strain is applied to the dressing during the application of pressure and a higher modulus further increases the debonding energy of the dressing, according to Equation 2 on a first order basis. Hence, with this solution, there is a residual force against the bonding force of the skin contact adhesive to the skin. Increased thickness also increases the debonding energy of the dressing when a tensional strain is applied, according to Equation 2 on a first order basis. However, the thickness of thin film dressings are often on the same order of magnitude, and therefore, the linear modulus and potentially the knee of the stress versus strain curve subsequently play a larger role in delamination of the dressing from the skin in many embodiments.

For the third solution, the wetting of the skin contact adhesive often corresponds with the adhesive bond strength. Therefore, the wetting properties of the adhesive are typically limited by the ability to remove the dressing without causing pain or tissue damage to the patient. In practice, the bridges are often not completely removed from the dressing, due to the remedies available and the desired end function. For the reasons stated above, the dressing technology presented in this patent application can allow for more, if not all, bridges to be further resolved during application and wear, creating a sealed wound environment.

As previously discussed, the modulus, knee stress, rubber moduli through large deformations, and thickness also directly affect dressing function and wearability. As the modulus of the dressing and effective thickness increase, the skin adhesive bond strength to the skin must also increase, in order to stay on the skin and prevent delamination during body movements (i.e., applied strains). In addition to adhesive function, the patient comfort and dressing wearability increases with decreasing modulus and thickness. This is because the surface of the skin underneath the dressing moves with less resistance from the dressing with a lower dressing modulus and thickness; this puts less trauma on the skin surface over time, as the shear force of the skin adhesive to the surface of the skin is also reduced. Minimal dressing thickness also decreases the bending stiffness of the dressing, further increasing comfort and wearability. These characteristics favor the current invention embodiments over current commercial wound dressings.

When the dressing is removed, it is ideal for the fracture surface to be the surface between the skin adhesive and the surface of the skin. This is based on the balance of cohesion and adhesion of the materials in the tape and the substrate, which strongly relate to their mechanical properties (i.e., modulus throughout its deformation; the knee and/or yield point in the stress versus strain curve, and the elongation before break), as previously discussed. For some wound dressings, the fracture surface may be in the layer of the skin adhesive or between the surface of the skin adhesive and the backing material; in these cases, an adhesive residue is left on the skin, which is typically removed prior to another dressing application. In the preferred embodiment, the cohesion of the dressing layers and the adhesion between layers allow for the dressing to be removed with no residue left behind. A dressing that causes tissue failure (i.e., fracture in the substrate) upon removal is not desirable.

Prior to the formation of the fracture surface, a force must typically be applied in removing the dressing. The force is typically applied when the dressing is peeled off manually by the caregiver. As previously discussed, the modulus, knee stress, rubber moduli through large deformation, and thickness play a key role in the removal of the dressing. Pain typically originates from the deformation of the tissue, as the dressing is removed. Therefore, as previously discussed, an embodiment with a lower elastic modulus, lower knee stress, large elongation with lower rubber moduli, and thinner tape thickness can reduce the deformation of the tissue upon tape removal, which may reduce the feeling of pain and damage to the tissue, such as skin tears. The rubber and PSA laminate disclosed in this application describes such an embodiment that reduces pain upon removal, which has been proven for wound dressings in both the lab and clinical settings (see U.S. Provisional Patent Application No. 62/090,350 filed 10 Dec. 2014 by the present inventor). As the linear modulus, knee stress, thickness, and/or potentially the rubber moduli during large deformation decrease, the skin adhesive bond of a particular adhesive effectively increases during functional wear, according to Equations 1 and 2. Additionally, as the linear modulus, knee stress, thickness, and/or potentially the rubber moduli during large deformation decrease, the skin adhesive with an increased bond strength to the skin can be used, while maintaining the same or increasing patient comfort level and maintaining the same or decreasing tissue effects upon removal.

An application of the current tape invention may be applied to wound dressings that are highly flexible, in order to aid in dressing application wettability, increase wearability and comfort, and reduce tissue deformation and trauma upon removal. Preferably, the dressing is made of at least four layers. The first layer is a removable liner (i.e., carrier liner), onto which a second layer of an elastomeric organic polymer adhesive (preferably a rubber emulsion) is coated or laminated. Organic in this case means that the material contains carbon. After at least one of (1) drying and (2) curing, the rubber layer is coated or laminated with a skin contact adhesive layer, preferably a silicone, acrylic, or rubber-based polymer, which is protected with a final removable liner that is directly coated with the skin contact adhesive or that is laminated to the skin contact adhesive.

The wound dressing embodiment of rubber and PSA laminate described in the present application is tacky on the surface away from the skin, after the dressing is applied to the skin and its carrier liner is removed. As referenced in the parent application, now U.S. Pat. No. 9,173,777, this property can assist in pressing down the folds on top of the wound dressing, which form due to the geometrical mismatch of the wound dressing and the skin surface. As described in U.S. Provisional Patent Application No. 62/090,437 filed 11 Dec. 2014 by the present inventor, the dressing technology described in this embodiment was effective as a reliable, occlusive wound dressing (handmade in small batches) when combined with a liquid sealant in the clinic; the sealant technique is further described in U.S. Pat. No. 9,173,777. The dressing described in U.S. Provisional Patent Application No. 62/090,350 filed 10 Dec. 2014 coats multiple liquid layers of rubber emulsion directly onto each other after each previous layer at least one of (1) dried and (2) cured, prior to applying one or two layers of skin contact adhesive after each previous layer at least one of (1) dried and (2) cured. In most cases, the adhesive was coated onto the rubber layers bedside in U.S. Provisional Patent Application No. 62/090,350, and in these cases, a protective removable liner over the adhesive was not applied. After the final dressing was applied, the tacky outer surface of the dressing was covered in powder, in order to prevent the outside of the dressing from sticking to other surfaces and to decrease the coefficient of friction between the dressing and any other surface during its wear time.

Further material selection was pursued beyond the work presented in U.S. Provisional Patent Application No. 62/090,350, in order to enhance the mechanical and chemical properties of the occlusive wound dressing and its manufacturability. In result, the rubber and PSA laminate was able to be applied reliably air-tight to the skin, often without an additional sealant (although sealant is used in the preferable embodiment, for reliability of occlusive properties for all skin types, body locations, and wear times). This was due to increased wettability during the dressing application and post application (i.e., by pressing the dressing into any bridges) processes, due to the high elasticity of the layered embodiment. In addition, the increased adhesive (i.e., wetting and adhesive bond), liquid (i.e., viscous), and elastic (i.e., lower modulus) properties of the laminate allowed any air paths to close completely upon user-applied compression force; as the required force decreases, the user reliability increases in closing off any air-paths. One factor that increased this reliability was using a thicker, more tacky skin contact adhesive, preferably above 4 mils.

In addition to a new skin contact adhesive with a stronger bond to the skin, the rubber materials in U.S. Provisional Patent Application No. 62/090,350 were replaced, in order to eliminate proteins; therefore, a synthetic rubber-based adhesive was used. With this material selection, extended wear times encountered an additional issue with the rubber and PSA laminate used, based on their cohesive properties. Pin holes began to form during extended dressing wear, particularly at locations where the substrate significantly changed mechanical properties, such as between the skin, gauze, and tube flange. These pin holes propagated through the dressing, causing air-leaks over time. This pin hole issue in thin films is often seen in the film packaging industry, the fuel cell industry, and in large balloons. In the NASA Tech Brief ("Multi-Layer Laminated Thin Films for Inflatable Structures"), it is suggested that for inflatable structures, a multi-layered laminate will reduce the occurrence of pinholes over a monolayer film. During our experimentation, this was also proven to hold true for tape laminates in the current invention.

One preferred embodiment for an occlusive wound dressing was an eight layer laminate with a 4 mil skin contact adhesive laminated to 2 mil of rubber adhesive, laminated to 1 mil of acrylic adhesive, laminated to 2 mil of rubber adhesive, laminated to 1 mil of acrylic adhesive, laminated to 2 mil of rubber adhesive, laminated to 1 mil of acrylic adhesive, laminated to 2 mil of rubber adhesive. This broke-up an 8 mil rubber layer, which provided enough cohesion to provide the structural integrity of the tape, into 4 layers. This resulted in similar mechanical properties, but reduced the probability of any pinhole propagation through the multiple laminate layers. The new dressing embodiment remained occlusive during five day wear in our in vitro experimentation; the contact adhesive on the dressing adhered to skin, gauze packing, and the tube flange. In this new embodiment, it is preferable to have a higher number of layers for the same thickness of material, as long as the thickness of each layer of material achieves its mechanical integrity during the coating process. However, this must be balanced with the time to coat and laminate each layer and the corresponding expense. Also, the adhesion between layers must also remain intact during wear. The manufacturing of a multilayered liquid tape embodiment for a wound dressing is the same as that previously discuss for tape in-general. This multilayered liquid laminate has uses outside of wound dressings in the tape industry, where pinholes are not preferable. Pinholes may propagate into large tears over time, and therefore, they should ideally be avoided in any tape application. Increasing the number of layers of the layers beyond the contact adhesive is ideal to solve the pinhole issue. These new layers should alternate in materials, where an added liquid layer/material may be necessary, in order to stop propagation.

In order to obtain an air-tight skin dressing, the present occlusive dressings preferably use a liquid sealant; this liquid sealant must be utilized if the liquid layered drape embodiment, previously discussed, is not used. This liquid sealant may dry and cure fast, even immediately or effectively immediately, upon application to the skin or other dressing components, into a continuous, occlusive film or sheet of material. The drying and curing processes may occur simultaneously, may be driven by evaporation, may require a curing agent and/or accelerator, and/or may be enhanced or controlled with a curing agent and/or accelerator. Any extra additives (e.g., curing agents and accelerators) may be added just before, during, and/or after the sealant application process, depending on its chemical reaction with the sealant and its rate.

The liquid sealant bonds to the component(s) that it is meant to seal. The ability of Van der Waals forces to provide the bond strength without an added adhesive or other primer (for example, Skin-Prep by Smith and Nephew, London, U.K.) is based on the material and its thickness. Theoretically, the debond toughness (strength of the bond) must be greater than the debonding energy, and the debonding energy is proportional to: the thickness of the material, the strain in the material squared, and the elastic modulus of the material. Specifically (on a first order basis; as its basis is a small strain analysis), the bond strength of a thin film must abide by Equation 1 above. Therefore, a highly elastic, thin film presents the ideal material properties for reduced, required adhesion strength, increasing the functional applicability of the Van der Waals forces.

An additional adhesive, such as a silicone-based, rubber-based (including natural latex rubber), or acrylic-based glue, having one or more components, might be employed to produce the desired bond strength (for example, Liqui-Tape Silicone Adhesive, Waterproof by Walker Tape Co., West Jordan, UT). This adhesive can be applied under the liquid sealant or chemically mixed with the liquid sealant prior to its application, depending on its chemical make-up and final mixing properties. When applied under the sealant, the adhesive may need to become tacky (a.k.a., applied set time) prior to sealant overlay. A fast-setting, two-part sealant that is mixed prior to use may be useful in some circumstances, such as Skin Tite® silicone available from Smooth On, Easton, Pennsylvania, which is ACMI Certified Safe and may be used by itself or mixed with a thickener, such as Thi-vex® thickener, also available from Smooth On. A polymer sealant, or other material with the ability to bond into a continuous occlusive sheet, with adhesive-like properties due to high Van der Waals forces may be desirable, where no additional adhesive is needed.

Rubber polymers, such as latex, synthetic rubber, and hypoallergenic latex, are examples of polymers with desired properties for both the dressing-to-skin and tube-to-dressing interfaces. For example, Deviant Liquid Latex from Deviant, a subsidiary of Envision Design, San Jose, CA and Liquid Latex Fashions Body Paint from Liquid Latex Fashions, Warrington, PA were both demonstrated to seal the dressing at both dressing interfaces. The drying and curing time for the latex was significantly reduced by applying the liquid to the skin with an atomization process or with a saturated sponge technique, which are further disclosed in the sections below; by adding alcohol, which helps to absorb the water that evaporates from the latex; and/or by flowing a gas across the sealant for convection drying. For most applications, the curing/drying time was lowered to immediately (at most 1 minute) from the 5-10 minutes previously stated by Deviant at http://www.liquidlatex.net/.

Examples of suitable latex materials include Vytex Natural Rubber Latex (NRL), a brand of natural rubber latex produced and marketed by Vystar Corporation, Duluth, GA Vytex is manufactured by Revertex Malaysia and distributed by Centrotrade Minerals and Metals, Inc. Protein test results show that Vytex NRL typically has 90% fewer antigenic proteins than Hevea natural rubber latex. Therefore, Vytex causes less exposure and developed latex sensitivities. The Vytex has two products with different levels of ammonia; ammonia is a stabilizer and preservative, and both functionally are feasible for the NPWT liquid sealant and drape components, although alternative stabilizers to ammonia may irritate the skin less. Liquid latex for body painting typically contains ammonia, which is what has been applied to patients during field studies with no irritations. Vytex NRL, low ammonia compound, has provided functional, occlusive drape and sealant components on clean, unwounded skin in a lab setting.

Another suitable Hevea latex material is FSC Hevea produced and marketed by Yulex Corporation, Phoenix, AZ Yulex claims that it removes over 99.9% of the impurities, including proteins. Even more preferable than Hevea latex, Yulex Corporation, Phoenix, AZ also creates hypoallergenic latex from guayule (*Parthenium argentatum*). Yulex's guayule biorubber emulsions and solids have none of the sensitizing antigenic proteins found in traditional Hevea latex and is considered a safe alternative for people with Type I allergies. Yulex's biorubber emulsions are registered with the Personal Care Product Council and its INCI name is *Parthenium argentatum* Bark Extract. This is a presently preferred material for the NPWT dressing and sealant, in order to provide a non-allergenic material option. Yulex presently has ammonia and ammonia-free options. Yulex is also developing a Russian Dandelion-based emulsion that may also be preferable in the future, as a non-Hevea rubber option.

Synthetic materials such as nitrile rubber and neoprene are alternatives to natural rubber that do not have allergy-provoking proteins, but can also generally have poor elasticity with higher risk of break rates and viral penetration rates. Therefore, they are generally less ideal for many of the dressing applications according to the present invention, but may be suitable in some circumstances, particularly for the drape for which curing on the skin and drying time are not issues. Other multi-part materials, such as Room Temperature Vulcanizing silicones and certain polyurethanes which are two-part materials with base and curative components, may be acceptable in some applications.

Extremely low stiffness, which is achievable with many rubber-type materials, increases its bonding ability through Van der Waals forces alone. The high elasticity capable of being achieved using rubber polymers accommodates for the high levels of tensional strain reached at the skin surface during large deformation body movements. Additionally, the material properties of rubber polymers may also accommodate for the tendency to buckle when compressive strains are applied, depending on any initial interface crack sizes and adhesion strength. A desirable sealant accommodates for the large variability over time and surface area of the skin surface strains experienced during large deformation human motions; in the literature, the maximum large deformation strain is indicated to be approximately 0.45 in tension and 0.3 in compression. As rubber mechanical properties are sufficient to achieve structural integrity, the Van der Waals adhesive properties determine the applicable occlusive sealants, and depending on the polymer, an additional adhesive may be necessary.

The liquid sealant should have viscosity and curing properties, preferably including minimal shrinkage, that enable it to conform to all contact surfaces during the application and curing processes, such that no air leak channels at the interface are present after its application. At the dressing-to-skin interface, the sealant should conform to the folds and creases in the skin that are often bridged when applying a standard, planar wound dressing. These types of bridged cracks at all component interfaces are often a significant source of air leaks into the system without a liquid sealant. Once a crack exists, crack propagation occurs in tension and compression with reduced, applied strains, so air leak channels can form overtime with reduced strain magnitudes. Therefore, eliminating any initial cracks at all of the interfaces is desirable. At the dressing-to-skin interface, structures, such as hair, often create opportunities for crack propagation and air leaks into a wound dressing, and therefore, hair is often shaved before dressing applications. The need to shave the hair from an infectious standpoint is not desirable, as the shaving process creates trauma at the hair follicles and increases the risk of infection. With a liquid sealant, these structures can be completely enclosed in the air-tight sealant, and therefore, are not a source of crack propagation under the sealant and do not typically require removal prior to the sealant application, as cracks at the dressing edges are most critical to seal, in order to resist crack propagation due to tension. In some constructions, adhesive on the first surface of the drape is sufficiently thick and/or flowable to seal around hairs and skin crevices and to minimize crack propagation.

The sealant thickness, number of components, wound location, and sealant viscosity determines the optimal sealant application method(s). The liquid sealant may have a very high to low viscosity, as long as it can completely wet the contact surfaces. If mechanically applied (e.g., brush "painting" application, roller application, sponge painting/dabbing application, squeegee or other squeeze-type application, application by-hand (i.e., finger) with or without a non-stick cover, etc.), a viscosity that avoids run-off due to gravity is preferable in order for the sealant to be ergonomically applicable to any wound location. This leads to higher viscosities and is limited at the low viscosity range. The applicable viscosity is dependent on application thickness, as thicker applications are more prone to run-off due to shear stress.

Brush painting is not the preferred application method; when brushing the sealant, it is difficult to achieve a constant thickness. If the thickness varies significantly over its surface area, the mechanical properties and debonding energy will also vary significantly, which may cause occlusive dressing failure. Brushing also has other drawbacks, as it is easy to trap air bubbles in the sealant, which are a source of cracks for crack propagation. Also, it is difficult to produce and maintain a very thin coat, which significantly increases the necessary Van der Waals bonding strength; it increases the stiffness of the final dressing and decreases its ability to conform to large tissue strains. In addition, higher application thickness is prone to run-off, creating a lower viscosity limit of applicable sealants for any wound location.

An alternative to brush painting is sponge painting/dabbing. It was determined that this is a preferable method when using a saturation sponge technique. The applicator is a sponge embodiment, preferably soft, additive free, high density, fine-pore, hydrophilic foam. Different materials can be used for manufacture of the foam, including: polyurethane, polyester, latex, styrene-butadiene rubber (SBR); latex-free is preferred. For a low viscosity sealant, the uncompressed pore sizes are preferably at least 15-90 pores per inch (ppi) with smaller pores being the majority, and more preferably all pores are at least 90 ppi. Preferably the foam density is above 50 kg/m$^3$ and more preferably above 80 kg/m$^3$. The sponge is preferably of a substantially open cell structure in order to absorb fluid and is used wet. To prep the sponge, it is allowed to absorb a liquid. In the preferred embodiment, that liquid has a low enough viscosity to saturate the sponge (e.g., water or saline), and the sponge is completely saturated. This can be done during its packaging, by having the sponge impregnated with the fluid before packaging or packaged in a container with enough volume of fluid for the proper absorption. In this case, the package must be tight enough (i.e., minimal evaporation rate) to continuously hold enough fluid until use; preferably, it is air-tight in order to prolong shelf life and to deter potential contamination of the sponge. A prefilled sponge and/or packaging will eliminate the requirement to have a separate container of fluid (and potentially a tray for assistance in absorption) in the kit for saturation purposes, or for the caregiver to independently provide enough fluid (e.g., saline) and potentially a tray for assistance in absorption for this purpose. In order to promote saturation, the sponge may be squeezed and released in the fluid. In prefilled packaging, this may be done prior to opening the package for the sponge. In packaging that does not contain fluid, the fluid can be infused directly into the sponge, the sponge packaging can be filled with fluid for absorption once opened, or the sponge can be inserted directly into the container or running stream (i.e., faucet) of fluid, in order to eliminate any need for a separate tray.

Before using the sponge, any excess saturation fluid should be squeezed out. For use, the sponge is preferably damp and not saturated. This is to prevent unwanted dripping of the saturation fluid and the mixing of the excess fluid with the sealant, which may change its properties. In some embodiments, the saturation fluid may enhance the properties of the sealant or be necessary for drying or curing, in which case excess fluid may be desirable and should not be removed. The fluid inside the sponge prevents sealant absorption into the sponge, and therefore, the sealant remains on the surface of the sponge, and it is easily transferred to the dressing and skin. In the preferred embodiment, this saturation and dampening process causes the sponge to expand in volume, when compared to the dry sponge volume.

Filling the sponge with fluid has many benefits, including: it allows more sealant to transfer onto the skin-dressing edge; it discourages the drying and/or curing of the sealant on the sponge applicator, which assists in transfer of sealant to the skin-dressing edge for prolonged application periods; less sealant is used in the application process; a smooth, thin, more even coat can be made by application methods such as painting or dabbing, since the sponge can be pressed onto the skin-dressing with a smooth transfer; the applicator does not stick to the curing and/or drying, applied sealant; and the applicator does not stick to any adhesive surfaces of the dressing. With these functional characteristics, the applicator can use multiple application methods, including dabbing/spackling, which creates and airbrushed-like finish and painting, during which the sponge can be used to smooth a thin layer of sealant over the application surface.

Based on the flexibility of the manufacturing process, the sponge can be made in many different shapes and sizes. In the preferred embodiment, the sponge is rounded on any edges that cross the seal path during use, in order to prevent sharp edges of the applicator from applying thicker edge lines of sealant along the seal path (similar to the edge lines formed when painting with a paint brush). The rounded edges are used along the interface to be sealed (i.e., seal path), such that a smooth sealant surface is formed. In the preferred method for applying the wound dressing, the sponge is first used in a "bouncing" and "twisting" motion called "stippling" and "twisting" in make-up application. This fills in any contours, while applying a thin layer that minimizes the risk of run-off. Then, in the preferred method, the sponge is used to create a smooth finish by lightly painting it along the application line of sealant (i.e., seal path); in a number of preferred embodiments, this makes removal of the sealant easier, as smoothing the sealant creates one continuous, solid layer. The applied layers of sealant can be made very thin, minimizing the risk of run-off.

Currently, similar sponges are used for make-up application. It is considered an alternative to air-brushing. The application finish depends on the pour size of the sponge and its stiffness. However, in make-up application, the surface is not smoothed out. A popular sponge in make-up application is the Beautyblender, which is an elliptical shape, similar to a three-dimensional teardrop, with no sharp edges and multiple contours to match different surfaces of the skin. In the wound dressing application, the elliptical shape would be ideal, such that no thick edges of sealant are applied. However, in order to keep manufacturing costs down, a teardrop shape stamp of a planar sponge is preferred (i.e., a two-dimensional teardrop). This embodiment has no sharp edges that cross the seal path, as long as the teardrop is kept perpendicular to the seal path during use. A handle, similar to a paint brush handle, may be added to the applicator sponge to improve its ergonomics, such as done for make-up sponge applicators. The preferred embodiment is hand-held without a handle, as it is meant to be a disposable component, and therefore, minimizing costs is preferable. In addition, in our user testing, a handle did not improve the application time or end results.

Additives such as curing agents, accelerators, convection drying agents, and adhesives may be applied via separate application methods, if they are not mixed with the sealant prior to application. Their application method may be via brush painting, roller, sponge painting/dabbing, squeegee or other squeeze-type, by-hand (i.e., finger) with or without a non-stick cover, spraying, etc. The application of these additive components and the sealant may occur in a multi-step process. They may be stored and applied from separate containers with the same or different application methods in series or in parallel. However, they may also be applied in parallel or series from the same containing body. One example is a parallel spraying process, for which three ports exist: the sealant port, the shearing fluid port, and an accelerator port; these three components can combine during the atomization process in the spray nozzle where the three ports may interact. Another example is a spray apparatus that allows the amount of sealant (and potential accelerator) to be controlled, such that it may be shut-off; the shearing gas then becomes a convective drying gas. Yet another example is a squeeze apparatus that separately contains the sealant and additional components and that mixes the desired amounts of sealant and components in an outlet port upon their exit; this technique is similar to a 3M Epoxy Mixing Nozzle by 3M, St. Paul, MN The resulting mixture can be applied directly to the dressing with the squeeze applicator or can be partnered with another method, such as the saturation sponge application method, where the mixture is first transferred directly to the sponge; transferred to the sponge, using a separate dipping container; or applied directly to the dressing and further manipulated with the sponge for the finishing operation.

Various polymers with rubber-like properties were determined to have the desired sealant properties. The thickness of a desired seal embodiment can be built-up in a successive layered, lamination process. A material that has a strong affinity for itself with either strong Van der Waals forces or chemical bonds that form between its layers, such that the final material behaves as a continuous one-layer sealant is desirable. The desired thickness is the minimal thickness needed for strength and to achieve the desired occlusive properties, which is material dependent. This thickness is often thinner than the thickness that can be reliably and uniformly achieved through most application processes; however, the spraying and saturation sponge application methods have shown repeatable, desirable results. Through lab testing, it has been shown that the atomization process provides a method to achieve the thinnest functional sealant thickness.

Occlusive dressings are beneficial beyond NPWT and in combination with advanced NPWT features. Some proven benefits of occlusive properties are highlighted here. The occlusive characteristic may enhance the penetration and absorption of topically applied medications, such as ointments, powders and creams, which can be beneficial in combination with standard wound dressings and with therapies, such as NPWT. The V.A.C. Instill Therapy Unit (KCI) was meant to combine instillation therapy with NPWT. Instillation, as defined by the V.A.C. Instill documentation, includes both: 1) the introduction and removal of topical solutions in liquid form and 2) the ability to flush out and clean a wound through a rigorous irrigation technique. The main caregiver complaint about this and other instillation-purposed dressings is that they often leak liquid during the instillation process, especially during a rigorous irrigation procedure, which further induces air leaks during continued therapy. The occlusive seal and dressings disclosed in this disclosure would solve any leak issues that arise. Often the irrigation process introduces leaks by propagating cracks in the dressing; by eliminating these cracks, the sealant and dressing techniques in this disclosure significantly reduce the potential for leaks and leak formation during instillation. The port(s) needed for instillation fluid insertion and removal can be directly connected to the disclosed occlusive dressing embodiments with the same tube-to-dressing connection methods in this disclosure.

Although the presently disclosed occlusive dressings were developed with NPWT system in mind, they can be used for any application for which an occlusive (a.k.a., air tight and water tight), air tight, or water tight seal to the skin is desirable. Therefore, they are applicable in multiple fields beyond NPWT, and more generally in the field of skin sealants and their methods. Truly occlusive dressings create a control volume over the area of tissue that they are applied, which is a desirable feature for multiple applications, many which are disclosed in this application document.

The occlusive dressings discussed in this disclosure are the first skin dressings to provide a control volume, as no other dressing to-date is proven to be (reliably) truly occlusive. This would benefit the enhancement of advanced healing therapies that are sensitive to any variation in the environment, such as stem cell based therapies, for which complete control of the environment is necessary to achieve deterministic results. If a specific air leak is desirable, its rate can be precisely controlled into the control volume through precision valves. These valves can be connected to the disclosed occlusive dressing embodiments with the same tube-to-dressing connection methods in this disclosure. Currently, there is no accurate predetermination for the air leak rate into any wound dressing, especially since most dressing air leaks have variability over time and with body movement. Furthermore, truly occlusive dressings may be used in in vivo acute toxicity tests of dermal irritation and sensitization. The test animal is shaved and the test material is applied to the skin and wrapped in an occlusive material. The skin is then exposed after 23 hours and an assessment for redness and edema is made; this assessment is repeated 48 hours later.

FIG. 1 is a schematic expanded perspective view of a dressing assembly 20 including a drape 22, a novel flange 26, a flange-to-tube connector 401, and a tube 24 with first and second protective liners 28 and 30 prior to application of a liquid sealant according to the present invention. Drape 22 and second liner 30 define holes 32 and 34, respectively, through which flange 26 is insertable. It was proven through multiple experiments that an occlusive seal is possible by attaching the flange 26 to the drape 22, using only the pre-applied drape adhesive. This seal is functional for the therapy period in the presence of wound fluid. However, adhesive selection in this case is very critical, and an additional adhesive and/or sealant is often desirable, if only for redundancy.

Figure 2:
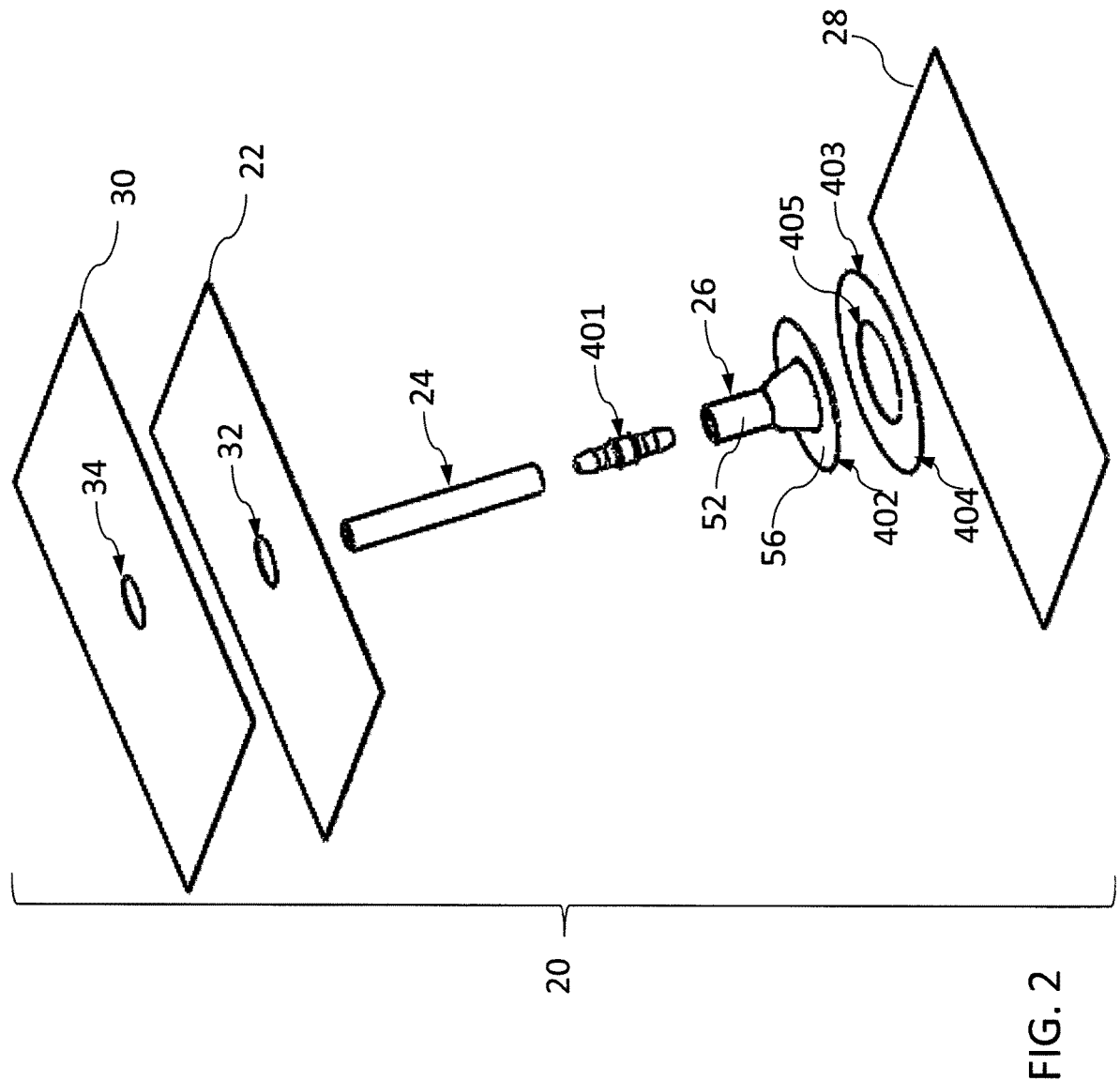
FIG. 2 shows the kit components of FIG. 1 with an adhesive patch component according to the present invention positioned beneath the flange, prior to application of a liquid sealant according to the present invention.

In many applications, it is ideal for the flange foot 56 to have adhesive on its first surface 402 of FIG. 2; for example, in the case that it overlaps the periwound skin, which is prone to happen when small wounds or surgical incisions are treated. In the preferred embodiment, adhesive is applied to the entire surface 402 that may contact the periwound skin. An adhesive can be applied to this surface 402 during manufacture or during application; in addition or alternatively, adhesive can be applied to the surfaces that the flange must adhere to during application. In many preferred embodiments, this is a skin contact adhesive. It can be applied in the form of a liquid adhesive, or in the preferred embodiment shown in FIG. 2, this adhesive may also be applied with an adhesive patch 403 component. This patch component 403 can be in the form of a single layer of adhesive or a multi-layer laminated and/or coated embodiment. The adhesive patch 403 adheres to the flange surface 402, preferably with an adhesive applied during manufacture of the patch, and has the desired contact adhesive (for example skin contact adhesive) on the opposite side 404. In one preferred embodiment, the outer radius of the adhesive patch 403 is larger than the outer radius of the flange foot 56. In this case, the adhesive patch also adheres to the drape 22 during assembly. This helps to create a reliable air-tight seal at the flange-to-dressing interface (i.e., part of the tube-to-dressing interface) and increases the resistance to pull-out forces of the flange through hole 32.

In one preferred embodiment, the patch 403 has a high enough cohesive strength, such that it does not fail during wear; there may be a large differential in the modulus of the materials that the patch is attached to at the flange edge (i.e., between the flange 26 and drape 22), which may increase the potential for failure. If the patch 403 extends onto the drape 22, it is preferred to have the same or lower modulus than the drape 22 and to have a thin profile, in order to minimize the change in debonding energy, bending stiffness and the thickness differential between the drape and the drape and patch laminate. In the preferred embodiment, the edge of the patch is thin enough or tapered, in order to adhere in a continuous manner to the periwound skin at the patch 403 contact edge with the drape 22.

In one preferred embodiment, the diameter of the hole 405 in the adhesive patch 403 is larger than the smallest diameter of the flange foot 56; therefore, the adhesive patch is adhered completely to the flange with no overlap at the inner diameter. In the preferred embodiment, the adhesive patch is applied to be occlusive during manufacture, although user application methods are also possible.

FIGS. 3A and 3B illustrate the novel symmetrical flange 26 and tube connector 401 of FIGS. 1 and 2 being connected to form a symmetrical connector assembly 406, FIGS. 4A and 4B. FIG. 3B is a cross-sectional view of a symmetric plane of FIG. 3A. In the preferred embodiment, no additional adhesive or sealant is used at this interface, although in some embodiments, additional adhesive or sealant may be applied to bond the components together. When connecting the tube connector 401 to the novel symmetrical flange 26, one or both of the components may first be wetted, such as with alcohol, in order to assist with the connection and reduce the friction between the components. As shown in FIGS. 3A and 4A, the barb can be attached during an additional assembly step. However, many other connector embodiments and methods can be used, depending on materials and design. Attachment methods for these connectors to the flange and tubing include over molding, ultrasonic welding, solvent bonding, infrared welding, and adhesive bonding. One potential adhesive is a silicone adhesive, such as Liqui-Tape adhesive from Walker Tape Company as mentioned above. A compression fit of the tube to the flange is also possible for an air-tight attachment. In some constructions, flange 26 is manufactured directly onto tube 24, via a dipping, molding or spraying process. A liquid sealant can be applied to the junction of tube 24 and flange sleeve region 52 and/or to the junction of tube 24 and connector 401 and/or to the junction of tube connector 401 and flange sleeve region 52, in order to further occlude possible fluid escape at that junction.

Figure 5:
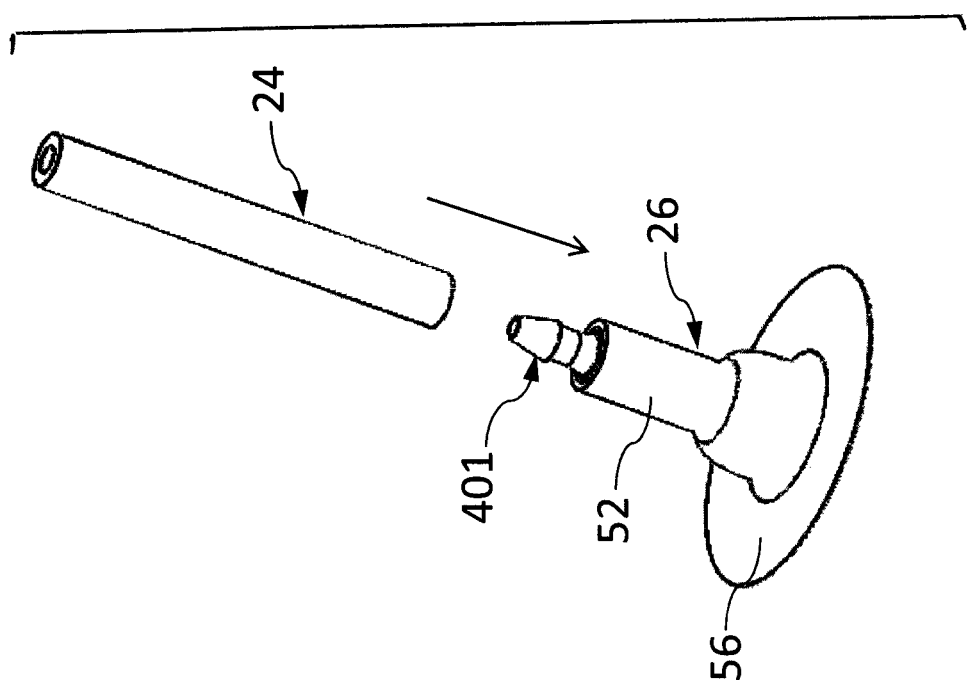
Figure 7A:
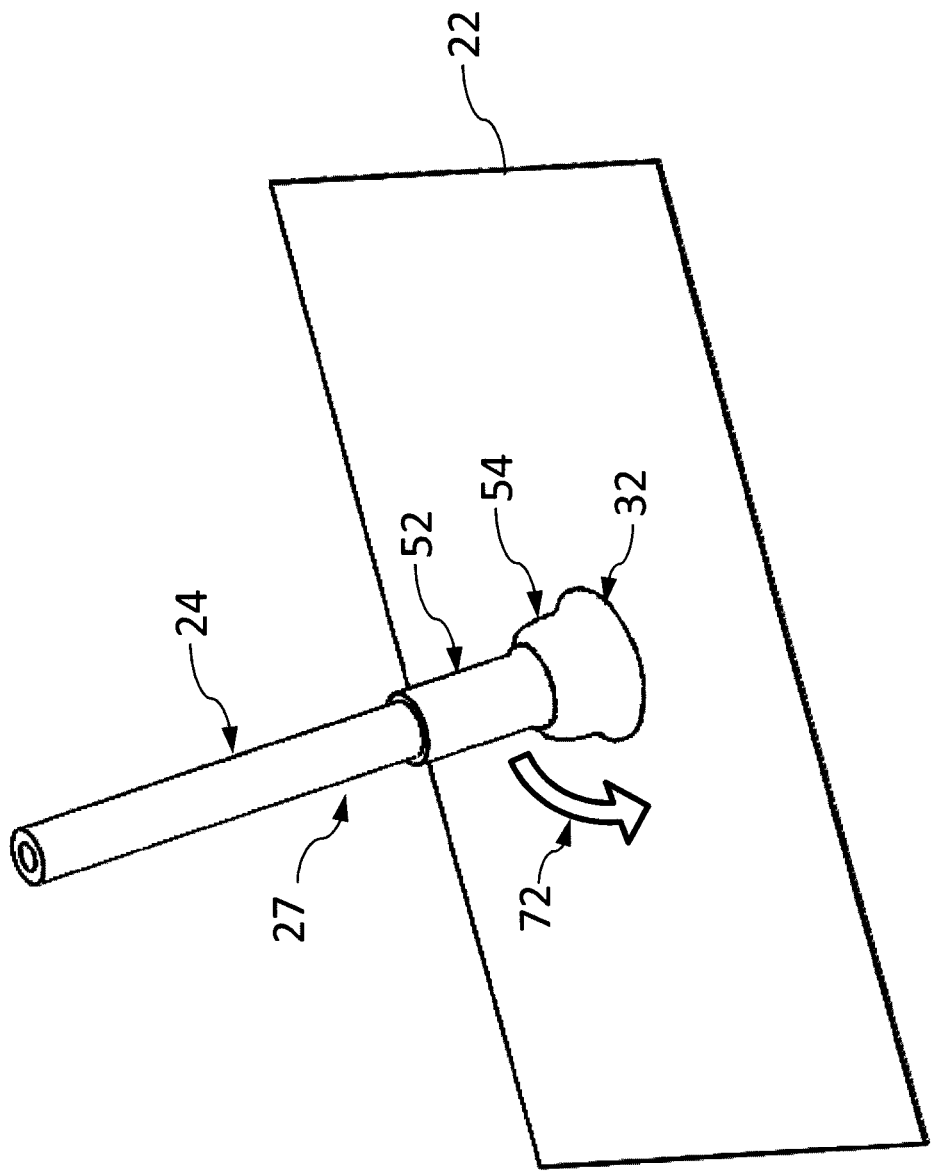
FIGS. 7A and 7B illustrate repositioning of the upright tube of FIG. 6 into a desired side orientation.
Figure 7B:
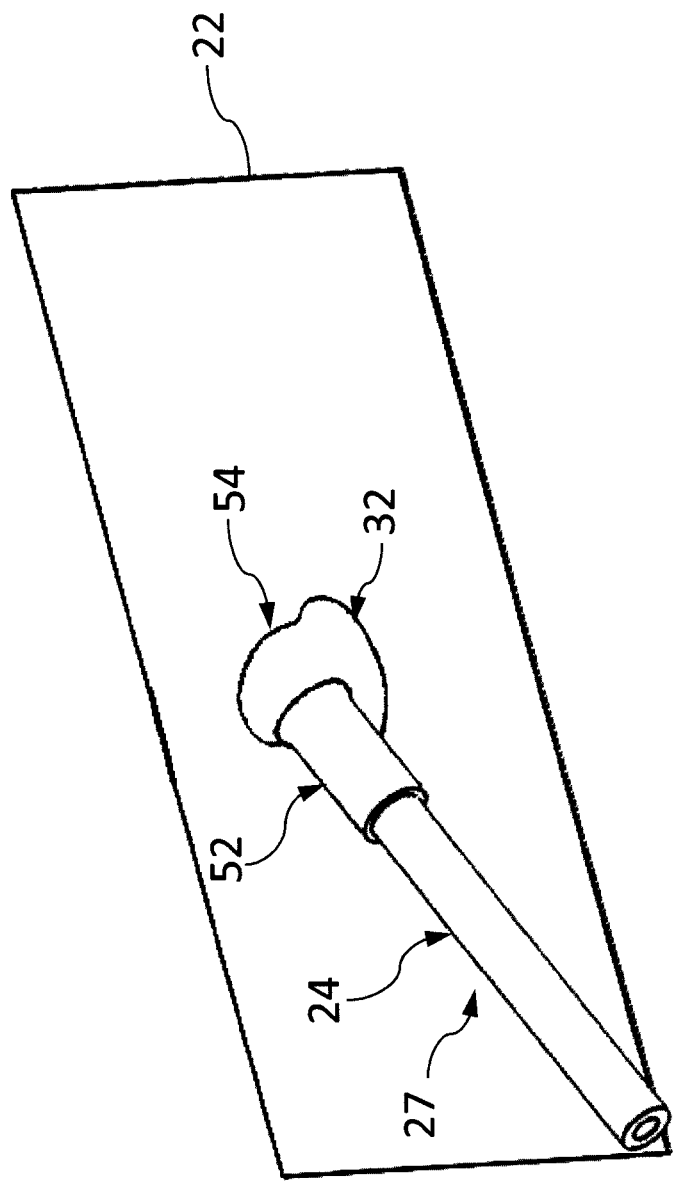
Figure 8:
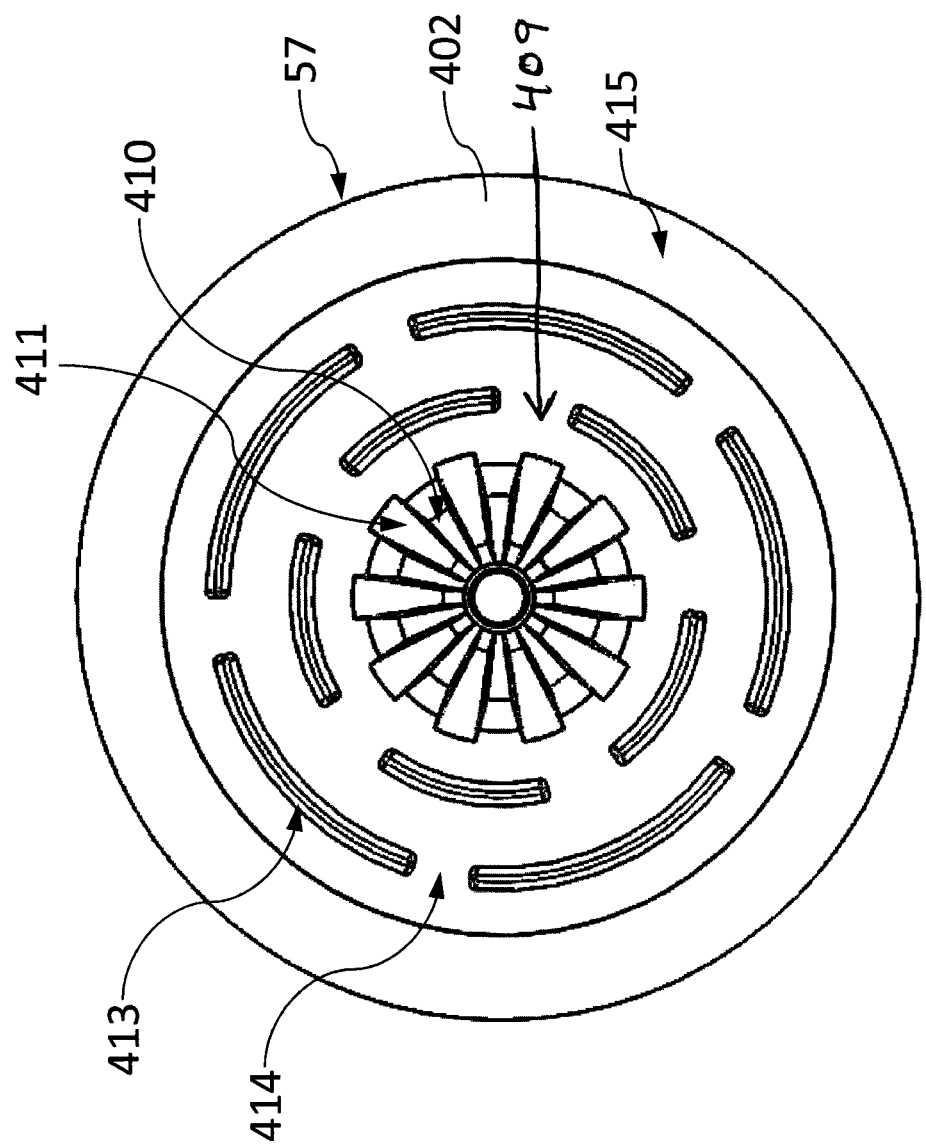
FIG. 8 is a bottom view of the novel flange of FIG. 3A-4B.

Rotation region 54 serves as a flexible ball joint in this construction. Once the tube 24 is attached to the barb 401 through a standard barb-to-tube connection (FIG. 5 and FIG. 6), tube 24 can be manipulated in the direction of arrow 72, FIG. 7A, to a desired side orientation as shown in FIG. 7B. In the preferred embodiment, the flange 26 includes an "anti-occluding feature" in the design of the flange 26. The flange design has the anti-occluding feature built into it, in order to resist blockage of the flange/tube. In one preferred embodiment, the anti-occluding feature is a ribbed pattern 409, shown in FIGS. 3B and 8. During manipulation, the ribs 409, prevent the fluid path from occluding. In one preferred embodiment, the "hills" 410, FIG. 8, are smaller in width than the "valleys" 411, FIG. 8, and therefore, if the ribs interlock, total occlusion is not physically possible; any taper in the ribs must be accounted for to assure geometrical mismatch. With this flexible orientation, the opening at the top of the anti-occluding feature in the flange (e.g., the ribs 409) must either: not have a continuous edge in a plane that can occlude against a surface; and/or must have a larger diameter than the width of any feature that it is able to occlude against. As shown in FIG. 4B, the width of the peak of the hills is smaller than the diameter of the fluid path at the distal end of the barb 412, further prohibiting any potential occlusion. In the preferred embodiment, the anti-occluding feature is a ribbed pattern 409; however, a spiral tube end, as shown in FIGS. 2 and 3 of U.S. Pat. No. 9,173,777, can be injection molded as a projection on the underside of the flange component (separate from the tube itself), and other anti-occluding features can be realized, such as in FIG. 4 of U.S. Pat. No. 9,173,777, injection molded, adhered, or connected by another method as a projection on the underside of the flange component (separate from the tube itself). These features can be used individually or in combination.

During patient wear, it is preferred that the flange foot 56 remain parallel to the skin surface. This assures that the flange foot surface 402 will not fold onto itself, causing the fluid path to be obstructed and potentially occluded. Concentric ribs 413, FIG. 8, can increase the stiffness in the plane of the flange foot 56, preventing the flange foot 56 from folding onto itself. Breaks in the ribs 414, FIG. 8, allow the flange foot 56 to remain flexible for patient comfort; however, the ribs are staggered in such a way that a rib exists on any potential fold line of the flange that may cause occlusion if the flange foot surface 402 folded onto itself.

The flange is tapered on surface 402, such that the thickness of its outer edge 57 is minimized. This is taper 415 is to minimize the step at the edge 57 that the adhesive patch 403 has to seal over. In the preferred embodiment, the adhesive patch 403 is adhered to the flange and drape in a continuous manner, without any breaks. Complete wetting during the assembly process is easier to achieve with the gradual taper 415.

In constructions where flange 26 is constructed entirely from, or coated with, a material that has an affinity for itself, sleeve region 52 may self-adhere to rotation region 54 and adhesion region 56, to the extent that region 56 is exposed, when folded against itself as shown in FIG. 7B. Where the material forming the exterior of flange 26 has an affinity for the material of drape 22, especially for materials containing latex compounds or other tacky compound, the exterior of sleeve region 52 will also adhere to drape 22 at least to some extent; latex-type material applied to the surface of tube 24 will further enhance this adhesion. Fixing the tube 24 into a fixed orientation such as shown in FIG. 7B may be especially beneficial for bed-ridden or less mobile patients so that the tube can be positioned to avoid the patient lying on the tubing for long periods of time or to avoid compromised areas around the wound. In other circumstances where the tube remains movable, it can be easily repositioned because rotation region 54 remains flexible and the tube can be monitored and moved frequently to assure that tissue is not degraded from lying on the tube in one position for an extended period. Especially for active patients, the tube 24 can be periodically re-positioned by the patient or by a healthcare professional.

Figure 9:
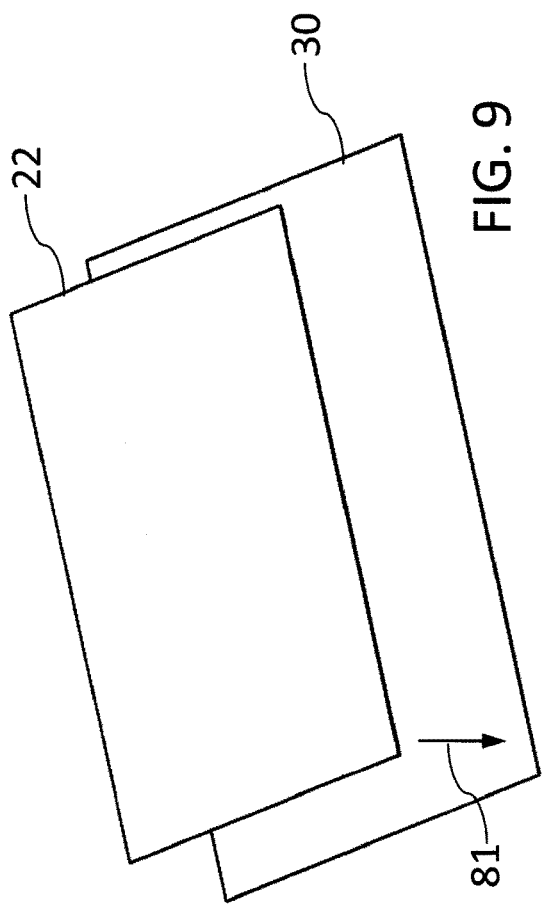
FIGS. 9 and 10 show a drape being connected to an upper liner to manufacture a dressing according to the present invention.
Figure 10:
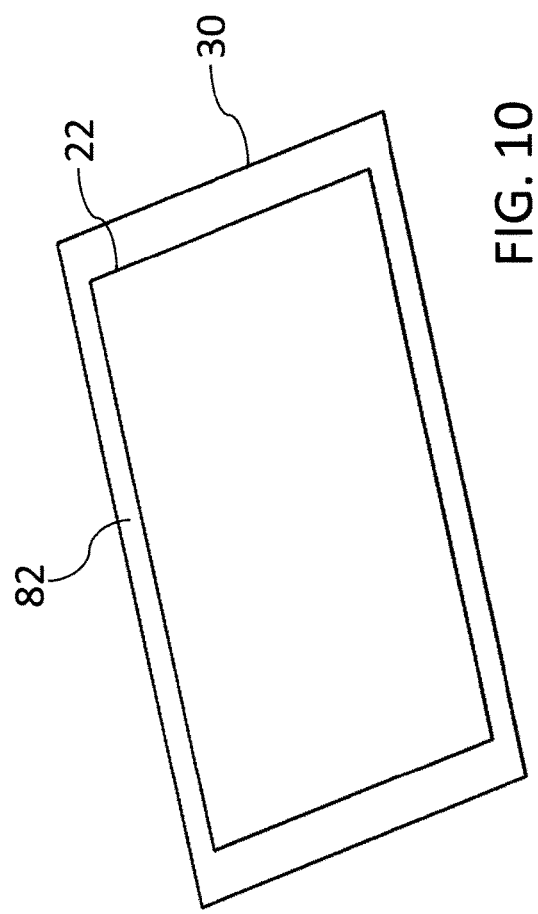

FIGS. 9 and 10 show a drape 22 being covered by an upper liner 30 to manufacture a dressing according to the present invention. Preferably, drape 22 has a thickness ranging from 2 microns to 0.4 mm, especially in portions which will be applied to skin; a greater thickness in the center portion to be located over a wound is less critical for occlusivity. In some constructions, skin contact adhesive is pre-applied on the upward-facing surface shown in FIGS. 9 and 10, which will be placed in contact with skin during use; in other constructions, adhesive is also placed on the opposite side of drape 22, to be covered by liner 30, as indicated by arrow 81 in FIG. 9, for storage and handling. The adhesive is applied as a uniform coating in some constructions and, in other constructions, as concentric circles or other non-uniform pattern. Preferably, liner 30 has extension 82 around the perimeter which extends beyond the drape 22 to facilitate handling of the dressing without touching any adhesive, and to enable easy removal of the liner 30 from the drape 22 after placement on a patient. In some embodiments, the extension 82 extends on less than all sides of drape 22; in this case, the preferred embodiment is extensions on at least two opposite sides of drape 22.

FIG. 11 shows a hole 32 punched in both layers of the dressing of FIG. 10.

Figure 6:
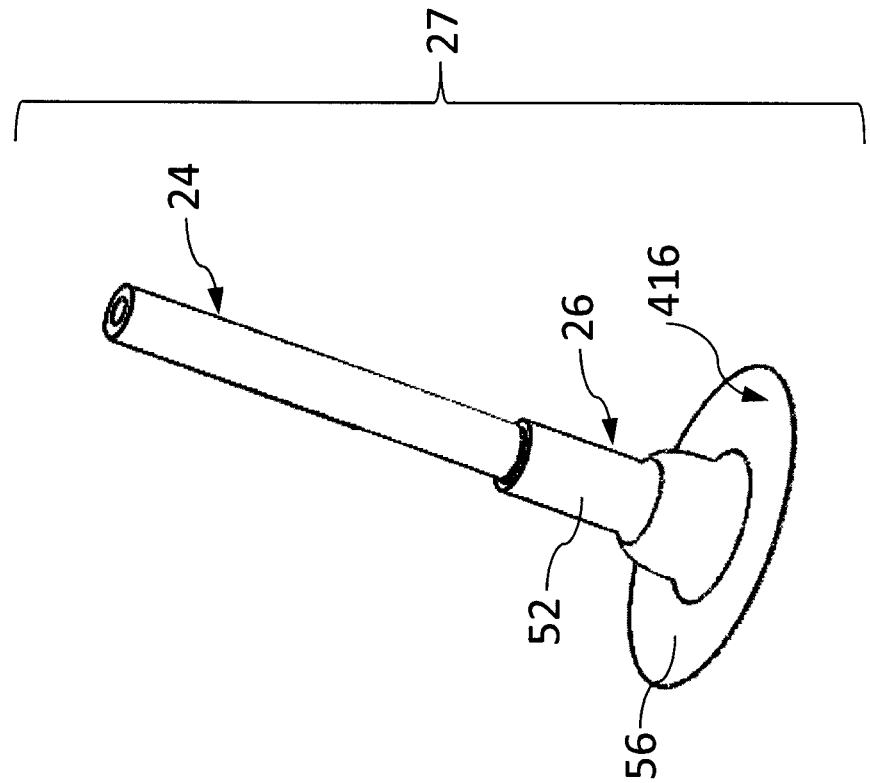
FIGS. 5 and 6 are a schematic perspective views of the tube of FIGS. 1 and 2 being connected to the novel, preferably symmetrical connector assembly of FIGS. 4A and 4B.

FIGS. 12 and 13 show a tube assembly 27 being inserted, arrow 90, onto the dressing of FIG. 11 with the adhesive region 416, FIGS. 6 and 12, on the second side of flange foot 56 to edge 57 of the flange 26 being sealed to the drape 22 utilizing the pre-applied adhesive. Additional adhesive or sealant can be added around edge 57 or pre-applied to region 416 or drape 22, as desired.

FIGS. 14A and 14B show adhesive patch 403 applied to the first surface of the flange 402, FIG. 8, flange edge 57, and the overhang region 417 on the drape 22. This further secures the flange 26 to drape 22 in an occlusive manner, and it further prevents the flange 26 from pulling out of hole 32, FIG. 11, if a large pull force is applied to tube 24 during wear. As shown in FIG. 14A, in one embodiment, the adhesive patch 403 does not cover the concentric ribs 413. This may be done in the case that the ribs 413 are difficult to seal over during application of the adhesive patch 403 or in the case that there is an advantage to not sealing over the ribs 413, such as additional shear resistance over the wound packing material. In the preferred embodiment, the inner diameter 405 of the adhesive patch is as close to the inner diameter of flange foot region 56 as possible without overlap. This allows smaller wounds to be treated with the desirable characteristic that the entire wound edge is sealed to the dressing with skin contact adhesive, in order to prevent maceration. If the entire wound edge cannot be sealed, it is desirable to protect that area with an additional skin protectant, such as a piece of film adhesive dressing, or by applying an additional skin contact adhesive. FIG. 14B shows the dressing assembly, where the flange does not have concentric ribs 413 and the inner diameter 405 is at the inner diameter of flange foot region 56, without overlapping the ribs 409. This is the preferred embodiment when a flange material or design is used, such that the ribs or other features on surface 402 are not necessary to reduce potential occlusive folding during wear. In the case that features on surface 402 exist, the adhesive patch 403 may not be desirable to cover these features.

FIG. 15 shows a protective liner 28 being added to the dressing 20 of FIG. 14B. Protective liner 28 protects the skin contact adhesive, when pre-applied, until liner 28 is removed as illustrated in FIGS. 16 and 17. FIG. 16 is a perspective view of the underside of the dressing 20 of FIG. 14B with the liner 28 being removed as indicated by arrow 106, such as by pulling on corner 108, to expose drape 22 with pre-applied adhesive. The protective liner 28 should be easily removable from the skin contact adhesive by the user. In one construction, shown in FIG. 16, liner 28 extends beyond drape 22 over extension region 82 of liner 30.

In one embodiment, shown in FIG. 17, liner 28 is even with the outside edges of drape 22 without any overlap. In the preferred embodiment, shown in FIG. 17, liner 28 has a split bottom liner, such as the plough fold 418 design, in order for the user to easily remove the liner 28 from the skin contact adhesive. The plough fold 418 allows the liner 28 to be removed preferably from above the center of an outside edge of drape 22, as shown in FIGS. 18A and 18B, or from above the adhesive area of drape 22 without an edge of drape 22 or of adhesive patch 403. Removing the liner 28 in this fashion, FIGS. 18A and 18B, is preferred, as: (1) the drape may have a tendency to lift from the upper protective liner 30 when the lower protective liner 28 is removed by peeling it perpendicular to the edge of drape 22 and/or from the corner as shown in FIG. 16, (2) the drape may have a tendency to lift from the flange 26 when the lower protective liner 28 is removed by peeling it perpendicular to an inside or outside edge adhesive patch 403, and (3) when the liner 28 is split, the user can apply a downward force on the stationary part of the liner as an adjacent part of the liner 28 is peeled off of the drape 22; this downward force can help the drape to stay adhered to the top liner 30.

Figure 19:
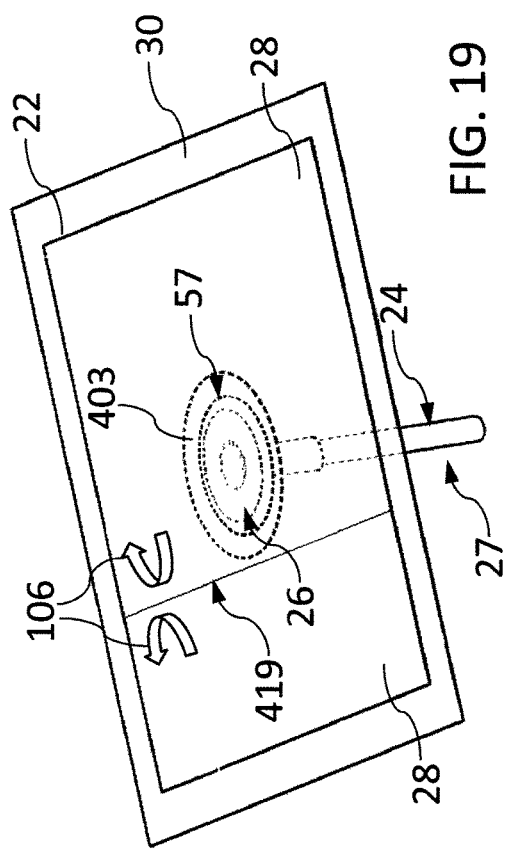
FIG. 19 shows an alternative protective liner adhered to the dressing of FIG. 14B.

Another embodiment of a split liner is shown in FIG. 19. This can make the manufacturing process easier with a kiss-cut during a die cutting process with either perforations or an incision 419, FIG. 19. With this embodiment, the liner 28 can extend beyond the drape 22 on at minimum one side of the perforation or incision, in order to provide an extension area 82, FIG. 16, to grasp the liner for removal, or, as shown in FIG. 19, the liner can be the same size of the drape and align with the drape; in this embodiment, it can be stamped with the drape in the manufacturing process. If there is no liner overhang or extension 82 to grasp, the liner can be lifted by bending the dressing assembly along the perforation or incision 419 to cause it to lift off of the drape 22 at the perforation or incision 419, in order to create an area to grasp, or by using separate handling tabs that can be adhered to the liner 28 for removal. The split liner serves two purposes: (1) it can be partially peeled back in order to at least one of insert the flange 26 into the center hole 32 in the drape 22 and apply the adhesive patch 403 without completely removing the liner 28 from the drape 22; the liner 28 can then be returned to its original position after the insertion of the flange 26 and/or application of the patch 403, and (2) it provides a method to peel the bottom liner off of the drape that minimizes the potential for the drape to peel from the top liner as the bottom liner is removed.

Figure 20:
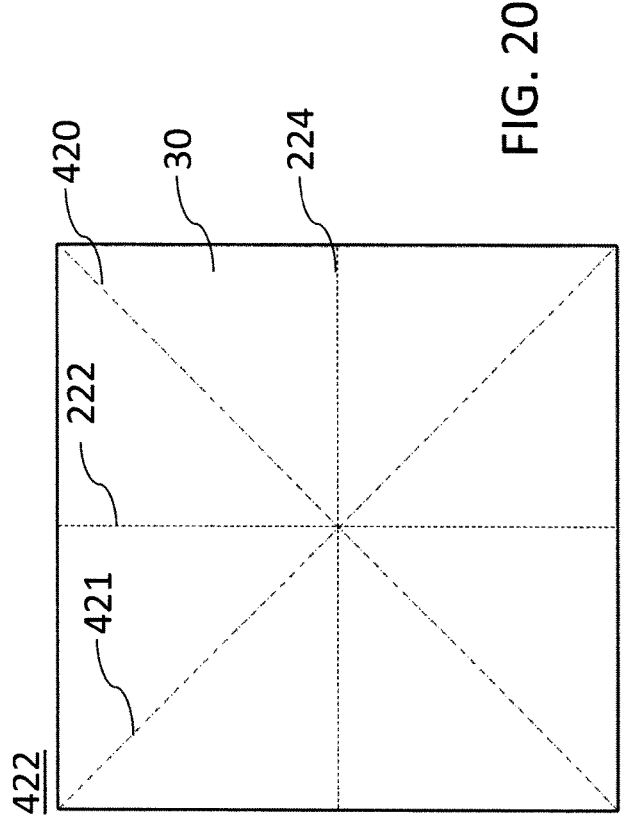
FIG. 20 is a schematic top plan view of a liner having perforations.

Features in the top liner 30 may also assist the user in the dressing application. When applying the dressing to a contoured surface, folds in the drape may be necessary to accommodate the contours and fully adhere the drape onto the periwound skin. These folds typically travel from the outer edge of the drape towards the tube 24 and are preferably made prior to the removal of the top liner 30. In this situation, the preferred application method is to minimize the number of folds by creating a few large folds. Preferably, there are no more than four folds, divided substantially equally around the periphery of tube 24. These folds are created when adhering the drape to the surface of the skin, forming a "T". To help in creating these folds, the top protective liner 30 may have specific features, 222, 224, 420, and 421, FIG. 20 (e.g., penetrating perforations, non-penetrating perforations and indentations) that weaken the bending stiffness of the liner 30 along the preferred fold lines (i.e., bottom of the letter "T"), in order to assist in creating folds. The folding process and folding locations will be guided by these new top liner features. Ideally, these features function the same as the fold line indentations used to help fold a cardboard box. This corresponds with the folding technique discussed in U.S. application Ser. No. 13/745,690 by the present inventor, now U.S. Pat. No. 9,173,777 and, as such, these features preferably exist along the indicator lines 222 and 224 in the top liner 30. During the dressing application, if any overhang of the folds beyond the edge of the dressing will stick to the skin or can be cut-off, then these folding features may also be preferable in locations other than the indicator lines 222 and 224, for example 420 and 421. Note that for manufacturing purposes these features do not need to extend all of the way across the liner to the edge of the drape; for example, a narrow border around the edge of the liner may exist that does not have any features.

Figure 21B:
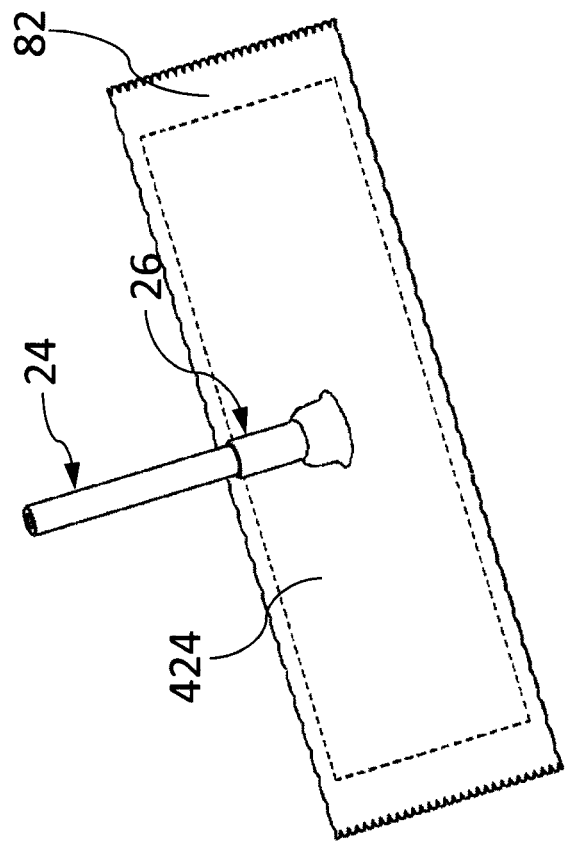
FIG. 21B is a perspective view of the liner of FIG. 21A, after a hole is punched, adhered to the top of a dressing.
Figure 21A:
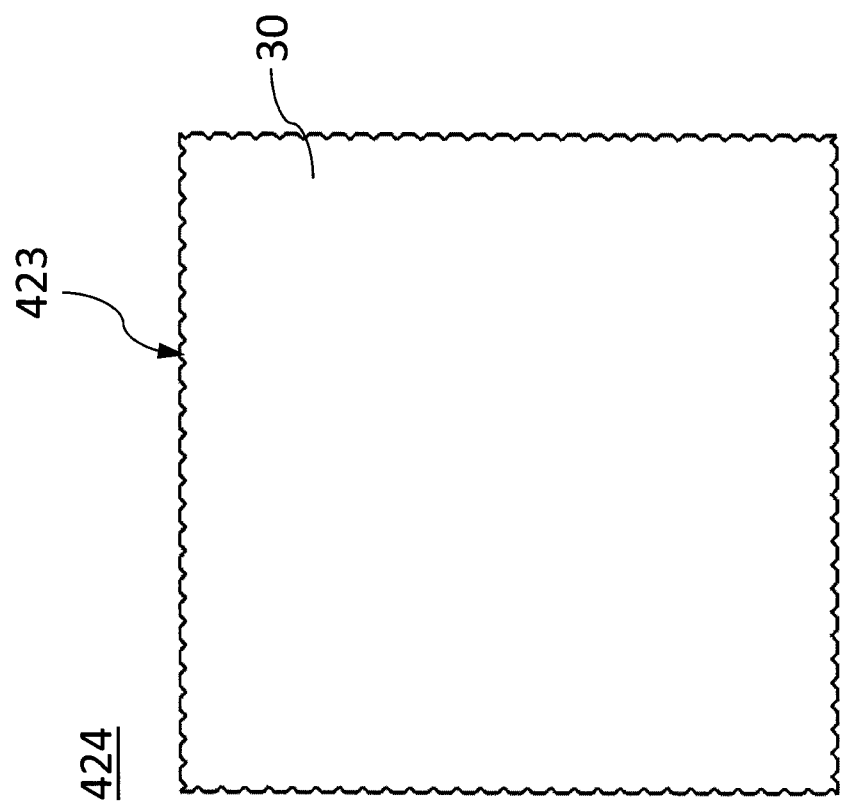
FIG. 21A is a schematic top plan view of a liner having serrated edges.
Figure 22:
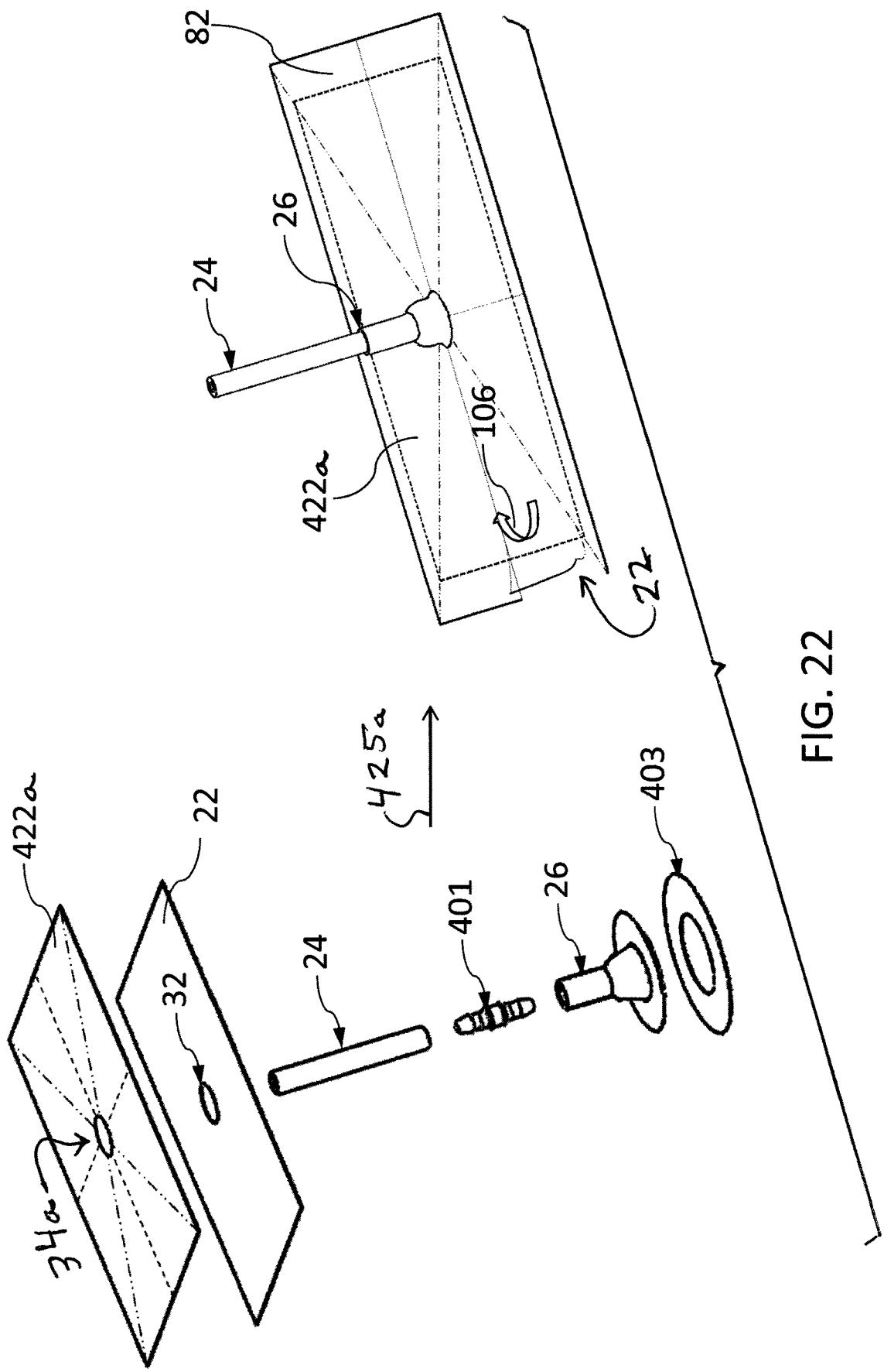
FIG. 22 shows an exploded view on the left and, on the right, a perspective view after assembly of the liner of FIG. 20, after a hole is punched, adhered to the top of a dressing and as the liner is being removed.

After application of the drape 22 over the wound, the top liner 30 should be removed. In order to protect the edges of the drape, the liner is preferably peeled from the center of an outside edge of the drape 22, similar to the bottom liner 28 being peeled off of the drape, where the liner adjacent to the part of the liner being removed can be held down in order to support the edge of the drape 22 on the skin. A variety of effective features can assist the user in dividing the liner 30 over the edge of the drape 22. If the liner 30 material is easily torn, such as paper, it can be manually divided by the user in any location. In the preferred embodiment, shown in FIGS. 21A and 21B, the edge of the liner 30 is serrated 424 in order to make the liner easy to tear by-hand. In another embodiment, the features used to assist in the top folds, FIG. 20, can also be used to assist in tearing the liner 422a above the edge of the drape 22, as shown on the right-hand side of FIG. 22 by arrow 106 after assembly as represented by arrow 425a; liner 422a has a hole 34a in this construction, as shown on the left-hand side of FIG. 22. In this case, additional features 420 and 421, FIG. 20, beyond the indicator lines 222 and 224 are preferable, in order to provide tearing features at a variety of locations along the edge of the dressing.

Figure 23:
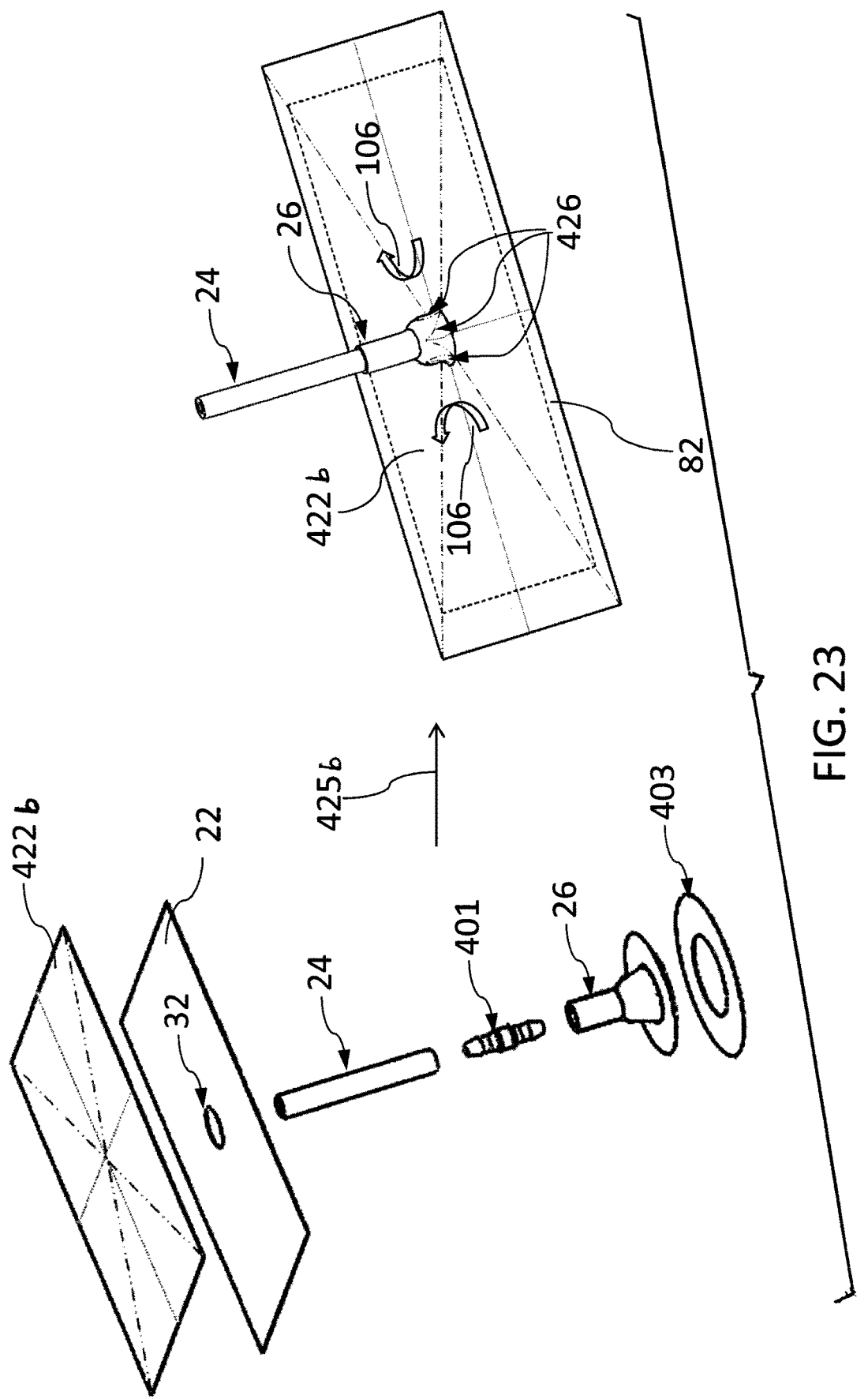
FIG. 23 shows an alternative exploded view on the left and, on the right, assembly of the liner of FIG. 20 adhered to the top of a dressing and the liner being removed.

The top liner features can also provide the ability to easily peel off the top liner 422b from the flange to the outside edge of the drape 22, as shown in FIG. 23. This is preferred in the case when peeling a top liner from the outside edge of the drape 22 to the flange 26, as described above, have a high risk to lift the outside edges of the drape 22 off of the skin. This may occur when the edge of the drape has a stronger affinity for the top liner than the skin and/or when the person applying the dressing accidently touches the adhesive on the edge of the drape and it becomes less tacky. For these top liner features in FIG. 23, it is preferred that the liner near the flange is easy to grasp by the user without disrupting the drape. Extra features can be added for this, like separate handling tabs. However, in the preferred embodiment, the flange pushes through the intersection of the perforation features during assembly represented by arrow 425b, FIG. 23, which creates un-adhered liner sections 426 around the flange for the user to grab. Each section can be removed separately by tearing the liner at the perforations, 222, 224, 420, and 421, FIG. 20. Peeling the top liner from the flange to the edge of the drape may not be the preferred method of removing the liner; for instance, in the case that the edge of the drape at the flange has a stronger affinity for the top liner than the flange. In this case, other removal methods should be considered.

When the top protective liner 30 is removed, top folds are adhered to the surface of the drape 22 with the adhesive on the top of the drape. Preferably, the folds form individual triangles on the top surface of the drape. The folds are then pressed to lie flat and be completely adhered to the surface of the drape. Pressing on all of the drape edges and top folds with the damp sponge, from the saturated sponge technique previously detailed, with or without sealant assures all of the edges are pressed flat in a "gentle" manner (due to the softness of the sponge). During this pressing process, the skin adhesive and outer adhesive (with the right thicknesses and viscosities) seal off any air paths, like a mechanically activated sealant. The adhesives do not stick to the damp sponge. The damp sponge may be used to press down the drape 22 edges, top folds, and any other area of the drape, prior to the application of sealant.

Figure 24:
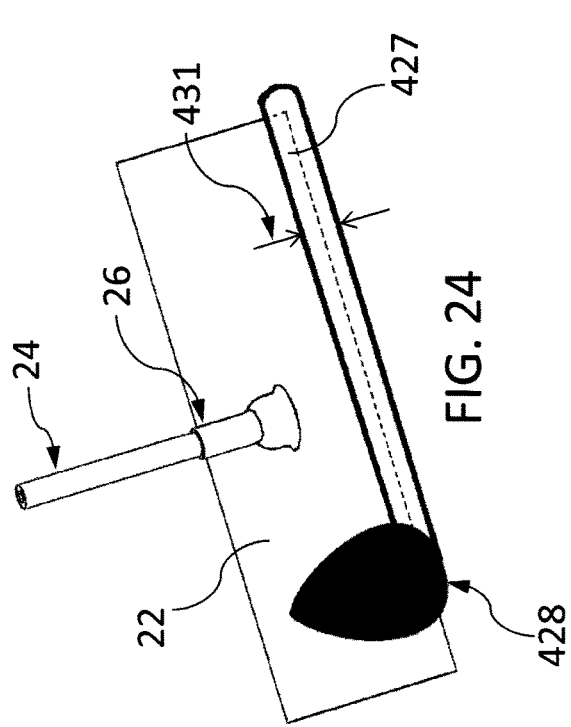
FIGS. 24-26 show the application of sealant to the edge of the dressing by sponge-type applicators of different shapes.
Figure 25:
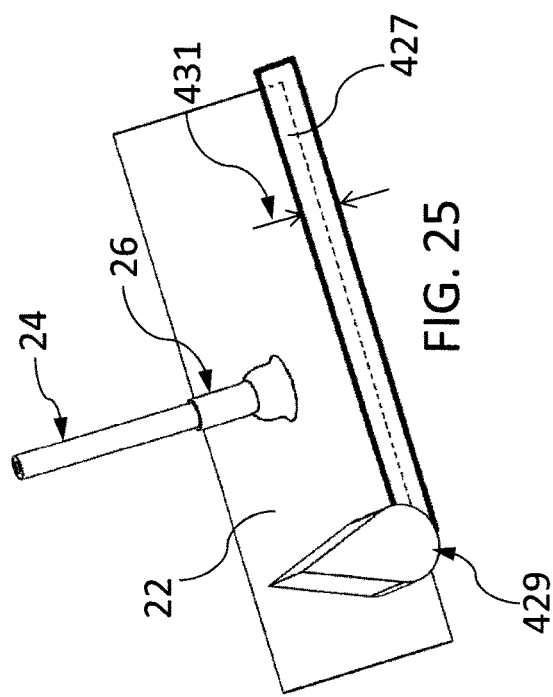
Figure 26:
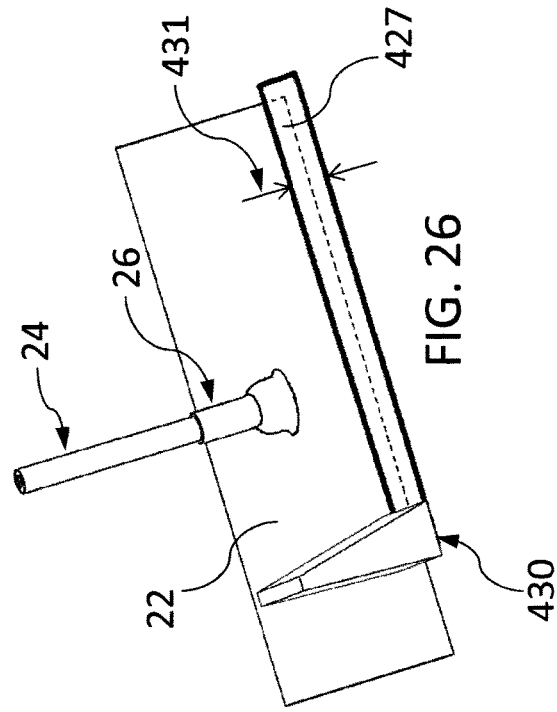

Once the drape is adhered over the wound, sealant is applied at least to the edges of the drape and the edged of any top folds, as shown on one edge 427 of the drape 22 in FIGS. 24, 25, and 26. The sealant should conform to and seal off the folds and creases in the skin, which are often bridged when applying a standard, planar wound dressing. These cracks are a significant source of air leaks into the system without a liquid sealant with the proper wetting properties. The proper wetting properties are achieved by applying the liquid sealant directly to the skin and dressing in its liquid form through a painting process or through spraying the liquid with an atomization process that eliminates liquid run-off and that may achieve a more uniform, thin film. In one preferred embodiment, the sealant applicator is a saturated sponge, which is rounded on any edges that cross the seal path during use. In the wound dressing application, an elliptical shape sponge 428, FIG. 24, would be ideal, such that no thick edges of sealant are applied. In addition, the elliptical shape provides various contours that can match the contours of the surface of the skin during use. However, in order to keep manufacturing costs down, a teardrop shape stamp of a planar sponge 429, FIG. 25 is preferred (i.e., a two-dimensional teardrop). This embodiment has no sharp edges that cross the seal path, as long as the teardrop 429 is kept perpendicular to the seal path during use, as shown in FIG. 25. To further reduce costs, a sponge with no rounded edges 430, FIG. 26 can be used, if necessary; preferably, it is the trapezoidal shape and standard size for make-up sponges 430. This allows the standard tooling to be used and eliminates waste during the stamping process. Although not ideal, it was shown during experimentation that similar results can be achieved with or without the rounded edges; however, the sponge without rounded edges 430 had a learning curve on how to smooth out any edge lines that formed over the edge of the drape 22. The width of the application width 431, FIGS. 24, 25, and 26 of the saturated sponge applicator is preferably the 2-3 cm desired width of the sealant, centered over the edge of the drape 22 and the edges of the top folds.

For application of the sealant, many application embodiments and methods are possible. For mechanical applications, including painted applications, the applicator embodiment can be a brush, roller, sponge, spatula, or other similar embodiment to apply paint in a "spreading" fashion. These spreading devices can be attached to a container (preferably refillable) of liquid sealant for a continuous feed of sealant to the applicator; this may be gravity fed (passive or user controlled), or the applicator may be prepped with sealant by dipping the applicator into a container of sealant. Although painting is not the preferred application method for the liquid dressing, it may be preferred if a high viscous sealant material is used to span large gaps, such as that between the packing material and the wound edge, the potentially high ridges of a hydrocolloid at its skin interface, or the large creases, gaps, and folds in a hydrocolloid dressing, due to its high stiffness and thickness and geometrical mismatch.

For sprayed applications, the device to atomize the sealant with a shearing process can be a refillable spray gun or airbrush, with an external pressurized gas supply, or this functionality can be incorporated into a miniature, handheld spray can, which can be rechargeable and refillable. Each embodiment has a design specific envelope of pressure, velocity and volume flow of gas that is required to shear the sealant, such that it forms a thin film, continuous layer on the skin. If the operation is outside the envelope, the droplets of the spray may be too large and will not spray as a continuous layer, but will sputter onto the skin, or the gas may not shear the fluid out of the fluid opening. In a functional embodiment, the liquid sealant is gravity fed into a center opening in a nozzle, and pressurized gas shears the sealant through a circumferential ring around the sealant nozzle opening. Multiple nozzles may exist for one or both fluids. Particularly, the spray pattern may be controlled through the shearing of the sealant from multiple gas ports, aimed in different shearing directions across the liquid sealant nozzle. In a handheld device, the pressurized gas may be generated from a miniature gas cylinder, such as a high pressure, liquid carbon dioxide cartridge. The spraying device may be charged by the caregiver when he or she activates the charged canister of gas.

Once the dressing (including the sealant and tube, if included) is applied over the wound, the wound dressing is often tacky on its outer (top) surface. This is due to the material(s) of the outer surface of the drape, including a potential layer of additional adhesive, and the material(s) of the applied sealant, including additional adhesive. Therefore, after the dressing application is complete, a cover is preferably applied to the top of the dressing, including the sealant, for long-term wear, in order to make it not tacky on the outer surface. This can be in the form of many embodiments, including but not limited to tape, medical wrap (e.g., ACE bandage by 3M, St. Paul, MN), adhesive film, non-adhesive film, powder, paint, or a combination of these materials. In the preferred embodiment, the cover does not change the functional properties of the drape, such that it causes wearability issues. For example, the cover should not increase the stiffness of the dressing components to a level that causes risk of delamination during wear. Therefore, in the preferred embodiment, a thin coat of talcum powder is used to cover the outer surface, proving minimal change in the mechanical properties of the dressing. Talcum powder can eliminate any unwanted tack on the top surface of the dressing, and it can add beneficial properties: for example, it can reduce the friction on the top surface of the dressing during wear, which can reduce the shear forces that the skin contact adhesive must withstand. The powder is ideally included in the kit, such that the caregiver does not need to provide additional material. Enough powder should be provided to cover the wound dressing.

Figure 28:
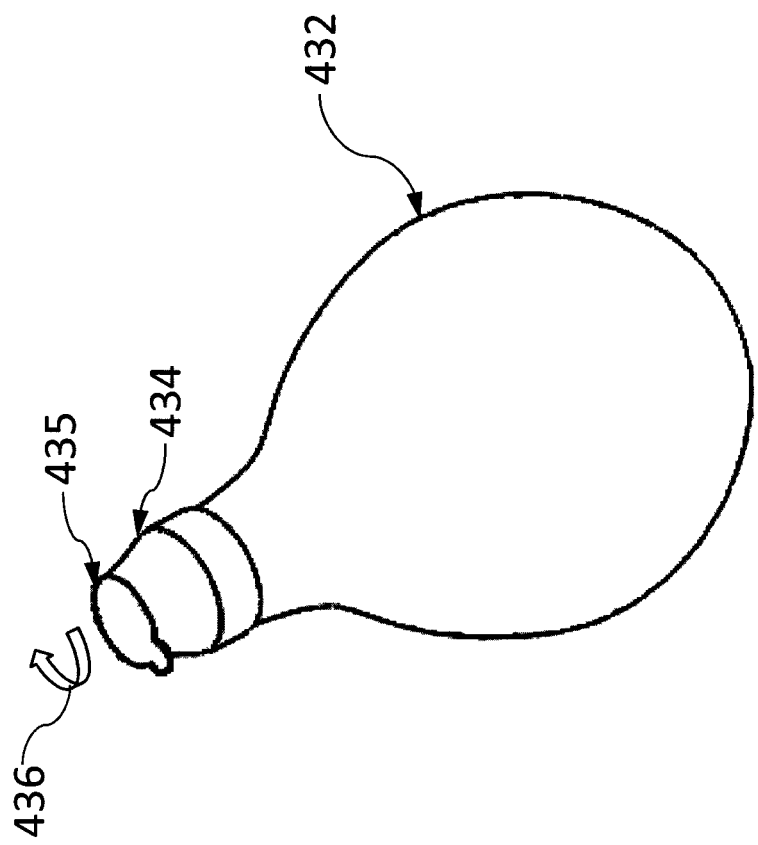
FIG. 28 shows the activation of the powder applicator of FIG. 27.
Figure 27:
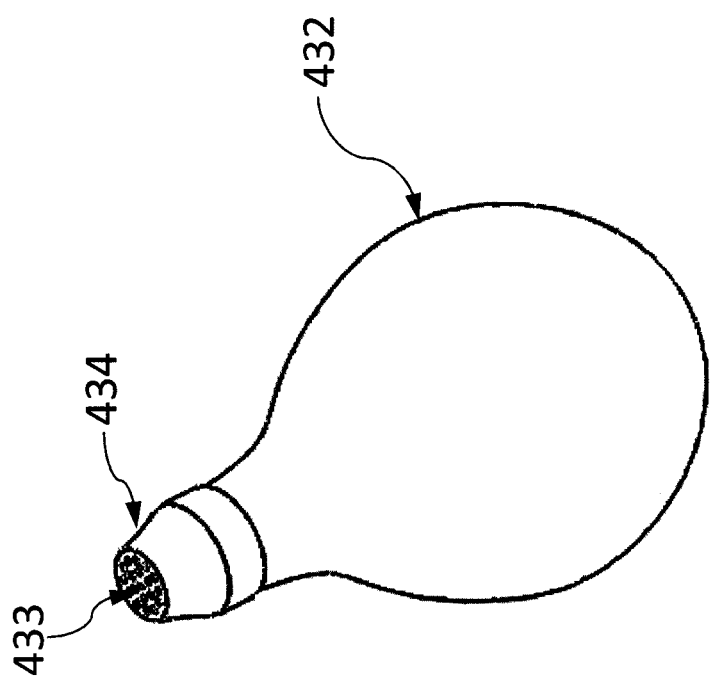
FIG. 27 shows a powder applicator.

When applying the powder, it is difficult to apply powder by-hand on surfaces that are not facing upward, due to gravity. Application by-hand tends to waste a lot of powder, as powder falls on the surfaces below the wound dressing. Therefore, a powder container that overcomes this issue may be provided. One embodiment is a powder blower, as shown in FIG. 27, similar to the barber talcum powder blower (e.g., Talcum Powder Blower by Barber Blades, Cardiff, UK). The blower consists of a flexible material 432 that can be squeezed multiple times by-hand. This component 432 is filled with powder. Powder exists the holes 433 in the cap 434. These holes 433 are small enough that with enough air forced out of the blower (by squeezing 432), powder will exist the holes 433 in a mist of powder, which can be sprayed in any direction. Ideally, this blower stores the powder provided in the kit and is disposable. A removable liner 435, FIG. 28 may be used to block the holes in the blower during transport and removed 436, FIG. 28 to activate the blower during use.

Figure 30:
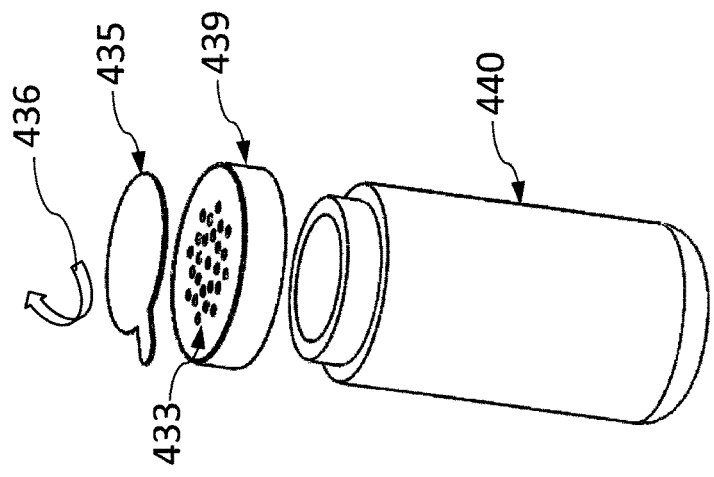
FIGS. 29-31 are schematic exploded views of powder applicators, showing their activations.
Figure 31:
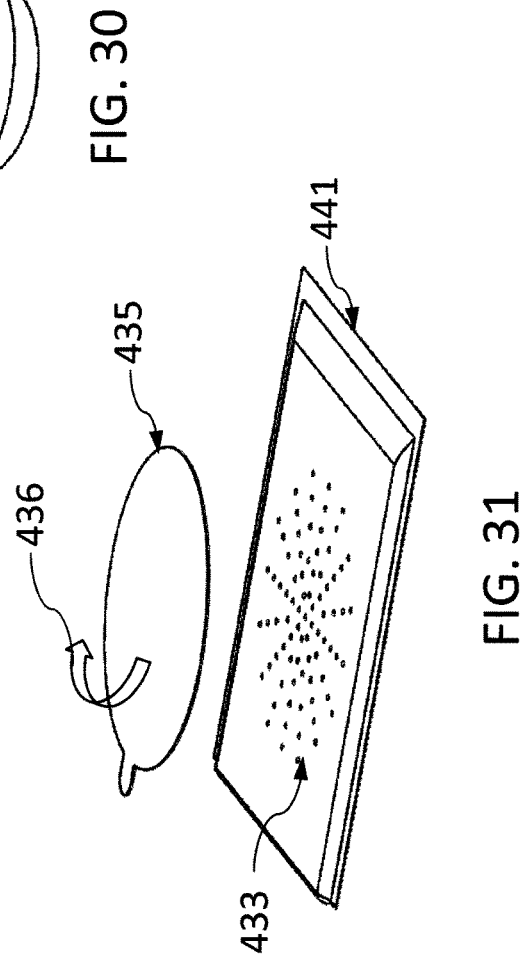
Figure 29:
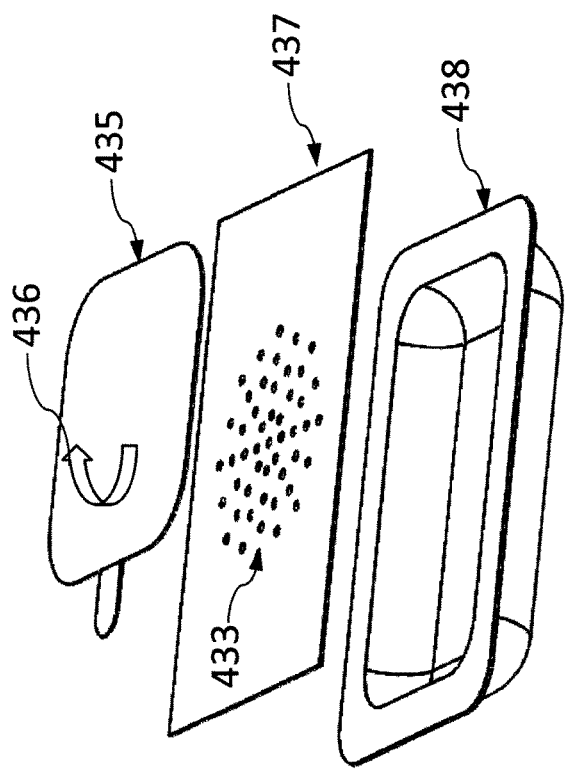

Preferable characteristics for the powder container are inexpensive, disposable, and capable of dispensing powder by preferably "blowing." One embodiment is a plastic powder spray bottle, which is commercially available in many sizes and styles (e.g., Powder Spray Bottle by Raepak Ltd, Norfolk, UK) and is typically activated by a spray pump. Another preferred embodiment is a squeezable container with a perforated lid, further examples are shown in FIGS. 29 and 30. One embodiment, shown in an exploded view in FIG. 29, is similar to a single serving jelly pack (e.g., Smucker's Single Servings, Orrville, OH) with a perforated lid 437, preferably a film, which can be made of a polymer, paper, and/or a thin metal, such as aluminum foil. Preferably, container 438, FIG. 29 is functionally similar to 432, FIG. 27, where it can be compressed multiple times for blowing functionality. Another embodiment, shown in an exploded view in FIG. 30, is a powder dispenser bottle (e.g., Plastic Bottles, White HDPE Powder Style with White Twist Top Sifter Caps by SKS Bottle & Packaging, Inc., Watervliet, NY)) with a thin perforated lid 439, such as a film, which can be made of a polymer, paper, and/or a thin metal, such as aluminum foil and can be attached with adhesive, or such as an injection molded cap, can be made of a polymer and can be attached with a mechanical attachment method, such as threads or flexures. Preferably, container 440 is functionally similar to 432, FIG. 27, where it can be compressed multiple times for blowing functionality. Hole features 433 are not necessary in the initial packaging if the user is expected to perforate the lid prior to use. Another preferred embodiment, shown in an exploded view in FIG. 31, includes a packet of powder 441, similar to the embodiment of a sugar packet, preferably with a perforated area for dispensing powder 433, as shown in FIG. 31. In order to achieve powder blowing functionality, the packet can be held in one hand and smacked against the other hand held perpendicular to the powder packet over the dressing, or the packet can be flicked with a finger while holding its perforations towards the dressing.

For NPWT, once the dressing-to-skin and tube-to-dressing interfaces are sealed (either during dressing application or during its manufacture), the caregiver should attach the tube to the vacuum source. In the preferred embodiment, a cap to vacuum chamber/collection canister has integrated at least one of: a tube connector, an inlet check valve, a purge valve, a cap/plug for the purge valve, a sealing surface, a seal component, and threads. FIGS. 32A and 32B show a preferred embodiment 452 of the cap and its features. These features serve different purposes. The tube connector 442 provides a method to connect the tube to the pump/collection canister in an air-tight fashion. In the preferred embodiment, the tube connector 442 is a barb tube connector 442 integrated into an injection molded plastic cap. This allows for easy, hand assembly by the caregiver when administering therapy. A shield 443 may provide structural protection for the barb, if the risk of the barb breaking-off during wear needs to be lowered; however, this shield is not preferable if the cap is injection molded, due to moldability issues. The inlet check valve 444 is a duckbill valve 444 in its preferred embodiment. This allows for wound exudate to enter the collection canister, but prevents the backflow of exudate to the wound cavity.

For mechanical pumps, a purge valve 445 allows the pump to be evacuated when the user compresses the pump, without the need to remove the cap from the pump. This valve is a noiseless duckbill 445, cross slit, ball, or umbrella valve; many duckbill valves had an unpleasant noise during use experimentation, and therefore, if noise is an issue, a cross slit or umbrella valve is preferred, depending on the cap design for the pump. In the preferred embodiment, this purge valve 445 has a cap or plug 446 ("cover") that should cover the purge valve 445 during therapy. This cover 446 prevents exudate from accidently being purged from the collection canister during daily wear. It also prevents any air leaks that the purge valve 445 may cause into the system, such as if particulate became trapped in the purge valve 445 overtime. In the preferred embodiment, this cover 446 is tethered 447 to the cap of the pump, so that it is not misplaced or lost. The inlet 444 and/or outlet 445 valves are occlusively held in-place by a compression plate 448. The compression plate 448 locks into the cap of the pump/collection canister with a snap fit. It has notches 449 in order to maintain alignment with the valves. In the preferred embodiment, the cap of the pump/collection canister screws onto the pump/collection canister with threads 450. This allows for the exudate to be easily emptied and the pump reset during therapy. The cap must be applied air-tight to the pump/collection canister. This can be done with a sealing surface, such as air-tight threads 450 or a luer-taper-like surface with an angle compression fit 451, or it can be accomplished with a separate seal component, such as a rubber o-ring that is compressed between the cap and pump/collection canister when the threads are tightened. If the pump and collection canister are separate components, two cap embodiments may be used with their specific features that correspond to their function. However, in the preferred embodiment, a mechanical pump is used that serves as both the vacuum source and collection canister.

Figure 33:
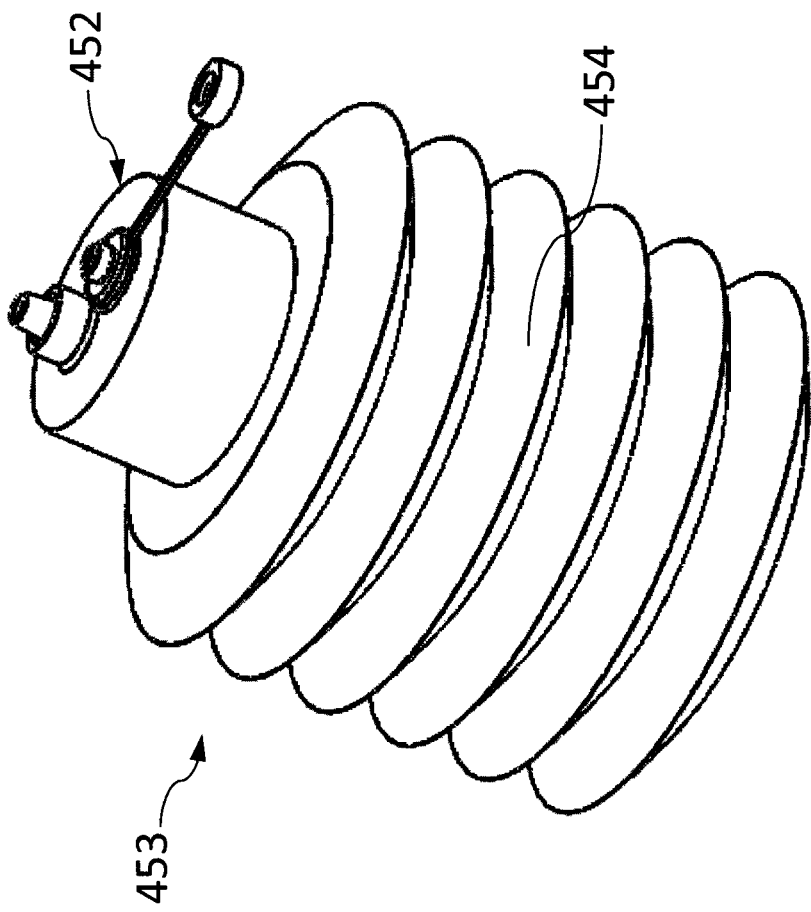
FIG. 33 shows the cap of FIGS. 32A and 32B attached to a bellows pump.
Figure 34:
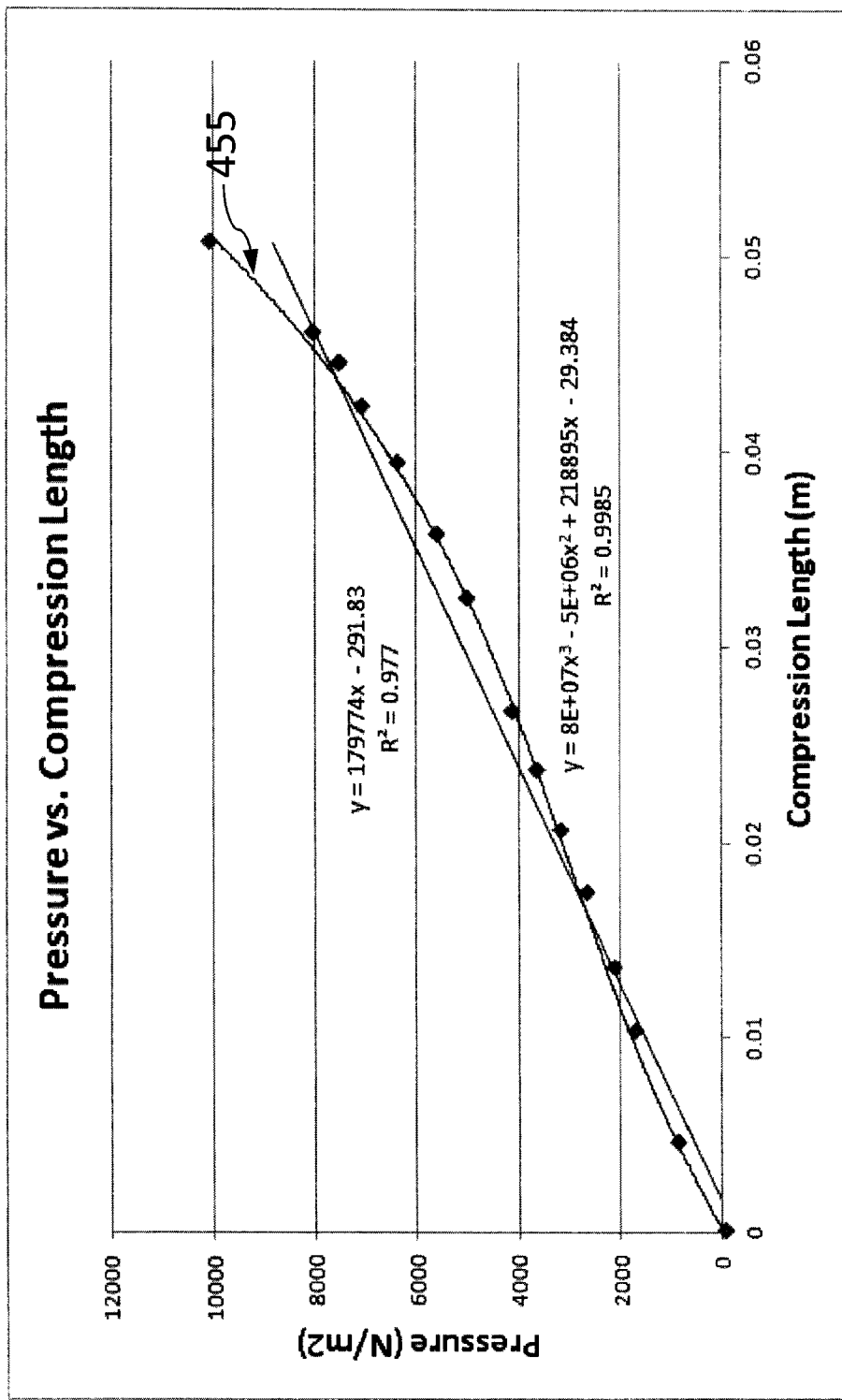
FIG. 34 is a graph showing vacuum pressure versus compression length of a bellows pump.

In negative pressure wound therapy, a vacuum pump may be connected to a wound dressing, preferably with a tube, in order to pull a vacuum on the wound cavity. Also, in wound drainage or lung drainage applications, a vacuum pump may be connected to a drain, in order to pull fluid from a cavity. After the tube and/or drain is attached to the pump, the pump should be activated. Although any mechanical or electrical vacuum source may be applied to drains or the occlusive dressings in this disclosure, a mechanical system may be preferred due to the significant benefits over electrical pumps. To administer vacuum, the pump is connected to the wound drainage tube, and the pump container is then evacuated. In one embodiment, the pump is a plastic bellows 453, shown in FIG. 33, where the enclosure and spring can be the same component. If the pump has a purge valve, the pump is preferably first attached to the tube of the wound dressing or drain, and compressed manually. A negative pressure is applied through expansion of the bellows due to the spring characteristics of its material and design. In the preferred embodiment for these applications, the bellows is blow molded from plastic, typically PVC or LDPE. The vacuum pressure applied by the pump is related to the compression length of the bellows; the pressure of the device continuously decreases over the expansion of the standard bellows due to its linear spring-like properties. A typical vacuum pressure versus compression length curve is shown in FIG. 34. Referring to the above description, one skilled in the art would realize that other embodiments exist: the device could be constructed of a different material bellows, and/or the device could contain an additional spring in parallel with the bellows in order to vary the spring constant without changing the material properties and design of the bellows itself. To change pressures in a pump design, separate pumps can be made with different material properties and/or dimensions, and/or components can be swapped for different pressure results.

As shown for a specific embodiment in FIG. 34, the pressure versus expansion length of the standard plastic bellows follows a linear trendline, yet a higher order polynomial is typically a better curve fit. Since this behavior is repetitive, the bellows can be optimized for therapy. Ideally, the reduction in pressure is minimized as exudate enters into the system. This allows for more exudate to be collected, before the predetermined pump reset pressure (a.k.a., recharge notification pressure) is reached. In this case, the initial sharp decrease 455, FIG. 34 in pressure at 100% compression is not often desirable; therefore, limiting the maximum compression of the pump is desirable to enhance functionality. Through experimentation, it has been determined that the derivative of the line is often preferable (i.e., lower) at 80% compression and even more preferable at 40-60% compression. The pressure at the limited maximum compression length (e.g., 80%) should be adjusted to the desired maximum pressure. This can be done in multiple ways, and if the same bellows embodiment is used, including materials, then the preferable method is by adjusting the wall thickness of the bellows. Varying the wall thickness can also be used to create multiple bellows with the same design and materials at varying pressures. Air leaks and wound drainage rate determine the pressure gradient, and the pressure range is determined by the maximum pressure pumped and the recharge notification pressure. The maximum vacuum pressure pumped can be limited by a pressure activated inlet valve, where the pump is compressed to the desired vacuum pressure or more, and the inlet valve lets air into the pump if the vacuum pressure is higher than the predetermined maximum vacuum pressure. The maximum vacuum pressure can also be limited by internal or external limiters, which is often preferable.

Figure 35B:
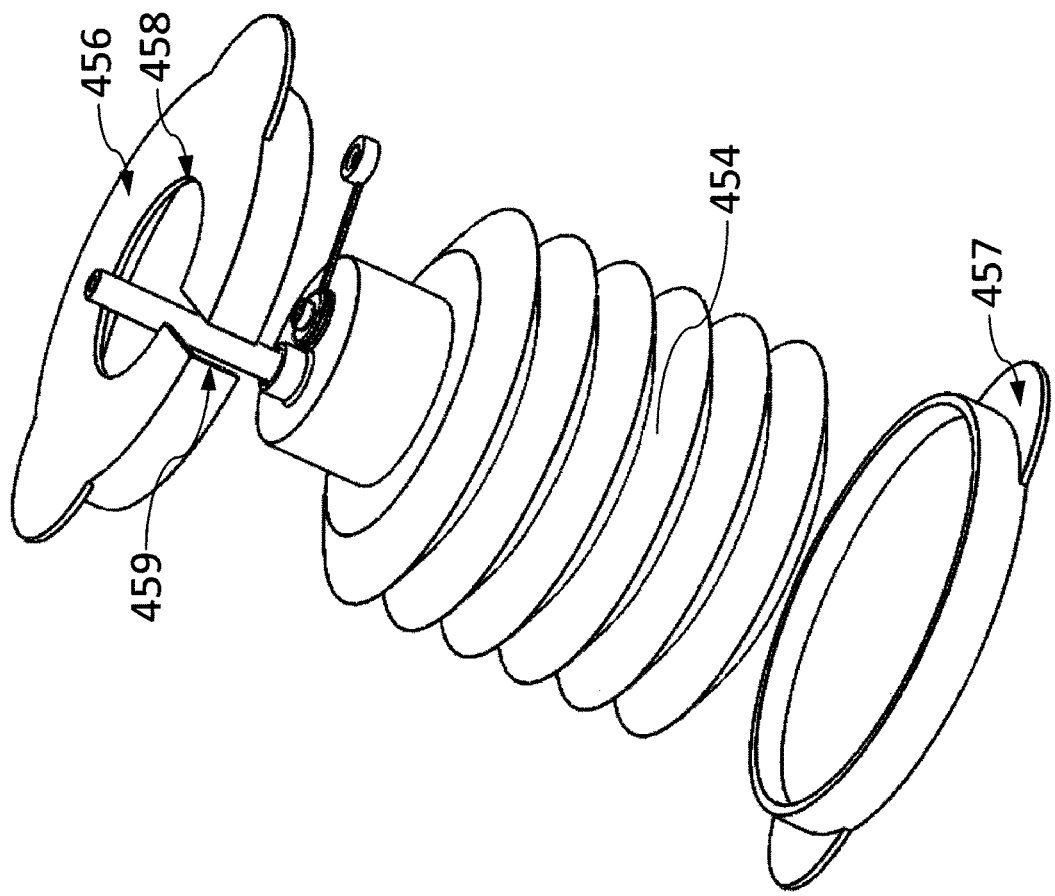
FIG. 35B shows the external compression length limiters being removed from the pump.
Figure 35A:
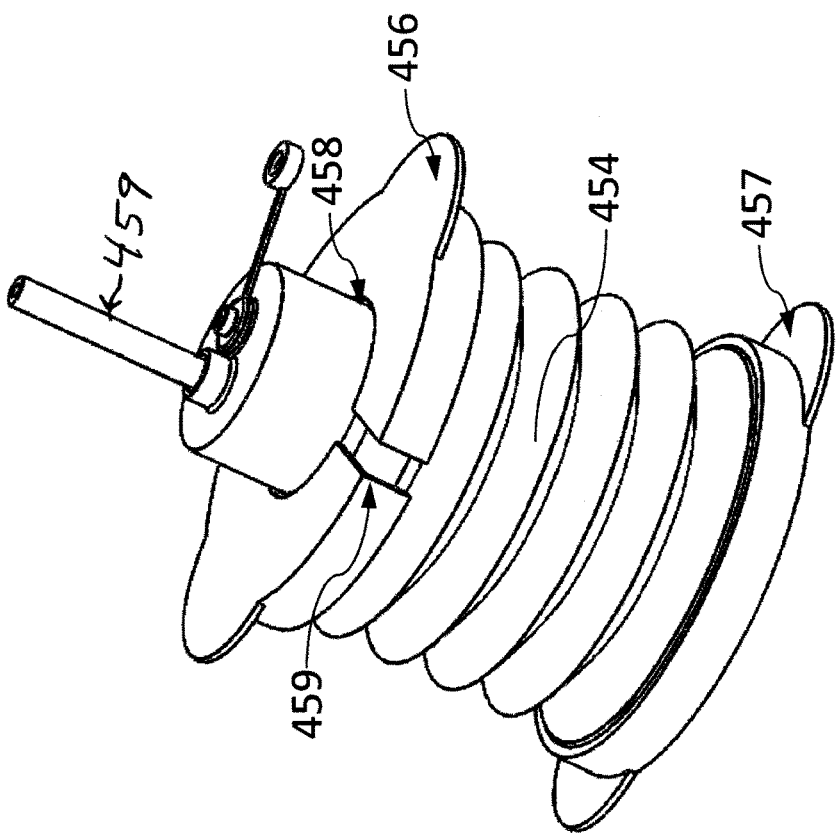
FIG. 35A shows external compression length limiters attached to the pump of FIG. 33.

Internal and/or external limiters are used to adjust the bellows maximum compression to the desired length. These can take the form of various embodiments; however, the preferred embodiments are disclosed. External limiters are used on the outside of the bellows internal volume 454. A preferred embodiment for external limiters 456 and 457, FIGS. 35A and 35B. The limiters are designed, such that the bellows can be collapsed to the desired therapy pressure length from the maximum compression of the bellows to zero. In many cases, it is preferable that external limiters are removable after compression, in order to make the pump more portable, as external limiters often add volume to the bellows footprint in space. Using external limiters for reaching the maximum therapy compression is a method of achieving repetitive, predictable maximum therapy vacuum pressure. Different users may compress the pump slightly different by-hand, and therefore, external limiters offer a method for repeatability. Also, a more predictable, accurate pressure may be achieved than through estimating or measuring the compression length. A preferable embodiment for external limiters is shown in FIG. 35. These compression plates limit the compressed length of the bellows to a predetermined length, and therefore, a predetermined pressure. The limit length may be adjustable or may be static (e.g., components 456 and 457, FIGS. 35A and 35B), based on the design of the limiters. If adjustable limiters are used, it is preferred to have the maximum therapy vacuum pressure as the variable that the user selects while adjusting the limit length. In the embodiment shown in FIGS. 35A and 35B, a place for a cap 458, which is similar to cap 452, FIGS. 32A-33, and a tube 459 to exit allows for easy removal of the top plate from the pump after compression. To save costs, the top plate can be the only component of the limiter, if it is to be pressed against a surface, such as a table top. Features similar to 458 and 459 may exist in the bottom plate, if there are features projecting from the bottom of the bellows that need to be accommodated for. One skilled in the art would realize that external limiters can be used for the compression of any mechanical pump embodiment, not just bellows, in order to offer repeatability.

Figure 36:
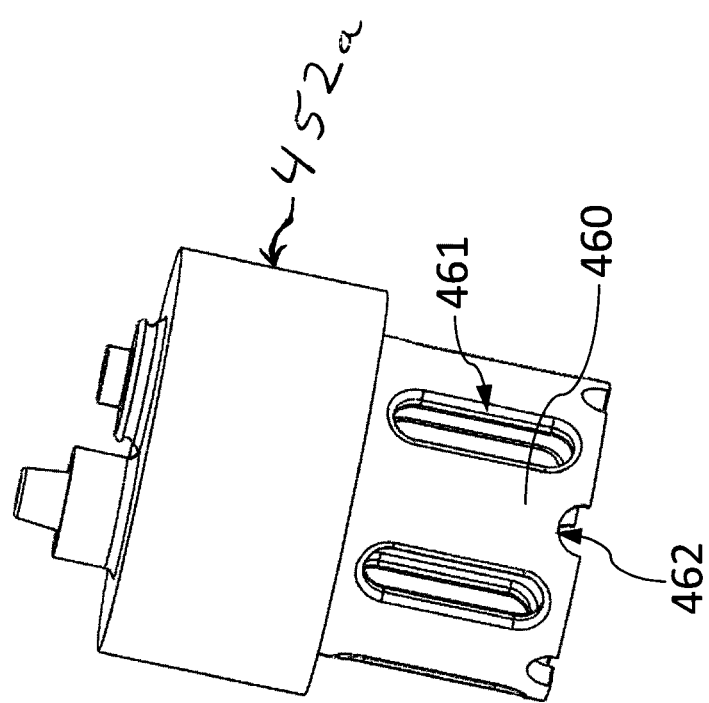
FIG. 36 shows a novel internal compression length limiter added to a cap similar to the cap of FIGS. 32A-32B.
Figure 37B:
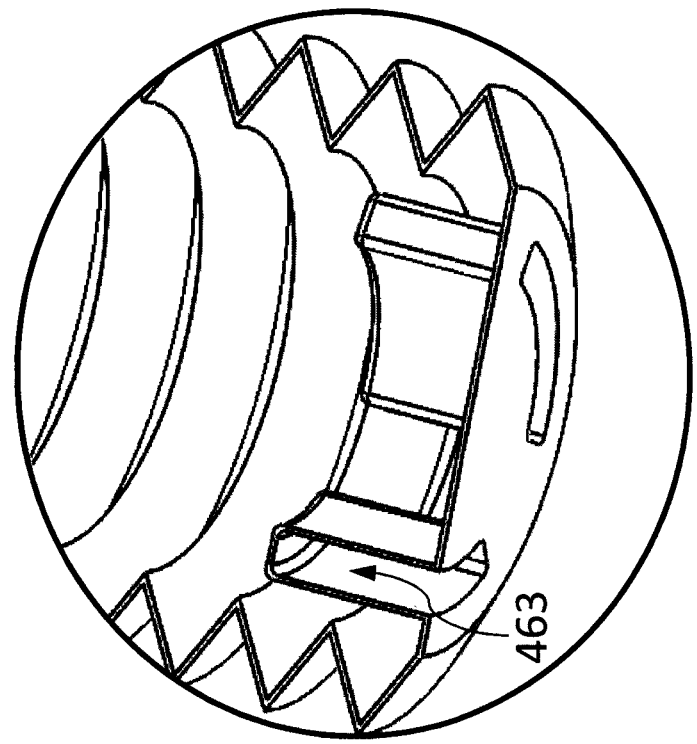
FIGS. 37A and 37B show an internal compression length limiter on a pump, with FIG. 37B being an enlarged, partial-cross-sectional view of FIG. 37A.
Figure 37A:
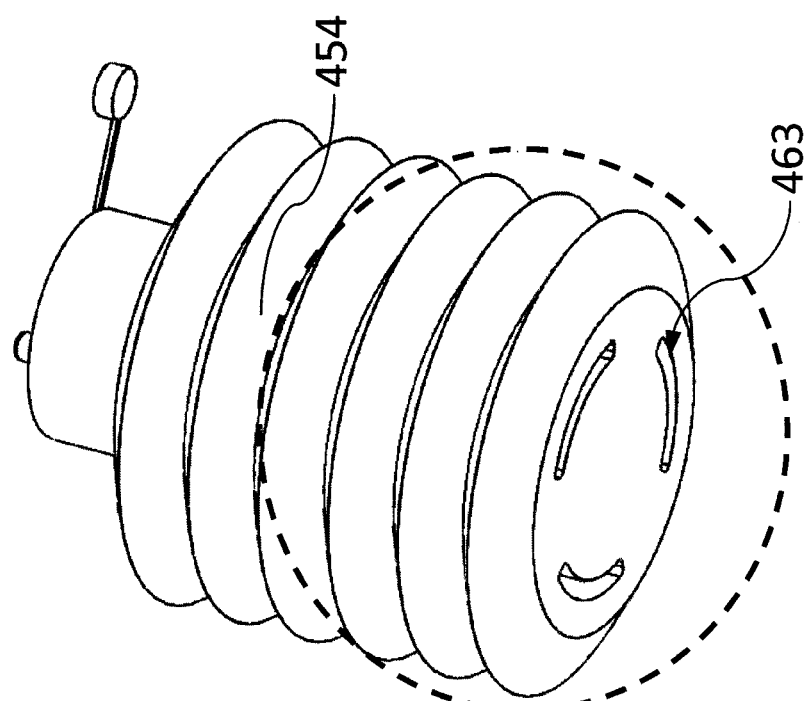

Internal limiters can also be utilized in various constructions according to the present invention. In a preferred embodiment shown in FIG. 36, the internal limiter 460 is integrated into a cap design 452a, which is similar to cap 452, FIGS. 32A-33. In its basic cap embodiment, the internal limiter functions as a hard-stop against the bottom of the pump, in order to limit the maximum compression. In order not to create a seal against the bottom of the pump, features such as 461 and/or 462 can be included in the design. These features 461 and 462 can also be used for weight savings, so that the final assembly is as light as possible for portability. Internal limiters can also be built into the pump design. In a preferred embodiment, shown in FIGS. 37A and 37B (FIG. 37B is an enlarged view of a cross section of FIG. 37A, as indicated by the dashed line in FIG. 37A), bottom features on the pump 463 protrude into the internal volume 454 of the bellows; these can be formed during manufacture of the bellows. The internal limiter functions as a hard-stop against the top of the pump, in order to limit the maximum compression. This would require a three part mold for the bellows to be removed; for this reason, this method is not preferable in many cases. Internal limiters can also exist as a separate component that is placed into the pump during assembly, and may be constrained by features on the cap and/or pump. One skilled in the art would also realize that both internal and external limiters can be used in combination embodiments.

Figure 38B:
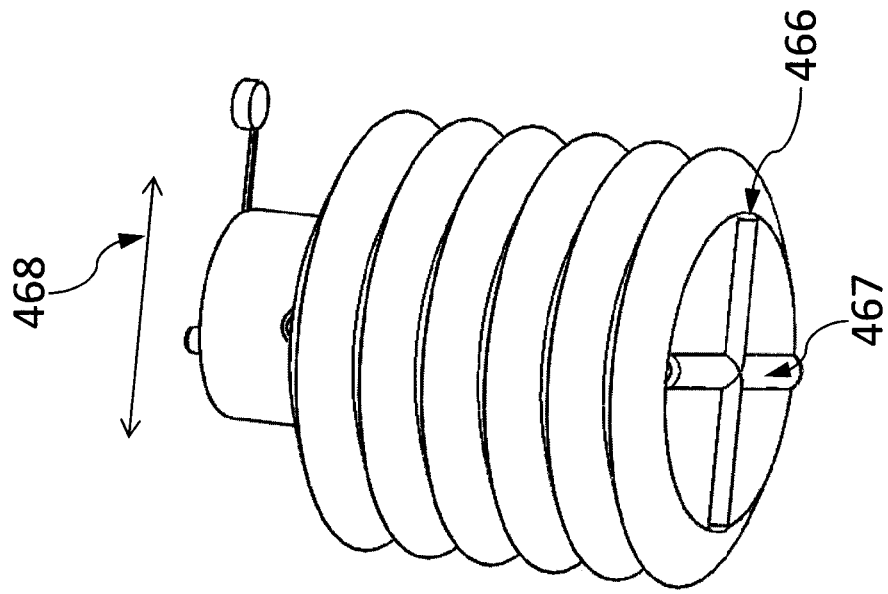
FIGS. 38A and 38B show structural support features on the top and bottom of a pump.
Figure 38A:
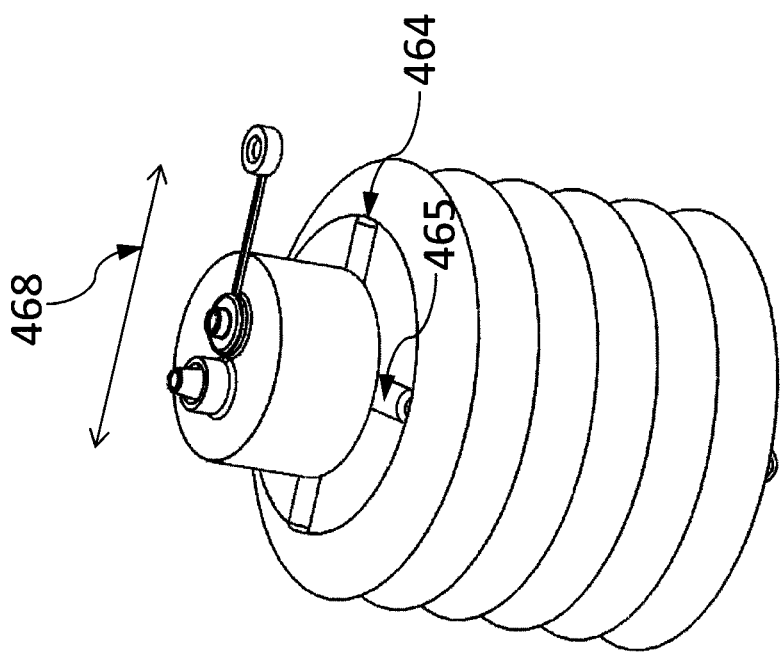

Deflection of the top and bottom of the pump may affect the vacuum pressure inside of the pump. In the bellows embodiment, this affect is not always desirable; for example, it could cause the derivative of the pressure versus compression curve to increase at 100% compression. To reduce or eliminate these effects, structural support features, such as ribs 464, 465, 466, and 467, FIGS. 38A and 38B, can be added to the top and bottom of the pump. In a blow molded embodiment, these are easily added parallel 464 and 466 and perpendicular 465 and 467 to the mold path 468, as shown in FIGS. 38A and 38B.

Figure 40:
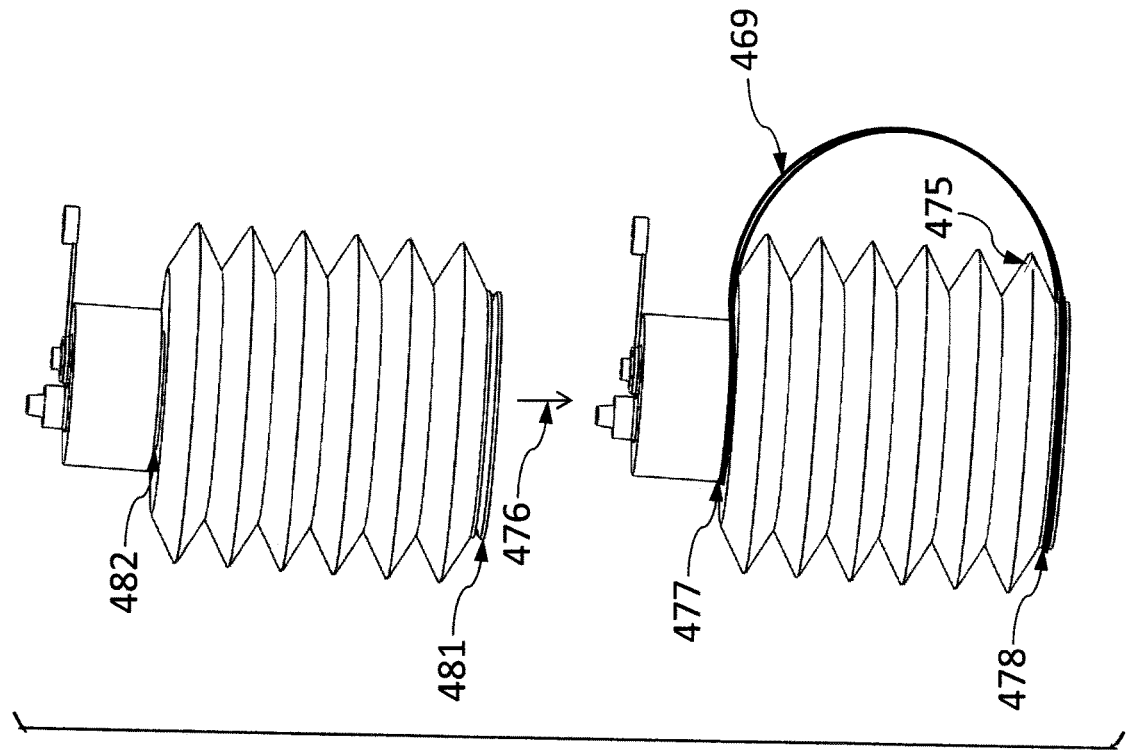
FIG. 40 shows the carrying strap of FIG. 39 being applied to a pump.
Figure 39:
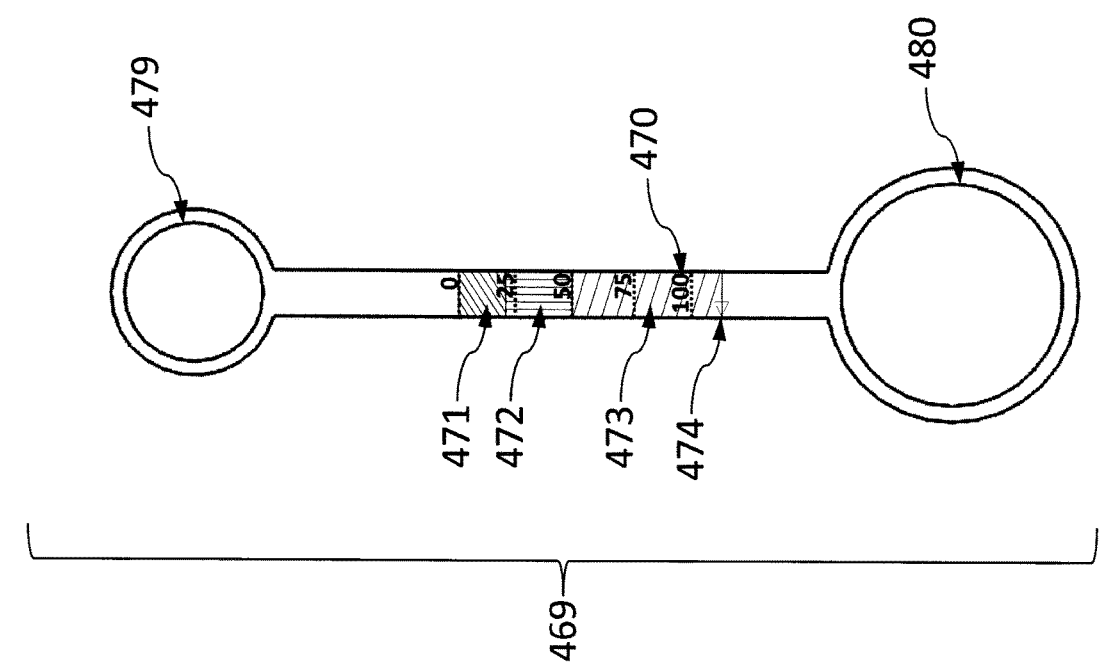
FIG. 39 illustrates a novel pump carrying strap and integrated pressure gauge.

Once compressed, the bellows pump should be monitored to assure that air is not leaking into the system above a predetermined threshold, typically zero, and to determine the therapy pressure. This can be done visually by monitoring the expansion of the pump. If there are no air leaks into the system, then the bellows is governed by the rate of wound exudate entering the system. In order to measure the pressure inside of the bellows pump, a pressure gauge can be included. For the bellows embodiment, the gauge reflects the pressure inside the pump versus the length of the pump. The user can monitor the pressure inside the pump by measuring the length of the bellows against a length gauge, FIGS. 39 and 40. With this measurement, the pressure can be kept within a pre-specified tolerance, by recompressing the pump, if necessary. The gauge embodiment may resemble a ruler or gauge 469, FIG. 39, with the numbers 470 on the line markers signifying the pressure reading during therapy. In addition, it is preferred that the ruler has specified zones, 471, 472, and 473 in order to indicate that the pressure is within the pre-specified therapy vacuum pressure range or not (e.g., zone 471 is "reset pump"; zone 472 is "therapy is o.k."; zone 473 is "therapy is good"). These zones can be specified with different colors (e.g., red, yellow, green) to indicate if the pump should be recompressed. An indicator mark may be included on at least one of (1) the gauge 469, FIG. 39, such as triangular mark 474, and (2) the pump shown in FIG. 40, with mark 475, in order to aid the user in aligning the pump with the gauge properly. In one embodiment FIGS. 39 and 40, the gauge can be printed on a carrying strap for the pump. In one embodiment FIG. 40, the carrying strap attaches 476 to the neck of the bellows opening 477 and a rim 478 on the bottom of the pump, such that the pump has a flat bottom, in order to sit upright on a table, as shown in FIG. 40. In the preferred embodiment, the top FIG. 39, 479 and bottom FIG. 39, 480 connection rings slide over top FIG. 40, 481 and bottom FIG. 40, 482 lips, respectively, during hand assembly, in order to secure their attachments onto the pump embodiment. Another embodiment is shown in FIG. 41; it is the same embodiment as FIG. 40, except the bottom lip 483 is in the shape of a small knob, and it does not allow the pump to sit upright on a table. The embodiment shown in FIG. 41 may waste less material when stamping the strap, when compared to FIG. 40, and it may also remove any unwanted affects that the deflection of any bottom features of the pump have on the applied vacuum pressure. The top connection ring can also be secured by the cap alone; however, this is not preferred if the cap is to be removed during therapy use. In another embodiment, the gauge is printed on the tube that connects the wound dressing and the bellows pump. It can be printed directly on the tube (preferred) or attached as an adhesive sticker.

In order to package the kit, it can be placed in a pouch, such as a Tyvex pouch, or a tray 484 and 485, FIG. 42. A tray offers more protection to the components and can often be stacked, which may be preferable for storage purposes. If kit trays are meant to be stacked, they are preferably able to be nested into each other 486, in order to save space. One embodiment of a nested tray is shown in FIGS. 42A and 42B, where one tray 485 is rotated 180 degrees in the horizontal plane, in order to nest into a second kit tray 484. The tray carries the larger components that need a deeper tray compartment 487 on one side of the tray, while the thin drape is held in a compartment 488 at the top of the tray with the flange projecting into the tray, in some embodiments, into its own compartment 489. When it is preferred that an individual tray can sit flat on a tabletop without tipping, a feature/compartment 490 can be included to counter the tipping force, which can also be a nesting feature for constraining the trays, as shown in FIGS. 42A and 42B.

Figure 43:
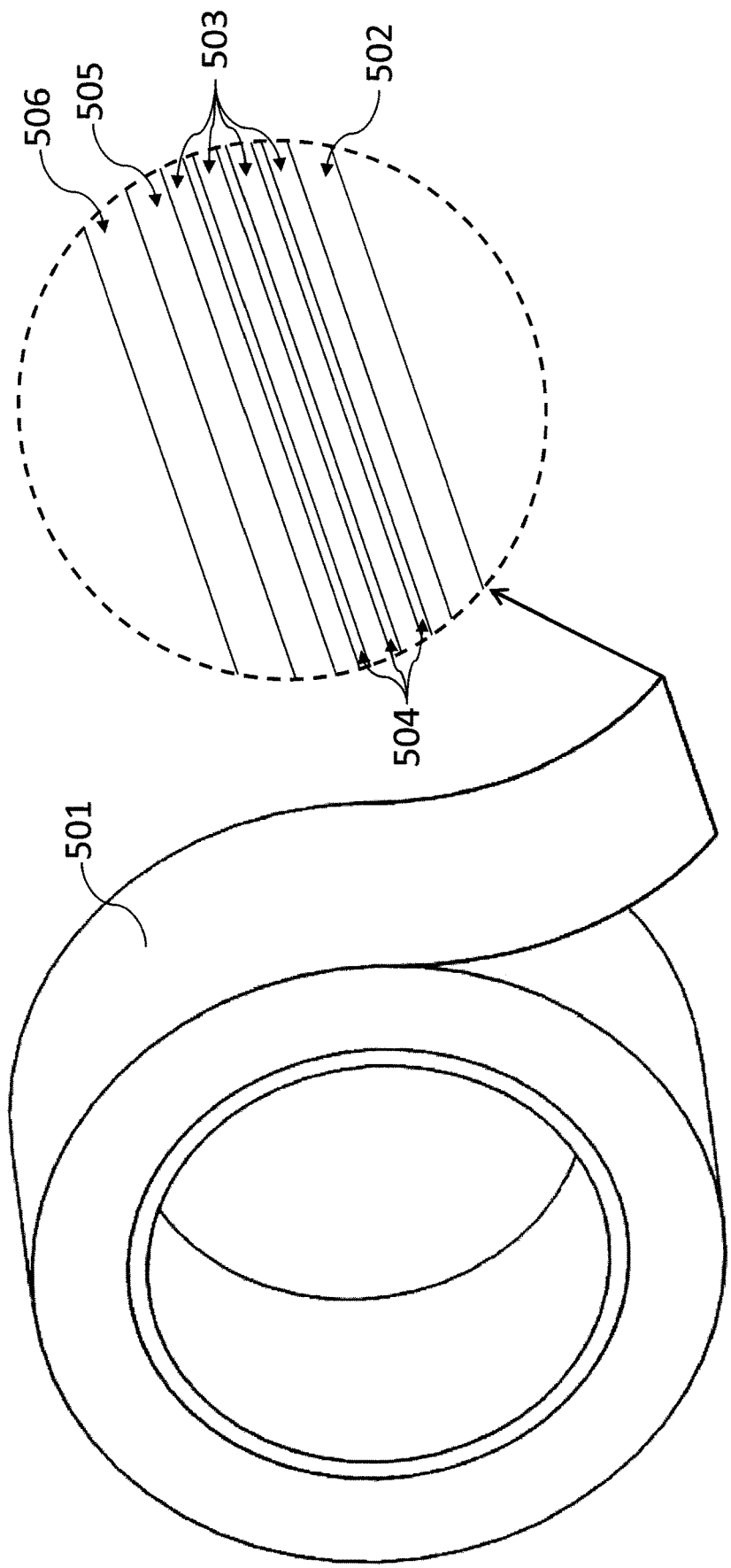
FIG. 43 illustrates a novel, unbacked liquid layer tape according to another aspect of the present invention.

FIG. 43 is a schematic of a novel liquid layered tape with a 10 layer laminate (9 adhesive layers 502-505, and 1 protective removable liner 506) construction in a "roll of tape" embodiment 501. This can be manufactured by methods including slicing a wide, finished construction roll into multiple narrower rolls, either with or without a rewinding process and/or by cutting down the length of a long finished construction roll with a rewinding process, or by laminating a single roll of tape. In practice, the individual layers can vary in width or may be in the form of a pattern, such as a grid. In its functional embodiment, the contact adhesive 502 must be able to release from the protective liner 506. Therefore, its bond with the protective liner must be weaker than the bond between the other layers, when the tape is unrolled for functional application. In addition, the contact adhesive 505 should be able to release from the protective liner 506. Therefore, its bond with the protective liner must be weaker than the bond between the other layer interfaces and ideally weaker than the functional bond between 502 and the substrate it is adhered to, when the tape is applied to a substrate. If the bond between 502 and the substrate is weaker than that between layer 505 and liner 506, then the liner 506 needs to be removed before application to the substrate, which is not preferable. If the embodiment is not used as a double-sided tape, a powder or other cover should be applied to reduce or eliminate the tack on the opposite side of the substrate.

Contact adhesives 502 and 505 do not need to be the same formula. Although the layered adhesives are shown as two layered formulas 503 and 504, every layer can be a different formula and/or thickness and/or pattern in practice. The layers 503 and 504 are each meant to be from the same coated transfer film per layer (i.e., two different coats) in the schematic, which would help to reduce complexity; therefore, in this case, each formula is a constant thickness and/or pattern. In one embodiment, the thicker layer formula 503 is the formula that drives the mechanical performance, such as a cohesive, highly elastic rubber adhesive, and the thinner layer formula 504, such as an acrylic glue, bonds the layers together and functions to create distinctive layers in order to prevent potential hole propagation during use.

Figure 44:
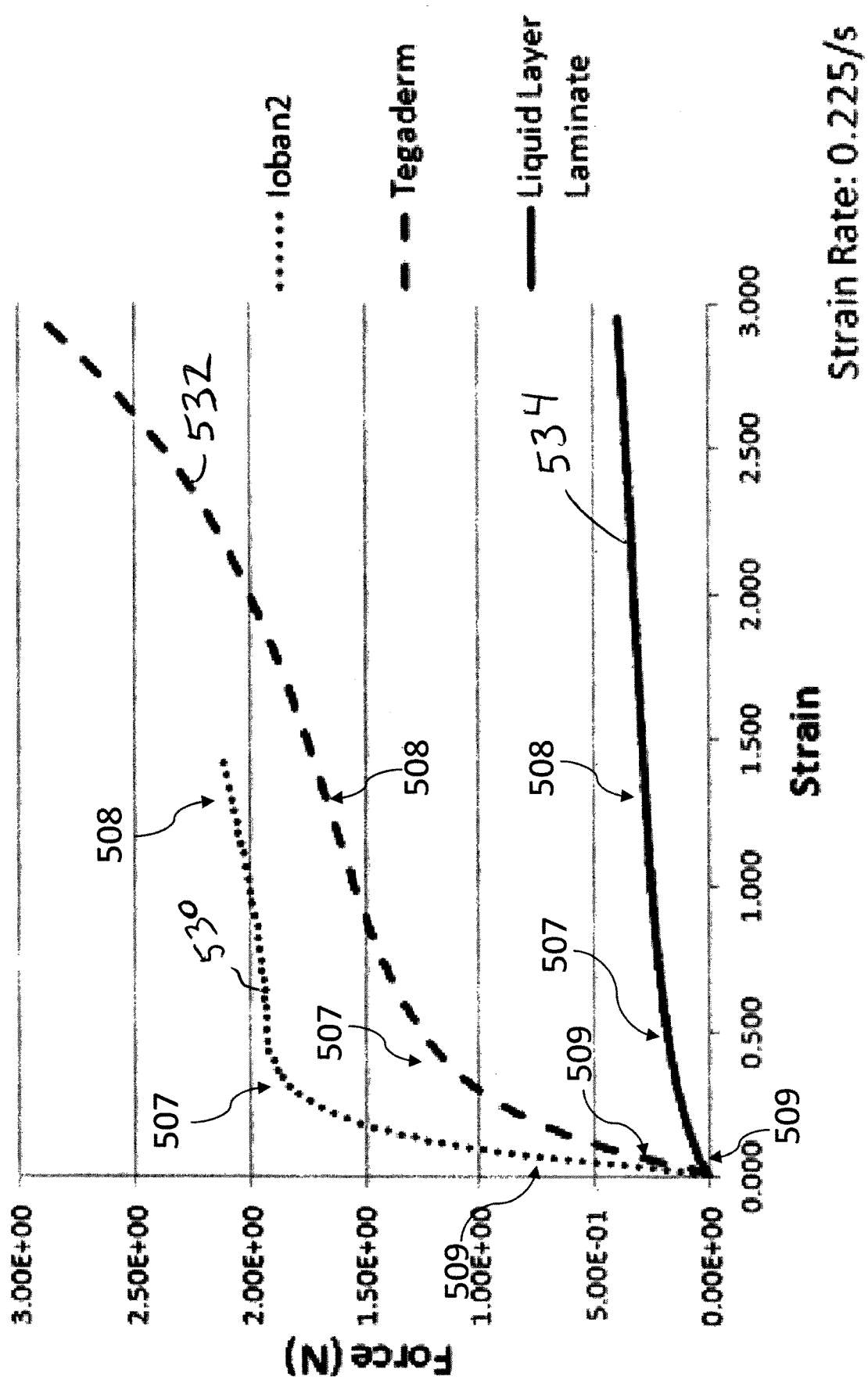
FIG. 44 is a graph showing the force versus strain relationship of tension tests on commercial wound dressings and a novel, unbacked liquid layer laminate according to the present invention.

FIG. 44 is a comparison of the force versus strain graphs for two commercial wound drape samples (Tegaderm, curve 532, and Ioban2, curve 530, by 3M, St. Paul, MN) and a liquid layered laminate, curve 534, as disclosed in this patent application. The laminate layer thicknesses were 6 mils of a rubber adhesive laminated to 5 mils of an acrylic PSA skin contact adhesive (approximately 0.28 mm total). Tegaderm is approximately 0.05 mm thick (total) and is a backing film laminated to PSA; Ioban2 is about 0.08 mm thick (total) and is a backing film laminated to a PSA. All samples were 1 cm wide. Thicknesses of individual layers are unknown for the commercial dressings, and therefore force, instead of stress, was reported for comparison purposes. The strain rate of 0.225/s reflects the strain rate of the skin surface during typical human body movements. Note that none of the samples failed during testing; Ioban2 was only strained to half the maximum strain value as the other samples. Reference numerals 507 indicates the approximate "knee", or change in slope, of each curve; as indicated, the laminate allows a much lower knee stress value at a larger strain. Also, represented in FIG. 44, the linear modulus for 0-0.1 strain, reference numerals 509, and the rubber moduli during large deformation, reference numerals 508, are significantly reduced with the new liquid layer laminate embodiment. Although force versus strain is presented in FIG. 44, the thickness of the new liquid layer laminate, including the individual layer thicknesses, is significantly higher than the total thickness of the commercial dressings, and therefore, one skilled in the art would realize that an effective stress versus strain curve would magnify these property reductions in its visual representation.

Figure 45:
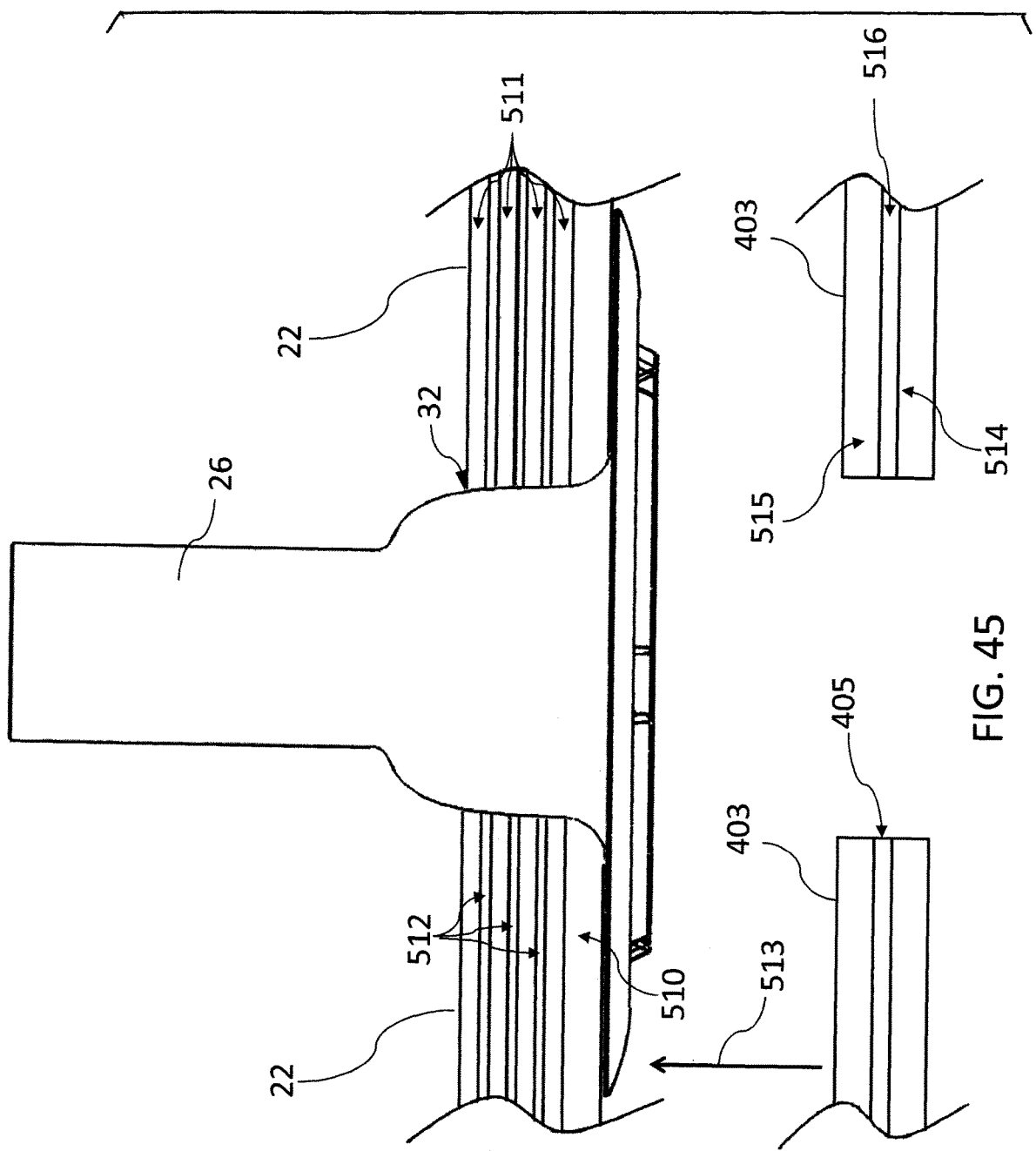
FIG. 45 illustrates a construction for a novel, unbacked liquid layer drape and adhesive patch for the kit of FIG. 2.

FIG. 45 represents a section of the new liquid layer drape embodiment used as the drape 22 in the NPWT dressing. The flange 26 is shown through a hole 32 in the drape 22. The liquid layered drape shown has an 8 layer laminate construction. One skilled in the art would realize that one or more layers can be used, depending on the properties of each adhesive. In the preferred embodiment, more than one layer is used. In many preferred embodiments that are at risk of pinhole formation, more than four layers are used, even more preferable, more than six. Although the layered adhesives are shown as two layered formulas 511 and 512, every layer can be a different formula and/or thickness and/or pattern in practice. The layers 511 and 512 are each meant to be from the same coated transfer film per layer (i.e., two different coats) in the schematic, which would help to reduce complexity; therefore, in this case, each formula is a constant thickness and/or pattern. In the preferred, the thicker layer formula 511 is the formula that drives the mechanical performance, such as a cohesive, highly elastic rubber adhesive, and the thinner layer formula 512, such as an acrylic glue, bonds the layers together and functions to create distinctive layers in order to prevent potential hole propagation during use. The skin contact adhesive 510 is a PSA in the preferred embodiment. It can be very thick in order to completely wet the surface contoured, as long as it is still structurally cohesive enough to function. In the preferred embodiment, it completely wets the surface under the drape, including around any body hair and/or in any large pores; therefore, shaving the patient is not necessary, which has clinical benefits, such as reducing infection risk, as previously discussed. In addition, the preferred embodiment completely wets the periwound surface, in order to eliminate any channels under the drape and around the wound edge that may propagate cracks and/or cause exudate to degrade the periwound skin and/or adhesive. In lab testing and during clinical trials, it was shown that if the dressing shifts slightly during 3-day wear, it did not affect occlusive performance. However, in the preferred embodiment, the dressing does not shift more than 3 cm, even more preferable less than 1 cm, and even more preferable less than 0.5 cm. In the ideal case, the dressing does not shift.

In the lower portion of FIG. 45, a section of the optional adhesive patch 403 is also shown. The embodiment shown is three layers; however, one skilled in the art would realize that one or more layers can be utilized, depending on the properties of each adhesive. In one preferred embodiment, the patch 403 is adhered, as indicated by assembly arrow 513, onto the bottom of the flange 26 and drape 22, in order to provide an extra structural support that will resist any force that would cause the flange to be pulled out of the drape hole 32, and to provide an extra occlusive barrier around the flange. It also provides a method to have an adhesive surface under the flange, in order to protect the periwound skin, in the case that the flange is applied over the periwound skin. Based on the potential for skin contact, in the preferred embodiment, the bottom adhesive 514 is the same as the skin contact adhesive 510 on the drape component. In one preferred embodiment, it is the same thickness as the skin contact adhesive on the drape. The layers 515 and 516 are two additional adhesive layers. In one embodiment, the layer 516 is the formula that drives the mechanical performance, such as a cohesive, highly elastic rubber adhesive. The layer 515 is the adhesive layer that adheres to the flange 26 and drape 22. In some embodiments, it is preferred that adhesive 515 is the same formula as the skin contact adhesive on the drape 510.

Figure 46:
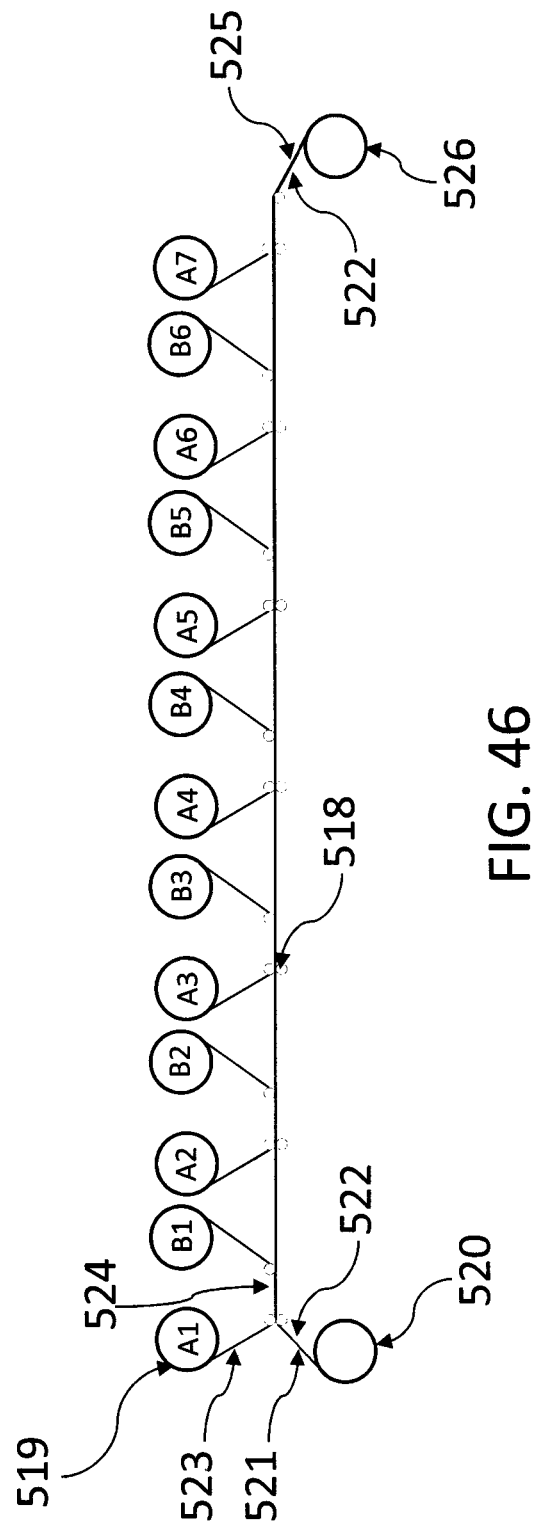
FIG. 46 is a schematic diagram of the manufacturing process for the drape of FIG. 45 according to the present invention.

One construction of a basic laminating process schematic is shown in FIG. 46 for the eight layered drape shown in FIG. 45, as an example. Positioning (i.e., vertical and horizontal position) and number of rollers 518 may vary, in order to create the proper lamination force and tension on the laminate embodiments and transfer films, and to position the right peel force/angle for film removal. Rolls 519 of a coated laminate (i.e., adhesive) layer on transfer film (A1-A7) are on rollers, so that they are fed into the process. The initial base adhesive layer 520 is on a roll that is fed into the start of the process; in the current example, this layer is the top layer of adhesive 511. The base layer has a coated adhesive side 521 and an exposed transfer film side 522. It is first laminated to the next layer of adhesive 512, which has a coated adhesive side 523 and an exposed transfer film side 524. The transfer film of roll A1 is then peeled from the laminate and rolled onto roll B1. Rolls 519 of transfer film (B1-B6) are removed from their corresponding applied laminate (i.e., adhesive) layers. Positioning (i.e., vertical and horizontal position) of rolls 519 may vary, in order to create the proper tension on the laminate embodiments and transfer films, and to create the right peel force/angle for film removal.

In the current eight layer example, roll A7 is the skin contact adhesive 510 for which its transfer film 525 is left on after lamination in FIG. 46. Transfer film 525 can also be unrolled and a new transfer film laminated to the layered construction, especially if a plough design FIG. 18A or another non-standard removable liner is desired. Roll 526 consists of a roll of the eight layer laminate with top and bottom removable liners. After further processing such as stamping, liner 525 becomes the bottom removable liner 28 of the drape 22 and liner 522 becomes the top removable liner 30. Since the bottom liner 28 needs to be removed first during drape application, it had to be laminated last (A7), as liner 28 and skin contact adhesive 510 must have the weakest adhesive bond of all the adhesive and liner interfaces during its removal in practice. One skilled in the art would realize that FIG. 46 is for example purposes, and the set-up of the manufacturing process, including the order of lamination can widely vary based on the tape design.

One skilled in the art would realize that in wound drainage or lung drainage applications, a vacuum pump or other source of negative pressure is connected to a drain, in order to pull fluid from an internal cavity. All of the features discussed regarding vacuum pumps can also be used for internal drain applications as well.

An individual sealant component may be packaged by itself to make any skin dressing occlusive. Alternatively, the sealant can be packaged as part of a mechanical NPWT kit, including a mechanical pump and its pre-attached components, tubing with flexible foot and pre-attached tubing connector and optional one way valve, dressing adhesive film to cover the packing material (if necessary), with the sealant material in a container, a sponge applicator for the sealant, a wound packing material, powder, and skin prep (if necessary). Additionally, if there is an adhesive dressing tape-like film that should be handled by the caregiver, then non-stick fingertip covers maybe included for better adhesion outcomes. Non-powdered gloves may also be included, so that the Van der Waals forces for sealant attachment are not altered due to powder on the skin surface. One skilled in the art would realize that kit components may be swapped for their different functional embodiments, discussed above. Also, additional components may be added or put into additional kits that are used in typical dressing changes, such as wound debridement tools, or additional wound therapies, such as medications with their corresponding introduction and (potentially) removal ports through the dressing, into the wound cavity.

As many dressing systems are identified in this disclosure, one skilled in the art would realize that the liquid sealing method can be used in combination with any tissue (a.k.a., skin) dressing in order to create an air-tight seal. As many pumps are identified in this disclosure, one skilled in the art would realize that any pump combined with the occlusive dressing systems would have similar performance characteristics.

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto. Other embodiments will occur to those skilled in the art and are within the following claims.

What is claimed is:

1. A tape made by a manufacturing process, suitable to adhere to a surface of a tissue and suitable to remove from the surface of the tissue by stretching the tape, comprising:
an unbacked, layered adhesive tape construction (i) defining a perimeter having at least one outer edge, (ii) defining first and second surfaces, the second surface facing oppositely to the first surface, (iii) having at least three adhesive layers, each adhesive layer being at least one of at least partially (1) dried as a solid coating or a pattern coating and/or (2) cured as a solid coating or a pattern coating and each adhesive layer being viscoelastic, the at least three adhesive layers being assembled into a final layered construction during the manufacturing process before packaging, wherein at least a portion of the final layered construction has a thickness that includes at least the at least three adhesive layers, wherein the final layered construction is constructed without a backing and is constructed as a solid coating before any further processing, wherein the final layered construction is planar and wherein the final layered construction is viscoelastic along any axis in the plane, including a selected axis, and (iv) being formed of at least first and second adhesives, the second adhesive derived from a different adhesive formula than the first adhesive;

wherein at least a portion of at least the first surface is at least one biocompatible adhesive capable of adhering to the surface of the tissue during functional use of the tape construction, the at least one biocompatible adhesive being at least one of the first and/or second adhesives;

at least one removable liner that covers at least a portion of at least one of the first and/or second surfaces of the tape construction; and wherein after removal of the at least one removable liner and after being adhered to the surface of the tissue with the at least one biocompatible adhesive, the tape construction is removable from the surface of the tissue without damaging the tissue by stretching the tape construction by applying a force of removal wherein the tape construction is lifted less than or equal to 45 degrees from the surface of the tissue.

2. The tape of claim 1 wherein at least one of the at least one removable liner covers at least a portion of the first surface of the tape construction and further including at least a second removable liner covering at least a portion of the second surface of the tape construction.

3. The tape of claim 2 wherein at least one of the at least one second removable liner covers all of the perimeter of the second surface of the tape construction and extends beyond the entire portion of any outer edge of the tape construction.

4. The tape of claim 2 wherein the second removable liner covers all of the perimeter of the second surface of the tape construction and extends beyond the entire portion of any outer edge of the tape construction.

5. The tape of claim 1 wherein the final layered construction has at least four adhesive layers and wherein the thickness of at least a portion of the final layered construction includes at least the at least four adhesive layers.

6. The tape of claim 5 wherein the thickness in a direction perpendicular to the plane sequentially includes a first adhesive layer and at least three subsequent adhesive layers, wherein at least two of the at least three subsequent adhesive layers is formed of at least one adhesive formula that includes at least one elastomer.

7. The tape of claim 5 wherein the thickness in a direction perpendicular to the plane sequentially includes a first adhesive layer and at least three subsequent adhesive layers, wherein at least two of the at least three subsequent adhesive layers is formed of at least one synthetic rubber-based adhesive formula.

8. The tape of claim 1 wherein at least one of the at least one removable liner covers at least a portion of the second surface of the tape construction.

9. The tape of claim 8 wherein at least one of the at least one of the at least one removable liner covers all of the perimeter of the second surface of the tape construction and at least one of the at least one of the at least one of the at least one removable liner covering all of the perimeter of the second surface of the tape construction extends beyond at least a portion of the at least one outer edge of the tape construction.

10. The tape of claim 1 wherein the tape construction as a whole is elastomeric along at least the selected axis.

11. The tape of claim 1 wherein the tape construction as a whole has an elastic recovery from 50 percent stretch of at least 75% in at least one direction in the plane.

12. The tape of claim 1 wherein at least a portion of each of the first surface and the second surface of the tape construction is at least one pressure sensitive adhesive.

13. The tape of claim 1 wherein each adhesive of the tape construction is at least one of a rubber-based adhesive and/or an acrylic-based adhesive and is not a silicone-based adhesive.

14. The tape of claim 1 wherein the tape construction is packaged in roll form.

15. The tape of claim 1 wherein the tape construction is further formed of at least a third adhesive, the third adhesive derived from a different adhesive formula than the first and second adhesives.

16. The tape of claim 1 wherein the tape construction is substantially impervious to fluid transfer through the thickness of the final layered construction.

17. The tape of claim 1 wherein the first surface does not include a silicone-based adhesive.

18. The tape of claim 1 wherein at least one of the at least one removable liner covering at least a portion of at least one surface of the tape construction has at least one of (1) a plough fold and/or (2) an overlapping, adjacent removable liner covering at least a portion of the at least one surface of the tape construction.

19. The tape of claim 1 wherein each adhesive of the tape construction during functional use of the tape construction is a material that, if all instances of the material are stretched uniaxially along the selected axis at a strain rate of 0.225/sec to 0.300/sec at ambient conditions, each instance has at least one of (i) a uniaxial modulus of elasticity below 1.0 MPa for the small strain range of 0 to 0.1, (ii) a uniaxial modulus of elasticity below 0.8 MPa for the small strain range of 0 to 0.2, (iii) a knee of its stress versus strain curve below a stress of 0.20 MPa and/or (iv) a stress below 0.15 MPa at a strain of 0.2.

20. The tape of claim 1 wherein each adhesive of the tape construction during functional use of the tape construction is a material that, if all instances of the material are stretched uniaxially along the selected axis at a strain rate of 0.225/sec to 0.300/sec at ambient conditions, each instance has a uniaxial modulus of elasticity below 1.0 MPa for the small strain range of 0 to 0.1.

21. The tape of claim 1 wherein each adhesive of the tape construction during functional use of the tape construction is a material that, if all instances of the material are stretched uniaxially along the selected axis at a strain rate of 0.225/sec to 0.300/sec at ambient conditions, each instance has at least one of (i) a uniaxial modulus of elasticity below 0.8 MPa for the small strain range of 0 to 0.2 and/or (ii) a stress below 0.15 MPa at a strain of 0.2.

22. The tape of claim 1 wherein each adhesive of the tape construction during functional use of the tape construction is a material that, if all instances of the material are stretched uniaxially along the selected axis at a strain rate of 0.225/sec to 0.300/sec at ambient conditions, each instance has a knee of its stress versus strain curve below a stress of 0.20 MPa.

23. The tape of claim 1 wherein each adhesive of the tape construction is a pressure sensitive adhesive.

24. The tape of claim 1 wherein the manufacturing process includes first and second rolling/unrolling directions of rolling and unrolling at least one of the at least one removable liner, wherein the second rolling/unrolling direction is opposite to the first rolling/unrolling direction, and wherein at least one of the at least one removable liner covers at least a portion of the second surface of the tape construction and extends beyond at least a portion of the at least one outer edge of the tape construction in at least one of (i) the first rolling/unrolling direction and/or (ii) the second rolling/unrolling direction.

25. The tape of claim 1 wherein the tape construction is removable from the surface of the tissue by stretching the tape construction to cause the clean release of the tape construction with no adhesive left on the surface of the tissue after removal.

26. The tape of claim 1 wherein after removal of the at least one removable liner and after being adhered to the surface of the tissue with the at least one biocompatible adhesive, the tape construction is removable from the surface of the tissue without damaging the tissue by stretching the tape construction by applying a force of removal wherein the tape construction is lifted 45 degrees from the surface of the tissue.

27. The tape of claim 1 included in a kit with at least one physically separate cover material, usable to cover at least a portion of the second surface of the tape construction after at least a portion of the first surface is applied to the surface of the tissue and suitable for preventing from sticking to other surfaces at least the portion of the second surface of the tape construction after at least the portion of the first surface is applied to the surface of the tissue.

28. The tape of claim 1 wherein the tissue is a skin.

29. The tape of claim 1 wherein the tape construction has at least one adhesive layer that is formed of at least one adhesive that is a water-based emulsion prior to the at least one adhesive layer being the at least one of at least partially (1) dried as a solid coating or a pattern coating and/or (2) cured as a solid coating or a pattern coating.

30. The tape of claim 1 wherein at least a portion of the first surface is at least one adhesive that suspends at least one of (1) an agent that includes at least one hydrocolloid and/or alginate, (2) a component that includes at least one hydrocolloid and/or alginate and/or (3) a composition that includes at least one hydrocolloid and/or alginate.

31. The tape of claim 1 wherein at least a portion of the first surface is at least one adhesive that suspends at least one of (1) an agent that includes at least one pharmaceutical and/or antimicrobial, (2) a component that includes at least one pharmaceutical and/or antimicrobial and/or (3) a composition that includes at least one pharmaceutical and/or antimicrobial.

32. The tape of claim 1 wherein the final layered construction has at least seven adhesive layers and wherein the thickness of at least a portion of the final layered construction includes at least the at least seven adhesive layers.

33. The tape of claim 1 wherein the tape construction as a whole has an elastic recovery from 50 percent stretch of at least 95% in at least one direction in the plane.

34. The tape of claim 1 included in a kit with at least one final packaging component that contains at least the tape construction and the at least one removable liner, wherein the tape construction is removable from the final packaging component by an end user for functional use of the tape construction.

35. The tape of claim 1 wherein the thickness in a direction perpendicular to the plane sequentially includes a first adhesive layer and at least two subsequent adhesive layers, wherein at least one of the at least two subsequent adhesive layers is formed of at least one rubber-based adhesive formula.

36. A kit suitable to cover an area of a surface of a tissue, comprising:
an unbacked, layered adhesive tape construction that is made by a manufacturing process, the tape construction (a) defining a perimeter having at least one outer edge, (b) defining first and second surfaces, the second surface facing oppositely to the first surface, (c) being formed of at least a first adhesive, the first adhesive derived from a first adhesive formula, and (d) (i) having one adhesive layer, at least one of at least partially (1) dried as a solid coating or a pattern coating and/or (2) cured as a solid coating or a pattern coating, constructed during the manufacturing process before packaging, constructed without a backing and constructed as a solid coating or a pattern coating before any further processing, wherein at least a portion of the one adhesive layer has a thickness of the one adhesive layer, wherein the one adhesive layer is planar and wherein the one adhesive layer is viscoelastic, or (ii) having at least two adhesive layers, each adhesive layer being at least one of at least partially (1) dried as a solid coating or a pattern coating and/or (2) cured as a solid coating or a pattern coating and each adhesive layer being viscoelastic, the at least two adhesive layers being assembled into a final layered construction during the manufacturing process before packaging, wherein at least a portion of the final layered construction has a thickness that includes at least the at least two adhesive layers, wherein the final layered construction is constructed without a backing and is constructed as a solid coating or a pattern coating before any further processing, wherein the final layered construction is planar and wherein the final layered construction is viscoelastic along any axis in the plane;
wherein at least a portion of at least the first surface is at least one biocompatible adhesive capable of adhering to the surface of the tissue during functional use of the tape construction, the at least one biocompatible adhesive being at least the first adhesive;
at least one removable liner that covers at least a portion of at least one of the first and/or second surfaces of the tape construction;
at least one physically separate cover material, usable to cover at least a portion of the second surface of the tape construction after at least a portion of the first surface is applied to the surface of the tissue and suitable for preventing from sticking to other surfaces at least the portion of the second surface of the tape construction after at least the portion of the first surface is applied to the surface of the tissue; and
wherein after removal of the at least one removable liner and after being adhered to the surface of the tissue with the at least one biocompatible adhesive, the tape construction is removable from the surface of the tissue without damaging the tissue by stretching the tape construction.

37. The kit of claim 36 wherein the tape construction (i) has at least four adhesive layers assembled into the final layered construction, wherein the thickness of at least a portion of the final layered construction includes at least the at least four adhesive layers and (ii) is formed of at least the first adhesive and a second adhesive, the second adhesive derived from a different adhesive formula than the first adhesive formula.

38. The tape of claim 37 wherein the thickness in a direction perpendicular to the plane sequentially includes a first adhesive layer and at least three subsequent adhesive layers, wherein at least two of the at least three subsequent adhesive layers is formed of at least one adhesive formula that includes at least one elastomer.

39. The kit of claim 36 wherein the at least one physically separate cover material is at least one powder and/or fine, solid particulate material.

40. The kit of claim 36 wherein the at least one physically separate cover material is at least one paint material.

41. The kit of claim 36 wherein the tape construction as a whole has an elastic recovery from 50 percent stretch of at least 75% in at least one direction in the plane.

42. The kit of claim 36 wherein each adhesive of the tape construction during functional use of the tape construction is a material that, if all instances of the material are stretched uniaxially along any axis in the plane at a strain rate of 0.225/sec to 0.300/sec at ambient conditions, each instance has at least one of (i) a uniaxial modulus of elasticity below 1.0 MPa for the small strain range of 0 to 0.1, (ii) a uniaxial modulus of elasticity below 0.8 MPa for the small strain range of 0 to 0.2, (iii) a knee of its stress versus strain curve below a stress of 0.20 MPa and/or (iv) a stress below 0.15 MPa at a strain of 0.2.

43. The kit of claim 36 wherein the tape construction is substantially impervious to fluid transfer through the thickness of the tape construction.

44. The kit of claim 36 further including at least one container of at least one sealant component that is capable of being delivered as a sealant in a liquid state at pre-selected ambient conditions, the sealant as delivered (A) being at least partially cross-linked after at least one of drying and/or curing, (B) being capable of the at least one of drying and/or curing within thirty minutes after application of the sealant when applied as an occlusive layer of sealant over the at least one outer edge of the tape construction after the tape construction is applied to the surface of the tissue with the first surface of the tape construction facing the surface of the tissue and (C) being capable of occlusively bonding to the second surface of the tape construction and the surface of the tissue surrounding the tape construction after the tape construction is applied to the surface of the tissue.

45. The tape of claim 36 wherein at least one of the at least one biocompatible adhesive is formulated to maintain an adhesion bond strength to the surface of the tissue during the functional use of the tape construction through Van der Waals forces and no other chemical bonds.

46. The kit of claim 36 further including at least one final packaging component that contains at least the tape construction and the at least one removable liner, wherein the tape construction is removable from the final packaging component by an end user for functional use of the tape construction.

47. A kit suitable for creating an occlusive seal onto a surface of a tissue, comprising:
an unbacked, layered adhesive tape construction that is made by a manufacturing process, the tape construction (a) defining a perimeter having at least one outer edge, (b) defining first and second surfaces, the second surface facing oppositely to the first surface, (c) being formed of at least a first adhesive, the first adhesive derived from a first adhesive formula, and (d) (i) having one adhesive layer, at least one of at least partially (1) dried as a solid coating or a pattern coating and/or (2) cured as a solid coating or a pattern coating, constructed during the manufacturing process before packaging, constructed without a backing and constructed as a solid coating or a pattern coating before any further processing, wherein at least a portion of the one adhesive layer has a thickness of the one adhesive layer and wherein the one adhesive layer is viscoelastic, or (ii) having at least two adhesive layers, each adhesive layer being at least one of at least partially (1) dried as a solid coating or a pattern coating and/or (2) cured as a solid coating or a pattern coating and each adhesive layer being viscoelastic, the at least two adhesive layers being assembled into a final layered construction during the manufacturing process before packaging, wherein at least a portion of the final layered construction has a thickness that includes at least the at least two adhesive layers, wherein the final layered construction is constructed without a backing and is constructed as a solid coating or a pattern coating before any further processing, wherein the final layered construction is planar and wherein the final layered construction is viscoelastic along any axis in the plane;
wherein at least a portion of at least the first surface is at least one biocompatible adhesive capable of adhering to the surface of the tissue during functional use of the tape construction, the at least one biocompatible adhesive being at least the first adhesive;
at least one removable liner that covers at least a portion of at least one of the first and/or second surfaces of the tape construction; and
at least one container of at least one sealant component that is capable of being delivered as a sealant in a liquid state at pre-selected ambient conditions, the sealant as delivered (A) being at least partially cross-linked after at least one of drying and/or curing, (B) being capable of the at least one of drying and/or curing within thirty minutes after application of the sealant when applied as an occlusive layer of sealant over the at least one outer edge of the tape construction after the tape construction is applied to the surface of the tissue with the first surface of the tape construction facing the surface of the tissue and (C) being capable of occlusively bonding to the second surface of the tape construction and the surface of the tissue surrounding the tape construction after the tape construction is applied to the surface of the tissue.

48. The kit of claim 47 further including a physically separate sealant applicator.

49. The kit of claim 47 further including at least one physically separate cover material, usable to cover at least a portion of at least one of (1) the second surface of the tape construction after at least a portion of the first surface is applied to the surface of the tissue and/or (2) the sealant after it is applied, wherein the at least one physically separate cover material is suitable for preventing from sticking to other surfaces at least the portion of at least one of (1) the second surface of the tape construction after at least the portion of the first surface is applied to the surface of the tissue and/or (2) the sealant after it is applied.

50. The kit of claim 47 wherein the tape construction (i) has the at least two adhesive layers assembled into the final layered construction and (ii) is formed of at least the first adhesive and a second adhesive, the second adhesive derived from a different adhesive formula than the first adhesive formula.

51. The kit of claim 47 wherein (i) at least one adhesive of the first surface of the tape construction, including at least a portion of the at least one outer edge, is not silicone-based and (ii) a majority of the sealant after the at least one of drying and/or curing is derived from at least one type of rubber compound that is not silicone-based.

52. The kit of claim 47 wherein (i) at least one adhesive of the second surface of the tape construction, including at least a portion of the at least one outer edge, is not silicone-based and (ii) a majority of the sealant after the at least one of drying and/or curing is derived from at least one type of rubber compound that is not silicone-based.

53. The kit of claim 47 wherein at least one adhesive of the tape construction and a majority of the sealant after the at least one of drying and/or curing are each derived from at least one type of rubber compound that is not silicone-based.

54. A tape made by a manufacturing process, suitable to adhere to a surface of a tissue and suitable to remove from the surface of the tissue by stretching the tape, comprising:

An unbacked, layered adhesive tape construction (i) defining a perimeter having at least one outer edge, (ii) defining first and second surfaces, the second surface facing oppositely to the first surface, (iii) having at least three adhesive layers, each adhesive layer being at least one of at least partially (1) dried as a solid coating or a pattern coating and/or (2) cured as a solid coating or a pattern coating and each adhesive layer being viscoelastic, the at least three adhesive layers being assembled into a final layered construction during the manufacturing process before packaging, wherein at least a portion of the final layered construction has a thickness that includes at least the at least three adhesive layers, wherein the final layered construction is constructed without a backing and is constructed as a pattern coating before any further processing, wherein the final layered construction is planar and wherein the final layered construction is viscoelastic along any axis in the plane, including a selected axis, and (iv) being formed of at least first and second adhesives, the second adhesive derived from a different adhesive formula than the first adhesive;

wherein at least a portion of at least the first surface is at least one biocompatible adhesive capable of adhering to the surface of the tissue during functional use of the tape construction, the at least one biocompatible adhesive being at least one of the first and/or second adhesives;

at least one removable liner that covers at least a portion of at least one of the first and/or second surfaces of the tape construction; and wherein after removal of the at least one removable liner and after being adhered to the surface of the tissue with the at least one biocompatible adhesive, the tape construction is removable from the surface of the tissue without damaging the tissue by stretching the tape construction by applying a force of removal wherein the tape construction is lifted less than or equal to 45 degrees from the surface of the tissue.

55. The tape of claim 54 wherein the tissue is a skin.

56. The tape of claim 54 wherein each adhesive of the tape construction during functional use of the tape construction is a material that, if all instances of the material are stretched uniaxially along the selected axis at a strain rate of 0.225/sec to 0.300/sec at ambient conditions, each instance has at least one of (i) a uniaxial modulus of elasticity below 1.0 MPa for the small strain range of 0 to 0.1, (ii) a uniaxial modulus of elasticity below 0.8 MPa for the small strain range of 0 to 0.2, (iii) a knee of its stress versus strain curve below a stress of 0.20 MPa and/or (iv) a stress below 0.15 MPa at a strain of 0.2.

57. The tape of claim 54 included in a kit with at least one physically separate cover material, usable to cover at least a portion of the second surface of the tape construction after at least a portion of the first surface is applied to the surface of the tissue and suitable for preventing from sticking to other surfaces at least the portion of the second surface of the tape construction after at least the portion of the first surface is applied to the surface of the tissue.

58. The tape of claim 54 wherein each adhesive of the tape construction is a pressure sensitive adhesive.

59. A tape made by a manufacturing process, suitable to adhere to a surface of a tissue and suitable to remove from the surface of the tissue by stretching the tape, comprising:

an unbacked, layered adhesive tape construction (i) defining a perimeter having at least one outer edge, (ii) defining first and second surfaces, the second surface facing oppositely to the first surface, (iii) having at least three adhesive layers, at least one of the at least three adhesive layers being at least one of at least partially (1) dried as a solid coating or a pattern coating and/or (2) cured as a solid coating or a pattern coating, the at least three adhesive layers being assembled into a final layered construction during the manufacturing process before packaging, wherein at least a portion of the final layered construction has a thickness that includes at least the at least three adhesive layers, wherein the final layered construction is constructed without a backing and is constructed as a solid coating or a pattern coating before any further processing, wherein the final layered construction is planar and wherein the final layered construction is viscoelastic along any axis in the plane, including a selected axis, and (iv) being formed of at least a first adhesive, the first adhesive derived from a first adhesive formula;

wherein at least a portion of at least the first surface is at least one biocompatible adhesive capable of adhering to the surface of the tissue during functional use of the tape construction, the at least one biocompatible adhesive being at least the first adhesive;

at least one removable liner that covers at least a portion of at least one of the first and/or second surfaces of the tape construction; and wherein after removal of the at least one removable liner and after being adhered to the surface of the tissue with the at least one biocompatible adhesive, the tape construction is removable from the surface of the tissue without damaging the tissue by stretching the tape construction by applying a force of removal wherein the tape construction is lifted less than or equal to 45 degrees from the surface of the tissue.

60. The tape of claim 59 wherein the tape construction is formed of at least the first adhesive and a second adhesive, the second adhesive derived from a different adhesive formula than the first adhesive formula.

61. The tape of claim 59 wherein each adhesive of the tape construction during functional use of the tape construction is a material that, if all instances of the material are stretched uniaxially along the selected axis at a strain rate of 0.225/sec to 0.300/sec at ambient conditions, each instance has at least one of (i) a uniaxial modulus of elasticity below 1.0 MPa for the small strain range of 0 to 0.1, (ii) a uniaxial modulus of elasticity below 0.8 MPa for the small strain range of 0 to 0.2, (iii) a knee of its stress versus strain curve below a stress of 0.20 MPa and/or (iv) a stress below 0.15 MPa at a strain of 0.2.

62. The tape of claim 59 wherein the final layered construction has at least four adhesive layers and wherein the thickness of at least a portion of the final layered construction includes at least the at least four adhesive layers.

63. A tape made by a manufacturing process, suitable to adhere to a surface of a tissue and suitable to remove from the surface of the tissue by stretching the tape, comprising:

an unbacked, layered adhesive tape construction (i) defining a perimeter having at least one outer edge, (ii) defining first and second surfaces, the second surface facing oppositely to the first surface, (iii) having at least three adhesive layers, at least one of the at least three adhesive layers being at least one of at least partially (1) dried as a solid coating or a pattern coating and/or (2) cured as a solid coating or a pattern coating and at least one of the at least three adhesive layers being viscoelastic, the at least three adhesive layers being assembled into a final layered construction during the manufacturing process before packaging, wherein at least a portion of the final layered construction has a thickness that includes at least the at least three adhesive layers, wherein the final layered construction is constructed without a backing and is constructed as a solid coating or a pattern coating before any further processing, wherein the final layered construction is planar and wherein the final layered construction is viscoelastic along any axis in the plane, and (iv) being formed of at least first and second adhesives, the second adhesive derived from a different adhesive formula than the first adhesive;

wherein at least a portion of at least the first surface is at least one biocompatible adhesive capable of adhering to the surface of the tissue during functional use of the tape construction, the at least one biocompatible adhesive being at least one of the first and/or second adhesives;

at least one removable liner that covers at least a portion of at least one of the first and/or second surfaces of the tape construction; and wherein after removal of the at least one removable liner and after being adhered to the surface of the tissue with the at least one biocompatible adhesive, the tape construction is removable from the surface of the tissue without damaging the tissue by stretching the tape construction by applying a force of removal wherein the tape construction is lifted less than or equal to 45 degrees from the surface of the tissue.

64. The tape of claim 63 wherein each of the at least two adhesive layers are at least one of at least partially (1) dried as a solid coating or a pattern coating and/or (2) cured as a solid coating or a pattern coating.

65. The tape of claim 63 wherein at least a portion of at least the first surface is at least two biocompatible adhesives capable of adhering to the surface of the tissue during functional use of the tape construction, the at least two biocompatible adhesives being at least the first and second adhesives.

66. The tape of claim 63 wherein the at least one biocompatible adhesive is an adhesive that requires a UV curing process.

* * * * *